(12) United States Patent
Wang et al.

(10) Patent No.: US 6,631,329 B1
(45) Date of Patent: Oct. 7, 2003

(54) USE OF THE CRYSTAL STRUCTURE OF STAPHYLOCOCCUS AUREUS ISOLEUCYL-TRNA SYNTHETASE IN ANTIBIOTIC DESIGN

(75) Inventors: Jimin Wang, Hamden, CT (US); Laura F. Silvian, Newton, MA (US); Thomas A. Steitz, Branford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/629,732

(22) Filed: Jul. 31, 2000

Related U.S. Application Data
(60) Provisional application No. 60/146,176, filed on Jul. 29, 1999.

(51) Int. Cl.[7] .................... G06F 19/00; G01N 33/48; C12Q 1/48; C12N 9/10; C12N 15/11
(52) U.S. Cl. ................... 702/19; 702/27; 435/4; 435/193; 530/350; 536/23.1
(58) Field of Search .................. 702/19, 27; 435/4, 435/193; 530/350; 536/23.1, 24.1; 549/417

(56) References Cited

PUBLICATIONS

Drenth, "Principle of protein X–ray crystallography", 1994, Springer–Verlag, Inc., New York.*

Chalker A.F. et al, "Analysis and toxic overexpression in *Esherichia coli* of a staphylococcal gene encoding isoleucyl–tRNA synthetase", Gene, 1994, vol. 141, pp. 103–108.*

Brown et al., (2000), *Biochemistry*. 39, 6003–6011.

Brown et al., (1995), *Proc. Natl. Acad. Sci. USA*, 92, 2441–2445.

Hale et al., (1997), *Science*, 276, 1250–1252.

Hong et al., (1995), *Microbiology*, 141, 2561–2567.

Hughes et al., (1980), *Biochem. J.*, 191, 209–219.

Nagel et al., (1991), *Proc. Natl. Acad. Sci. USA*, 888, 8121–8125.

Nureki et al., (1998), *Science*, 280, 578–582.

Pope et al., (1998), *J. Biol. Chem.*, 273, 31691–31701.

Silvian et al., (1999), *Science*, 285, 1074–1077.

Yanagisawa et al., (1994), *J. Biol. Chem.*, 269, 24304–24309.

* cited by examiner

*Primary Examiner*—John S. Brusca
(74) *Attorney, Agent, or Firm*—Morgan, Lewis & Bockius LLP

(57) ABSTRACT

The present invention provides the atomic coordinates derived from high resolution x-ray diffraction of the cocrystal complex comprising mupirocin with its target enzyme, isoleucyl-tRNA synthetase from *Staphylococcus aureus*, and the cognate tRNA$^{ile}$ from *Escherichia coli*. The present invention further provides methods of using the atomic coordinates to identify and design new agents which modulate protein synthesis as well as the agents themselves.

23 Claims, 24 Drawing Sheets

FIG. 6A

MODELING OF HUMAN AND MURSA IRS AND WSS

| | | ATOM TYPE | | X | Y | Z | | B | |
|---|---|---|---|---|---|---|---|---|---|
| ATOM | 1 | C1' | WSS | 1 | 38.561 | 75.401 | 83.188 | 1.00 | 53.39 | 6 |
| ATOM | 2 | O1' | WSS | 1 | 39.367 | 74.705 | 83.841 | 1.00 | 53.58 | 8 |
| ATOM | 3 | O2' | WSS | 1 | 38.963 | 76.034 | 82.185 | 1.00 | 52.93 | 8 |
| ATOM | 4 | C2' | WSS | 1 | 37.074 | 75.480 | 83.615 | 1.00 | 51.57 | 6 |
| ATOM | 5 | C3' | WSS | 1 | 36.915 | 75.997 | 85.071 | 1.00 | 48.41 | 6 |
| ATOM | 6 | C4' | WSS | 1 | 35.513 | 76.588 | 85.323 | 1.00 | 45.07 | 6 |
| ATOM | 7 | C5' | WSS | 1 | 35.443 | 78.068 | 84.897 | 1.00 | 41.55 | 6 |
| ATOM | 8 | C6' | WSS | 1 | 34.033 | 78.631 | 85.167 | 1.00 | 37.19 | 6 |
| ATOM | 9 | C7' | WSS | 1 | 33.490 | 79.356 | 83.929 | 1.00 | 34.17 | 6 |
| ATOM | 10 | C8' | WSS | 1 | 33.454 | 80.886 | 84.151 | 1.00 | 31.34 | 6 |
| ATOM | 11 | C9' | WSS | 1 | 32.082 | 81.519 | 83.803 | 1.00 | 27.63 | 6 |
| ATOM | 12 | O1A | WSS | 1 | 32.056 | 81.880 | 82.413 | 1.00 | 22.28 | 8 |
| ATOM | 13 | C1 | WSS | 1 | 30.994 | 82.769 | 82.139 | 1.00 | 18.68 | 6 |
| ATOM | 14 | O1B | WSS | 1 | 31.044 | 83.885 | 82.667 | 1.00 | 20.31 | 8 |
| ATOM | 15 | C2 | WSS | 1 | 29.949 | 82.382 | 81.280 | 1.00 | 18.38 | 6 |
| ATOM | 16 | C3 | WSS | 1 | 28.809 | 83.090 | 80.875 | 1.00 | 16.44 | 6 |
| ATOM | 17 | C15 | WSS | 1 | 28.456 | 84.523 | 81.348 | 1.00 | 12.97 | 6 |
| ATOM | 18 | C4 | WSS | 1 | 27.495 | 82.211 | 79.995 | 1.00 | 20.00 | 6 |
| ATOM | 19 | C5 | WSS | 1 | 26.029 | 82.293 | 80.409 | 1.00 | 20.00 | 6 |
| ATOM | 20 | C6 | WSS | 1 | 25.136 | 81.907 | 79.220 | 1.00 | 20.00 | 6 |
| ATOM | 21 | C7 | WSS | 1 | 23.663 | 81.759 | 79.646 | 1.00 | 20.00 | 6 |
| ATOM | 22 | C8 | WSS | 1 | 23.534 | 80.875 | 80.862 | 1.00 | 20.00 | 6 |
| ATOM | 23 | C16 | WSS | 1 | 24.419 | 81.444 | 81.951 | 1.00 | 20.00 | 6 |
| ATOM | 24 | O5 | WSS | 1 | 25.800 | 81.420 | 81.532 | 1.00 | 20.00 | 8 |
| ATOM | 25 | N7 | WSS | 1 | 23.016 | 83.134 | 79.959 | 1.00 | 20.00 | 7 |
| ATOM | 26 | CA | WSS | 1 | 23.616 | 83.828 | 81.202 | 1.00 | 20.00 | 6 |
| ATOM | 27 | NB | WSS | 1 | 22.550 | 84.789 | 81.780 | 1.00 | 20.00 | 7 |
| ATOM | 28 | CC | WSS | 1 | 22.007 | 84.144 | 83.087 | 1.00 | 20.00 | 6 |
| ATOM | 29 | OD1 | WSS | 1 | 20.624 | 83.811 | 82.918 | 1.00 | 20.00 | 8 |
| ATOM | 30 | CB2 | WSS | 1 | 23.984 | 82.871 | 82.360 | 1.00 | 20.00 | 6 |
| ATOM | 31 | CG2 | WSS | 1 | 22.828 | 82.877 | 83.361 | 1.00 | 20.00 | 6 |
| ATOM | 32 | OD2 | WSS | 1 | 22.008 | 81.713 | 83.194 | 1.00 | 20.00 | 8 |

FIG. 6B

```
ATOM     33  O6   WSS   1    25.240  82.902  78.197  1.00  20.00  8
ATOM     34  C9   WSS   1    23.964  79.449  80.524  1.00  20.00  6
ATOM     35  C10  WSS   1    22.833  78.610  79.550  1.00  19.48  6
ATOM     36  C11  WSS   1    22.999  78.593  78.193  1.00  20.56  6
ATOM     37  O10  WSS   1    22.868  77.384  78.981  1.00  21.90  8
ATOM     38  C12  WSS   1    21.733  78.839  77.305  1.00  20.86  6
ATOM     39  C17  WSS   1    21.395  80.405  77.027  1.00  20.53  6
ATOM     40  C13  WSS   1    21.779  78.052  75.821  1.00  20.74  6
ATOM     41  C14  WSS   1    20.323  77.662  75.537  1.00  22.44  6
ATOM     42  O13  WSS   1    22.524  76.868  75.987  1.00  21.25  8
HUMAN IRS (ACCORDING TO SA NUMBERING)
ATOM    559  N    ALA  70    23.950  86.066  85.381  1.00  14.18  7
ATOM    560  CA   ALA  70    22.834  86.054  84.449  1.00  14.90  6
ATOM    561  C    ALA  70    21.503  85.948  85.180  1.00  14.49  6
ATOM    562  O    ALA  70    20.529  86.641  84.780  1.00  15.96  8
ATOM    563  CB   ALA  70    22.986  84.914  83.456  1.00  14.73  6
ATOM    564  N    GLY  71    21.369  85.064  86.145  1.00  12.74  7
ATOM    565  CA   GLY  71    20.113  84.864  86.850  1.00  14.52  6
ATOM    566  C    GLY  71    19.826  86.020  87.786  1.00  14.55  6
ATOM    567  O    GLY  71    18.667  86.390  87.970  1.00  16.60  8
MURSA IRS (ACCORDING TO SA NUMBERING)
ATOM    559  N    GLY  70    23.985  86.069  85.367  1.00  14.18  7
ATOM    560  CA   GLY  70    22.830  86.052  84.481  1.00  14.90  6
ATOM    561  C    GLY  70    21.472  85.947  85.161  1.00  14.49  6
ATOM    562  O    GLY  70    20.529  86.641  84.780  1.00  15.96  8
ATOM    563  N    ARG  71    21.372  85.060  86.141  1.00  12.74  7
ATOM    564  CA   ARG  71    20.115  84.865  86.849  1.00  14.52  6
```

FIG. 6C

| ATOM | 565 | C   | ARG | 71 | 19.821 | 86.023 | 87.791 | 1.00 | 14.55 | 6 |
| ---- | --- | --- | --- | -- | ------ | ------ | ------ | ---- | ----- | - |
| ATOM | 566 | O   | ARG | 71 | 18.667 | 86.390 | 87.970 | 1.00 | 16.60 | 8 |
| ATOM | 567 | CB  | ARG | 71 | 20.138 | 83.559 | 87.641 | 1.00 | 16.20 | 6 |
| ATOM | 568 | CG  | ARG | 71 | 18.938 | 82.661 | 87.405 | 1.00 | 18.02 | 6 |
| ATOM | 569 | CD  | ARG | 71 | 18.950 | 82.104 | 85.993 | 1.00 | 20.05 | 6 |
| ATOM | 570 | NE  | ARG | 71 | 18.078 | 80.944 | 85.851 | 1.00 | 20.00 | 7 |
| ATOM | 571 | CZ  | ARG | 71 | 17.907 | 80.277 | 84.715 | 1.00 | 20.00 | 6 |
| ATOM | 572 | NH1 | ARG | 71 | 18.552 | 80.658 | 83.621 | 1.00 | 20.00 | 7 |
| ATOM | 573 | NH2 | ARG | 71 | 17.095 | 79.231 | 84.676 | 1.00 | 20.00 | 7 |

CWRC motifs in three states

FIG. IIA
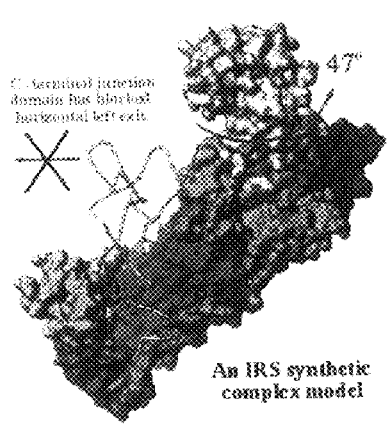
An IRS synthetic complex model
FIG. IIB
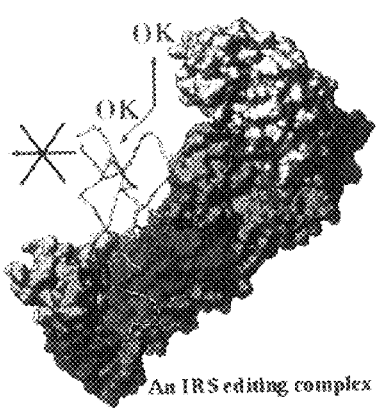
An IRS editing complex
FIG. IIC
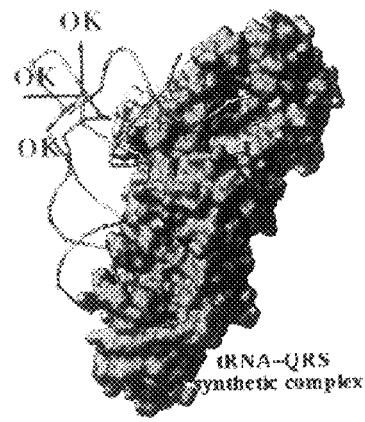
tRNA-QRS synthetic complex Synthetic site view: isolation in Apo IRS Hydrolytic site view: isolation in Apo IRS Interconnection of two active sites in tRNA-bound IRS

SEQUENCE LISTING

```
<160> NUMBER OF SEQ ID NOS: 20

<210> SEQ ID NO 1
<211> LENGTH: 9
<212> TYPE: PRT
<213> ORGANISM: Artificial sequence
<220> FEATURE:
<223> OTHER INFORMATION: Probe X

<400> SEQUENCE: 1

Val Ile Val Pro Asp Gln Val Val Lys
1               5

<210> SEQ ID NO 2
<211> LENGTH: 27
<212> TYPE: DNA
<213> ORGANISM: Artificial sequence
<220> FEATURE:
<223> OTHER INFORMATION: Probe X
<220> FEATURE:
<221> NAME/KEY: misc_feature
<222> LOCATION: (1)..(27)
<223> OTHER INFORMATION: w can be a or t

<400> SEQUENCE: 2
gttattgtwc cwgatcaagt wgttaaa                                          27

<210> SEQ ID NO 3
<211> LENGTH: 9
<212> TYPE: PRT
<213> ORGANISM: Artificial sequence
<220> FEATURE:
<223> OTHER INFORMATION: Probe Z

<400> SEQUENCE: 3

Gly Asn Ile Asn Asp Phe Asn Pro Asp
1               5

<210> SEQ ID NO 4
<211> LENGTH: 27
<212> TYPE: DNA
<213> ORGANISM: Artificial sequence
<220> FEATURE:
<223> OTHER INFORMATION: Probe Z
<220> FEATURE:
<221> NAME/KEY: misc_feature
<222> LOCATION: (1)..(27)
<223> OTHER INFORMATION: w can be a or t; y can be t or c

<400> SEQUENCE: 4
ggtaatatwa aygattttaa tccwgat                                          27

<210> SEQ ID NO 5
<211> LENGTH: 4
```

```
<212> TYPE: PRT
<213> ORGANISM: Artificial sequence
<220> FEATURE:
<223> OTHER INFORMATION: consensus amino acid motif

<400> SEQUENCE: 5

His Ile Gly His
1

<210> SEQ ID NO 6
<211> LENGTH: 5
<212> TYPE: PRT
<213> ORGANISM: Artificial sequence
<220> FEATURE:
<223> OTHER INFORMATION: consensus amino acid motif

<400> SEQUENCE: 6

Lys Met Ser Lys Ser
1               5

<210> SEQ ID NO 7
<211> LENGTH: 4
<212> TYPE: PRT
<213> ORGANISM: Artificial sequence
<220> FEATURE:
<223> OTHER INFORMATION: consensus amino acid motif

<400> SEQUENCE: 7

Gly Leu Glu Arg
1

<210> SEQ ID NO 8
<211> LENGTH: 4
<212> TYPE: PRT
<213> ORGANISM: Artificial sequence
<220> FEATURE:
<223> OTHER INFORMATION: conserved sequence motif

<400> SEQUENCE: 8

Lys Met Ser Lys
1

<210> SEQ ID NO 9
<211> LENGTH: 5
<212> TYPE: PRT
<213> ORGANISM: Artificial sequence
<220> FEATURE:
<223> OTHER INFORMATION: conserved motif

<400> SEQUENCE: 9

Trp Cys Ile Ser Arg
1               5

<210> SEQ ID NO 10
<211> LENGTH: 4
<212> TYPE: PRT
<213> ORGANISM: Artificial sequence
<220> FEATURE:
<223> OTHER INFORMATION: conserved motif

<400> SEQUENCE: 10

Cys Trp Arg Cys
1

<210> SEQ ID NO 11
<211> LENGTH: 36
<212> TYPE: DNA
```

```
<213> ORGANISM: Artificial sequence
<220> FEATURE:
<223> OTHER INFORMATION: PCR primer

<400> SEQUENCE: 11
tgaattcatg gactacaaag aaaccttatt aatgcc                    36

<210> SEQ ID NO 12
<211> LENGTH: 37
<212> TYPE: DNA
<213> ORGANISM: Artificial sequence
<220> FEATURE:
<223> OTHER INFORMATION: PCR primer

<400> SEQUENCE: 12
ttctagacat atgtaagttg ccattcgcgt acggtgg                   37

<210> SEQ ID NO 13
<211> LENGTH: 14
<212> TYPE: PRT
<213> ORGANISM: Artificial sequence
<220> FEATURE:
<223> OTHER INFORMATION: Motif in binding site in IRS
<220> FEATURE:
<221> NAME/KEY: misc_feature
<222> LOCATION: (9)..(10)
<223> OTHER INFORMATION: X can be any amino acid

<400> SEQUENCE: 13

Asp Gly Pro Pro Tyr Ala Asn Gly Xaa Xaa His Ile Gly His
1               5                   10

<210> SEQ ID NO 14
<211> LENGTH: 14
<212> TYPE: PRT
<213> ORGANISM: Artificial sequence
<220> FEATURE:
<223> OTHER INFORMATION: Motif in binding site in IRS
<220> FEATURE:
<221> NAME/KEY: misc_feature
<222> LOCATION: (3)..(9)
<223> OTHER INFORMATION: X can be any amino acid

<400> SEQUENCE: 14

Gly Phe Xaa Xaa Asp Xaa Xaa Gly Xaa Lys Met Ser Lys Ser
1               5                   10

<210> SEQ ID NO 15
<211> LENGTH: 9
<212> TYPE: PRT
<213> ORGANISM: Artificial sequence
<220> FEATURE:
<223> OTHER INFORMATION: Motif in binding site in IRS
<220> FEATURE:
<221> NAME/KEY: misc_feature
<222> LOCATION: (3)..(6)
<223> OTHER INFORMATION: X can be any amino acid

<400> SEQUENCE: 15

Glu Gly Asp Gln Xaa Arg Gly Trp Phe
1               5

<210> SEQ ID NO 16
<211> LENGTH: 6
<212> TYPE: PRT
<213> ORGANISM: Artificial sequence
<220> FEATURE:
<223> OTHER INFORMATION: Motif of the editing domain
<220> FEATURE:
```

```
<221> NAME/KEY: misc_feature
<222> LOCATION: (3)..(5)
<223> OTHER INFORMATION: X can be any amino acid

<400> SEQUENCE: 16

Thr Thr Xaa Pro Xaa Thr
1               5

<210> SEQ ID NO 17
<211> LENGTH: 15
<212> TYPE: PRT
<213> ORGANISM: Artificial sequence
<220> FEATURE:
<223> OTHER INFORMATION: Motif of the editing domain
<220> FEATURE:
<221> NAME/KEY: misc_feature
<222> LOCATION: (4)..(14)
<223> OTHER INFORMATION: X can be any amino acid

<400> SEQUENCE: 17

Gly Thr Gly Xaa Xaa Xaa Xaa Xaa Xaa Xaa Xaa Xaa Xaa Xaa Asp
1               5                   10                  15

<210> SEQ ID NO 18
<211> LENGTH: 4
<212> TYPE: PRT
<213> ORGANISM: Artificial sequence
<220> FEATURE:
<223> OTHER INFORMATION: conserved motif
<220> FEATURE:
<221> NAME/KEY: misc_feature
<222> LOCATION: (2)..(3)
<223> OTHER INFORMATION: X can be any amino acid

<400> SEQUENCE: 18

Arg Xaa Xaa Leu
1

<210> SEQ ID NO 19
<211> LENGTH: 4
<212> TYPE: PRT
<213> ORGANISM: Artificial sequence
<220> FEATURE:
<223> OTHER INFORMATION: Zn-binding motif

<400> SEQUENCE: 19

Phe Tyr Val Glu
1

<210> SEQ ID NO 20
<211> LENGTH: 4
<212> TYPE: PRT
<213> ORGANISM: Artificial sequence
<220> FEATURE:
<223> OTHER INFORMATION: ATP-binding motif

<400> SEQUENCE: 20

His Val Gly His
1
```

USE OF THE CRYSTAL STRUCTURE OF STAPHYLOCOCCUS AUREUS ISOLEUCYL-TRNA SYNTHETASE IN ANTIBIOTIC DESIGN

RELATED APPLICATIONS

This application claims the benefit of U.S. Provisional Patent Application No. 60/146,176 filed Jul. 29, 1999, which is herein incorporated by reference in its entirety.

ACKNOWLEDGMENT OF FEDERAL SUPPORT

The present invention arose in part from research funded by National Institute of Health grant GM-22778.

FIELD OF THE INVENTION

The present invention relates to the crystalline structure of isoleucyl-tRNA synthetase and the cognate tRNA$^{ile}$ and to methods of producing such crystals. The invention also relates to the atomic coordinates of isoleucyl-tRNA synthetase and the cognate tRNA$^{ile}$, obtained by x-ray diffraction at high resolution. The present invention also relates to methods for identifying and designing new classes of ligands which target the isoleucyl-tRNA synthetases of specific organisms. The methods and compositions of the present invention find wide applicability in the design and production of antibiotics, insecticides, miticides and herbicides.

BACKGROUND

Mupirocin

The most important invention in medicine in this century is perhaps the discovery of penicillin by Alexander Fleming in 1928, a naturally occurring antibiotic that inhibits cell-wall synthesis in many pathogenic bacteria. In 1940, E. B. Chain and H. W. Florey were able to produce stable commercial formulations of this antibiotic. For this invention, Fleming, Chain, and Florey shared the Nobel Prize in medicine or physiology in 1945.

In the past half century, from penicillin to methicilin to vancomycin, over 130 related antibiotics have been discovered that inhibit cell-wall synthesis (Neu, 1991). The art of the discovery is relatively simple; it requires simply a combination of microbiology and organic chemistry. Any organic chemical that inhibits bacterial cell growth by acting on cell-wall synthesis are good antibiotics, since only bacteria, not human cells, have cell wall. In comparison, the same approach that has worked for the discovery of antibiotics that inhibit cell-wall synthesis has not worked well for the discovery of antibiotics that inhibit protein synthesis.

The antibiotic for inhibition of protein synthesis, pseudomonic acid, remains in its original form since it was first discovered about three decades ago by E. B. Chain and his colleagues (Fuller et al., 1971). However, it has been since renamed as mupirocin. Mupirocin is the active ingredient of Bactroban™, a trademark of SmithKline Beecham. All attempts so far have failed to modify this antibiotic with either improved stability against unknown human hydrolase (s) for in vivo use or improved selectivity for its pathogenic target enzyme over human enzyme, simply because no organic chemists know how to modify the antibiotic to achieve the above goals.

*Staphylococcus aureus* (SA), present in about two-thirds of healthy individuals in the entire population, has a long association with nosocomial infection and is a virulent pathogen that is currently the most common cause of infections in hospitalized patients (Archer, 1998, Gould and Chamberlaine, 1995). In 1941, virtually all strains of *S. aureus* worldwide were susceptible to penicillin G, the first antibiotic used in clinics, but by 1944, *S. aureus* began to become resistant to the antibiotic, and by late 1980s, more than 95% of *S. aureus* worldwide were resistant to penicillin, amplicillin, and the antipseudomonas penicillins (Lyon and Skurray, 1987). In response, the pharmaceutical industry produced a second generation antibiotic, methicillin, a semi-synthetic penicillin. However, methicillin-resistant *S. aureus* (MRSA) became a severe problem in the 1980s (Vandenbrouche-Grauls, 1994, Mulligan et al., 1993), and is resistant to all β-lactams because it produces a new penicillin binding protein to remove all related antibiotic, pencillins, cephalosporins, carbapenems, and penems (Lyon and Skurray, 1987; Ubukata et al., 1985; Murakami and Tomasz, 1989; Tesch et al., 1988; Chambers and Sachdeva, 1990). The emergence of MRSA as a major problem worldwide has resulted in an increased use of vanomycin, the only effective antibiotic and often reserved for use in patients who are gravely ill. Its increased use has created vancomycin-resistant pathogens including *S. aureus* (Flores and Gordon, 1997, Perl, 1999, Paterson, 1999, Neu, 1992).

Mupirocin, a derivative of pseudomonic acid from *Pseudomona fluorescens* (Fuller et al., 1971), is highly effective against MRSA (Bertino, 1997, Dacre et al., 1986). Differing from cell wall-inhibiting antibiotic, it binds isoleucyl-tRNA synthetase (IRS) as a competitive inhibitor for isoleucine and inhibits protein biosynthesis (Hughes and Mellows, 1978ab; Hughes and Mellows, 1980; Yanagisawa et al., 1994; Pope et al., 1998ab). Topical use of mupirocin has very successfully eradicated the nasal carriage of MRSA (Harbarth et al., 1999; Redhead et al., 1991; Casewell and Hill, 1989; Caderna et al., 1990). This is extremely important because the anterior opening to the nasal cavities (i.e., the naris or nares), are the major site where MRSA and susceptible staphylococci persist. Topical use also eradicated MRSA in skin and virginal infections after the failure of intervenous vancomycin therapy (Denning and Haiduven-Griffiths, 1988, Cool-Foley et al., 1991). Despite these success, a person could still die in a hospital in any major city with a resistant bacterial infection. Although mupirocin resistant *S. aureus* (MURSA) is rare, it exists (Anthony et al., 1999; Schmitz et al., 1998; Gilbart et al., 1993; Farmer et al., 1992; Capobianco et al., 1989; Eltringham, 1997; Woodford et al., 1998).

Mupirocin is not very effective against bacteremia caused by MRSA because of its short half-life metabolic conversion in vivo from pseudomonic acid to inactive monic acid, which is rapidly cleared in the urine (Mellows, 1989). The pharmaceutical industry has been unsuccessful in slowing or halting the enzymatic hydrolysis by modifying the structure and function of the C1–C3 fragment, although the modified antibiotic retains good in vitro activity (Rogers 1980, Rogers and Coulton, 1882, Banks et al., 1989). This fragment has also been replaced by an unsaturated 5-membered heterocycle ring, but it must retain low-energy unoccupied molecular orbital for its inhibitory activity (Brown et al., 1997).

Selectivity of Isoleucyl-tRNA Synthetase

The high fidelity of genetic information transfer in translation is essential for the survival of organisms. Translation accuracy depends on the ability of amino acid tRNA synthethases to discriminate among tRNAs and among amino acids in amino acylation. Discrimination of L-isoleucine over L-valine by isoleucyl-tRNA synthetase is one of most difficult recognitions to achieve, because L-isoleucine and L-valine differ by only one methylene group in their aliphatic side chains. Additionally, this enzyme is the target of mupirocin, the only effective antibiotic that inhibits protein synthesis. This enzyme has therefore been extensively studied in over a half century, leading to the present invention (Silvian et al., 1999).

Isoleucyl-tRNA synthetase (IRS) selectively adds isoleucine to isoleucyl-tRNA, while rejecting all other amino acids and all other noncognate tRNAs. This enzymatic selectivity of isoleucine over valine is over 3000-fold (Loftfield, 1963; Loftfiled and Vanderjagt, 1972). If IRS were an inorganic catalyst, a free energy difference of one single methylene group between the two amino acids would provide only about 5-fold difference in selectivity (Pauling, 1958) based on an adsorption theory, which has successfully explained catalytic mechanisms for nearly all inorganic catalysts. According to the theory, inorganic catalysts (such as transition metal ions) accelerate rates of chemical reactions by increasing the collision frequency through adsorbing two reactants on catalysts' surface. The rate of enhancement is a function of adsorption of free energy, and the selectivity of given reactions is a function of free energy differences in the adsorption. A large discrepancy in selectivity of the synthetase led Baldwin and Berg (1966) to discover the hydrolytic activity of the enzyme and led Dingwall and Fersht (1979a,b) to propose a "double-sieve" hypothesis. This hypothesis predicted that there are two distinct enzymatically active sites, one hydrolytic and one synthetic. Amino acids that are larger than isoleucine are rejected by steric exclusion in the first sieve in the synthetic active site. Amino acids that are smaller than isoleucine fit into the second sieve in the hydrolytic active site and are rejected by hydrolysis.

Hydrolysis by IRS includes two substrates, both of which are the IRS synthetic products. One is an incorrectly acylated valine-tRNA$^{ile}$, also known as a post-transfer product, and the other, the dominant substrate for hydrolysis, is an activated noncognate valine-adenylate, also known as a pre-transfer product (Fersht, 1977). IRS is a model system for mechanistic studies of editing tRNA synthetases (Freist, 1989). Nureki et al. recently (1998) determined the IRS crystal structure from *T. thermophilus* (*Tth*) and showed that indeed there are two active sites, located in two distinct domains, separated by over 34 Å, providing direct evidence for the double-sieve hypothesis.

There is a parallelism between IRS and DNA polymerases. Kornberg and his colleagues (Setlow et al., 1972, Brutlag and Kornberg, 1972) discovered the hydrolytic activity in DNA polymerases, where an adsorption theory on the basis of base-pairing, which could only provide about 35–50 fold selectivity (Johnson, 1993), failed to explain the observed selectivity. The crystal structure of the Klenow fragment of *E. coli* DNA polymerase I (Ollis et al., 1985) showed that the exonuclease (hydrolytic) and the polymerase (synthetic) do not share a single active site. They are located in two distinct domains, separated by over 30 Å, a surprising result that was not anticipated by biochemical data at that time (Huberman and Kornberg, 1970). Further, the crystal structure showed that the two activities are independent of each other and can be physically separated (Freemont et al., 1986).

Crystals of IRS

Nureki et al. (1998) discloses the crystal structure of *T. thermophilus* IRS complexed to L-isoleucine or L-valine. The crystal structure has a resolution of 2.4 Å and is obtained by analysis of X-ray crystallographic diffraction data of the crystal. The crystal of Nureki et al. (1998) show that the first step in substrate selection is on the aminoacylation domain containing.the Rossmann fold, whereas the second step, the editing step, exists on a globular β-barrel domain that protrudes from the amino acylation domain. The structures of the isoleucyl-tRNA synthetases from *S. aureus* and *T. thermophilus* are homologous, and the active sites of these synthetases are also structurally similar. However, the crystal structure of Nureki et al. (1998) does not include structural information for mupirocin or tRNA$^{ile}$ and how mupirocin, other protein synthesis inhibitors, or tRNA$^{ile}$ interacts with *T. thermophilus* IRS.

The present invention discloses the crystal structure of *S. aureus* IRS complexed to muciprocin and tRNA$^{ile}$. The present invention shows how IRS interacts with an inhibitor of protein synthesis, in the presence of tRNA$^{ile}$.

SUMMARY OF THE INVENTION

The present invention provides methods of preparing crystals of a complex comprising isoleucyl-tRNA synthetase (IRS) complexed with mupirocin, and tRNA$^{ile}$ which includes mixing IRS, mupirocin, and tRNA$^{ile}$ with a well solution to form a mixture; streak-seeding drops of the mixture; vapor equilibrating the seeded drops in a closed container against the well solution to obtain a crystal of the complex and to produce an equilibrated crystal drop solution; replacing the equilibrated crystal drop solution with a cryoprotectant; and flash-freezing the crystal. More particularly the present inventions provides such methods wherein the well solution comprises about 12% PEG 6K, about 0.3 M KCl, about 100 mM Na Cacodylate pH 6.3, about 100 mM MgSO$_4$, about 2 mM ZnCl$_2$ and about 0.1% β-octyl glutopyranoside. The present invention also provides such methods wherein the seeded drops are equilibrated by hanging drop method. The present invention further provides such methods wherein the cryoprotectant comprises about 20% PEG 6K, about 0.3 M KCl, about 100 mM Na Cacodylate pH 6.3, about 100 mM MgSO$_4$, about 2 mM ZnCl$_2$ about 0.1% β-octyl glutopyranoside, and about 15% ethylene glycol. The present invention also provides such methods wherein the crystal is flash-frozen in liquid propane.

The present invention also provides crystals of IRS, mupirocin and tRNA$^{ile}$. More particularly, the present invention provides such crystals wherein the crystals effectively diffract X-rays for determination of atomic coordinates of the complex to a resolution of about 2.2 Å. Even more particularly, the present invention provides such crystals wherein the crystals have two unit cell sizes, wherein the first unit cell comprises of the dimensions a=71 Å, b=100 Å and c=186 Å and wherein the second unit cell has the dimensions a=71 Å, b=100 Å and c=180 Å. In addition, the present invention provides such crystals wherein the crystals belong to the space group $P2_12_12_1$.

The present invention provides crystals which have an atomic structure characterized by the coordinates deposited at the Protein Data bank with accession number PDB ID: 1FFY.

In particular, the present invention provides the above-listed crystals which are obtained from *Staphylococcus aureus*.

The present invention also provides methods for identifying agents (ligands) that interact with IRS and tRNA$^{ile}$, wherein such methods include obtaining a crystal of a complex comprising IRS, tRNA$^{ile}$ and mupirocin; obtaining the atomic coordinates of the crystal; and using the atomic coordinates and one or more molecular modeling techniques to identify an agent that interacts with IRS and tRNA$^{ile}$.

The present invention further provides methods of identifying agents (ligands) that interact with IRS wherein such methods include obtaining a crystal of a complex comprising IRS, tRNA$^{ile}$ and mupirocin; obtaining the atomic coordinates of the crystal; and using the atomic coordinates and one or more molecular modeling techniques to identify an agent that interacts with IRS.

More particularly, the present invention provides such methods of identifying agents (ligands) wherein the one or more molecular modeling techniques include graphic molecular modeling and computational chemistry.

The present invention further provides such methods of identifying agents (ligands) and then contacting the agents with IRS and detecting the amount and degree of binding of the agents to IRS. The methods of the present invention can be used to identify agents that bind to enzymes from the same or different species as the species from which the enzyme was obtained to produce the crystal.

The present invention further provides such methods of identifying agents which include altering the identified agents and contacting the altered agents with IRS and determining the binding of the altered agents to IRS.

The present invention also provides altered agents produced by such methods wherein the altered agents bind differently to IRS than do the agents from which the altered agents were derived. The present invention further provides such altered agents wherein the altered agents are therapeutic agents. More particularly, the present invention provides such altered agents wherein the altered agents have desirable pharmaceutical properties. The invention further provides compositions which include such altered agents combined with pharmaceutically-acceptable carriers.

More particularly, the present invention provides altered agents which act as inhibitors of IRS. The agents of the present invention can be specifically designed to kill or act as inhibitors of target organisms while not killing non-target organisms or inhibiting non-target organisms less at the same concentration of the altered agents.

The present invention also provides methods of identifying inhibitors of protein synthesis which include obtaining crystals of a complex comprising IRS, tRNA$^{ile}$ and mupirocin; obtaining the atomic coordinates of the crystals; using the atomic coordinates and molecular modeling techniques to identify agents that interact with IRS; assaying the inhibitory properties of the agents by administering them to cells, cell extracts or purified IRS; and detecting protein synthesis, wherein a decrease in protein synthesis indicates that the agents are inhibitors of protein synthesis. The present invention also provides such methods wherein assaying the inhibitory properties of the agents includes detecting protein synthesis and wherein a decrease in protein synthesis indicates that the agents are inhibitors of protein synthesis. The present invention also provides such methods wherein assaying the inhibitory properties of the agents includes determining an inhibition constant for inhibiting isoleucyl-tRNA synthesis reaction by the agents.

The present invention also provides methods of identifying inhibitors of protein synthesis which include obtaining crystals of a complex comprising IRS, tRNA$^{ile}$ and mupirocin; obtaining the atomic coordinates of the crystals; using the atomic coordinates and molecular modeling techniques to identify agents that interact with IRS; and assaying the inhibitory properties of the agents by administering them to cells, a cell extracts or purified IRS to determine whether they are inhibitors of protein synthesis. The present invention also provides such methods wherein assaying the inhibitory properties of the agents includes determining whether the agents inhibit isoleucyl-tRNA synthesis. More particularly, the present invention provides such methods wherein whether the agents inhibit isoleucyl-tRNA synthesis are determined by measuring the generation of pyrophosphate or the formation of isoleucyl-tRNA$^{ile}$.

Dashed arrows represent hydrogen bonds between the antibiotic and the enzyme. The dashed arcs indicate important hydrophobic interactions.

Part A, also known as the head of the antibiotic, is the portion of the molecule that corresponds to carbons 9–14 of mupirocin.

Part B, also known as the central portion, is the portion of the molecule that mimics the adenosine-ring portion of the adenylate. HIGH (SEQ ID NO: 5) and KMSK (SEQ ID NO: 8) are the two conserved sequence motifs. Filled triangles represent stereoisomers with the bonds pointing to the viewer; opened triangles represent stereoisomers with the bonds pointing away from the viewers. Amino acids of the enzyme represent defined elsewhere herein.

Figure 2:
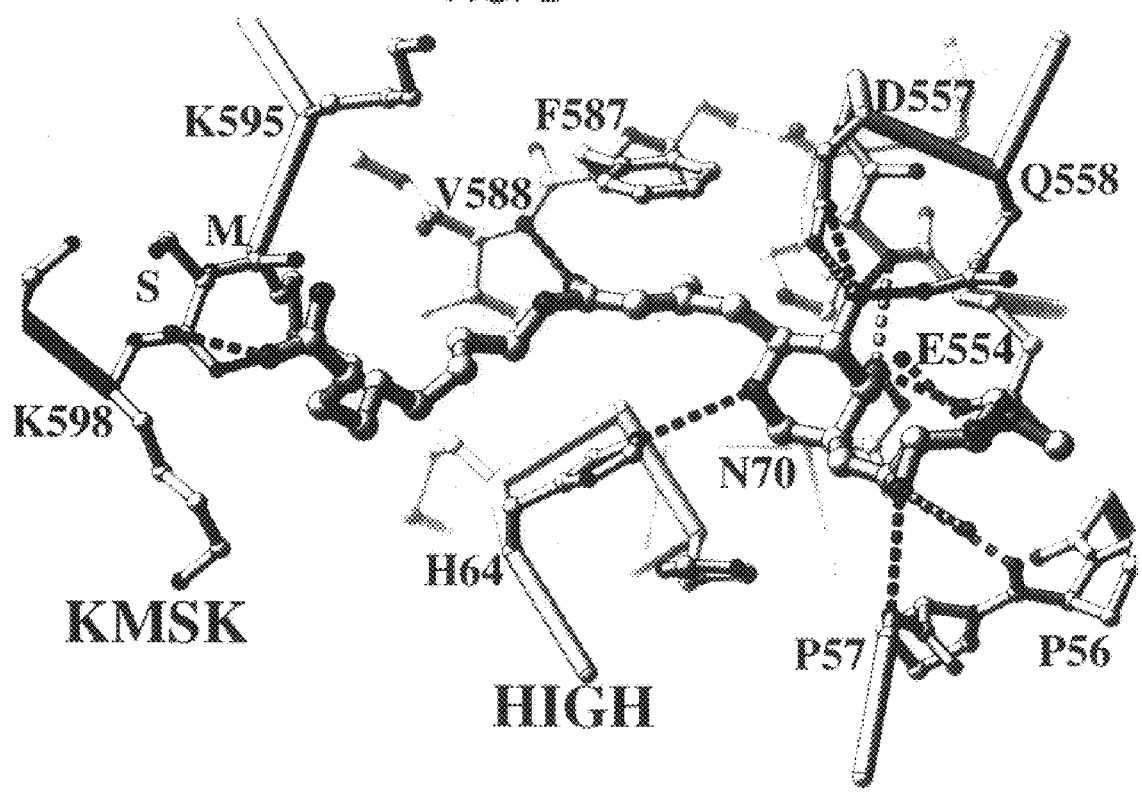

FIG. 2. The Binding Site of Mupirocin on Isoleucyl-tRNA Synthetase.

A three-dimensional drawing of the mupirocin binding site of the enzyme. Hydrogen bonds are in dashes. The mupirocin binding site comprises residues P56, P57, H64, G66, N70, E554, G555, D557, Q558, W562, H585, G586, F587, V588, M596, and S597. Amino acids of the enzyme are defined elsewhere herein.

Figure 3:
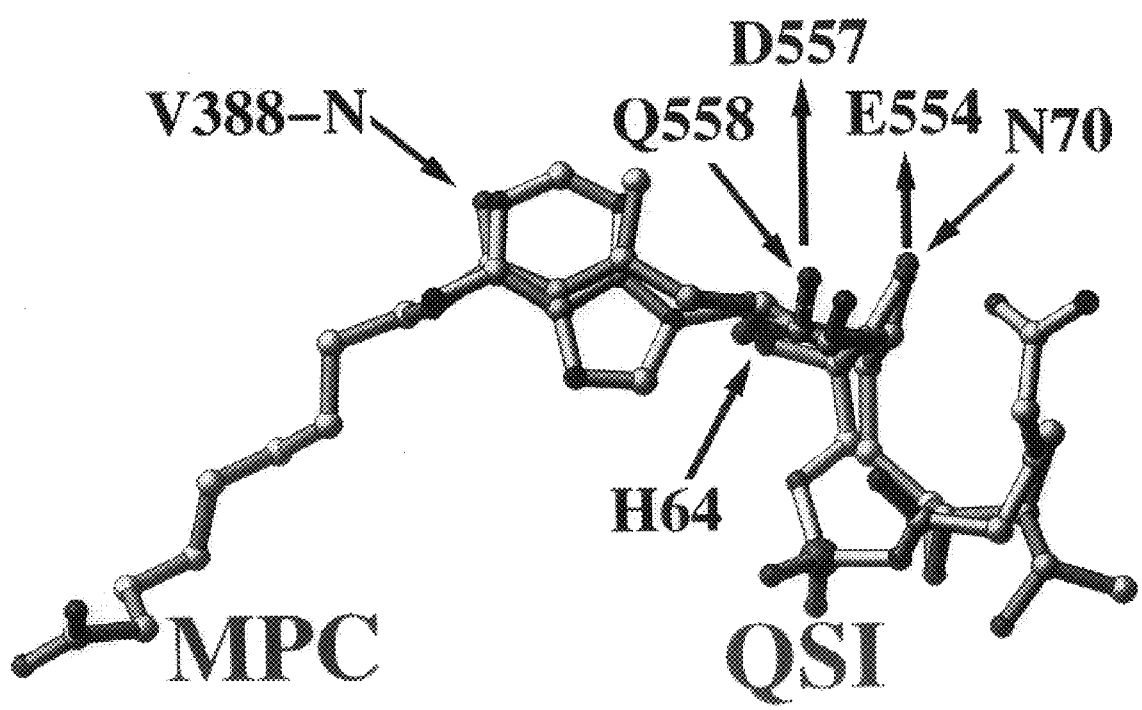

FIG. 3. A Comparison of the Binding of Mupirocin or MPC and Glutaminyl Sulfomyl Adenylate Inhibitor or QSI.

Arrows represent hydrogen bonds in the mupirocin-IRS complex, to which similar hydrogen bonds are present in QRS-QSI complex structure (Rath et al., 1998). Amino acids of the enzyme are defined elsewhere herein.

Figure 4:
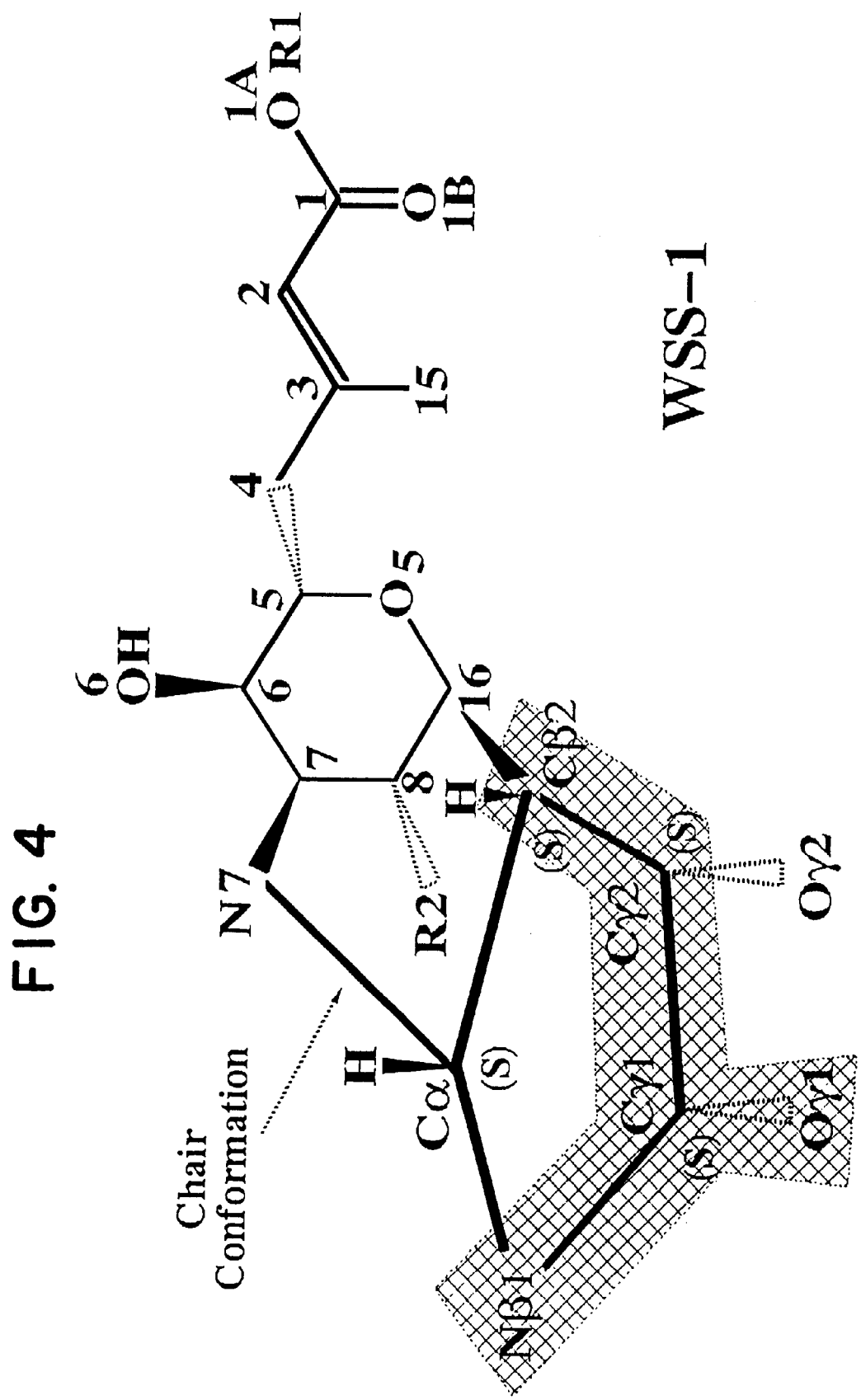

FIG. 4. The Structure and Stereochemistry of the Compound Designated as WSS-1.

WSS-1 is designed from the antibiotic, mupirocin, in three steps:

(1) An asparagine side chain moiety (shaded) is fused with one methylene linker to O7 of the mupirocin while replacing O7 with N7.

(2) Cyclization of Cβ2 to C16 and Nβ1 to Cα in a chair conformation provide a rigidity of the antibiotic.

(3) A reduction at Oγ1 double bond and an insertion Oγ2 can further provide additional interactions with MURSA IRS, but not human IRS. The head and tail of the antibiotic are the same as those in mupirocin and are abbreviated as R2 (head) and R1 (tail; carbons 1' to 9'). All newly introduced chiral centers, Cα, Cβ2, Cγ2, Cγ1, are Sisomer as indicated in parenthesis.

Figure 5:
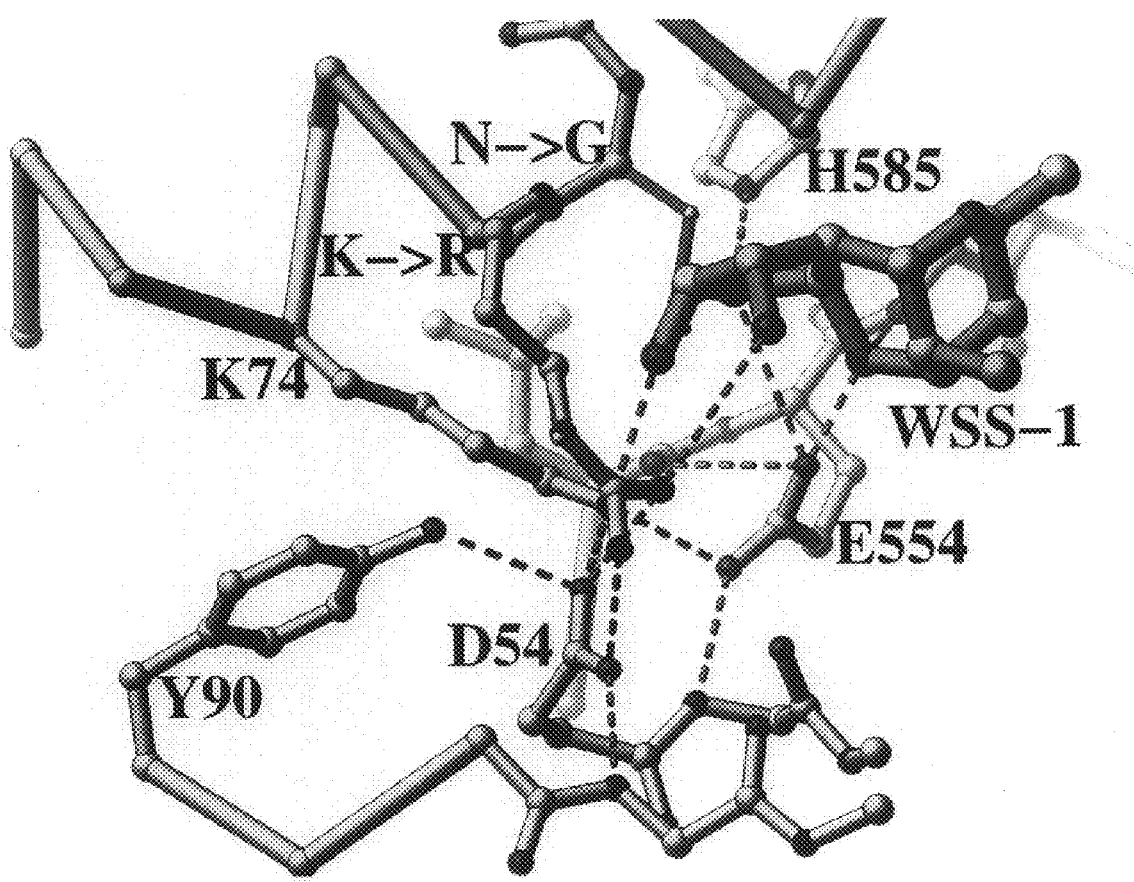

FIG. 5. A Binding Model of WSS-1 to MURSA IRS.

WSS-1 is bound to MURSA in the identical way as mupirocin (not shown) to SA IRS. SA side chains that are different from MURSA are shown. The numbering is according to SA IRS. Amino acids of the enzyme are defined elsewhere herein.

FIGS 6A–C. A List of Atomic Coordinates of WSS-1, Human IRS, and Mupirocin-Resistant *Staphylococcus Aureus* IRS that are Different from the Atomic Coordinate Corresponding to *Staphylococcus Aureus* IRS Deposited RCSB Protein Data Bank with the Accession Number PDB ID: IFFY.

Figure 7A:
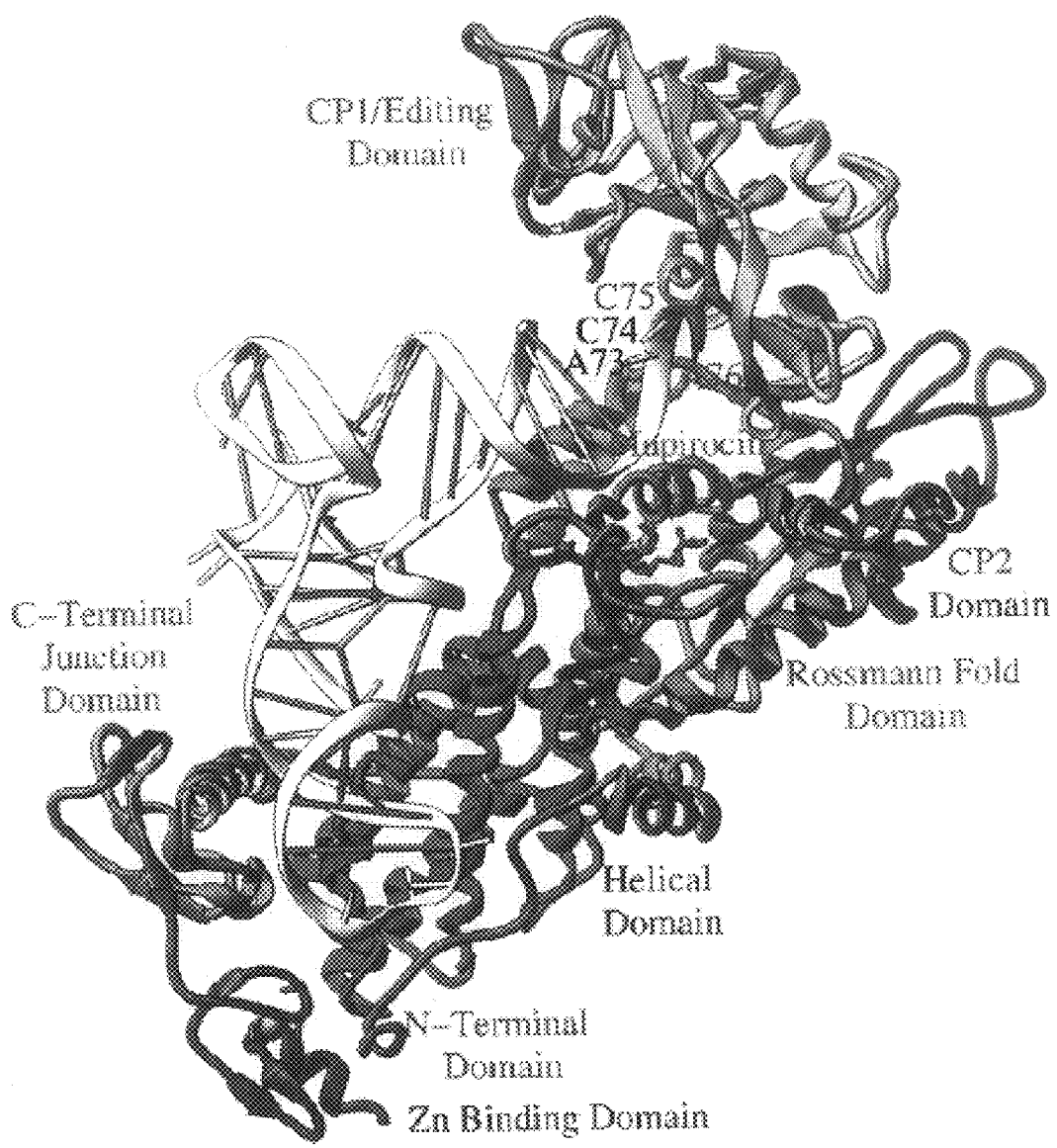
Figure 7B:
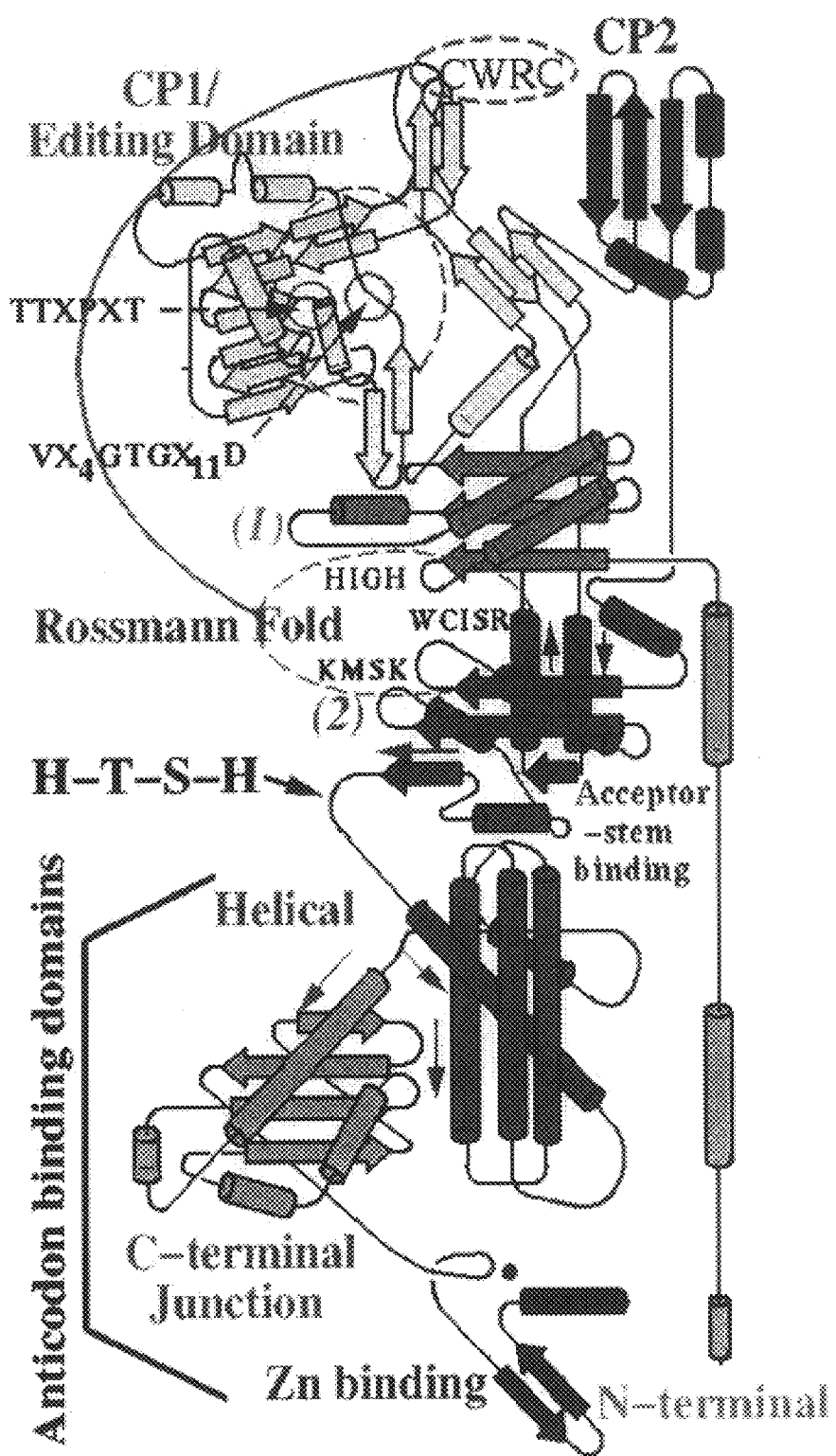
Figure 7C:
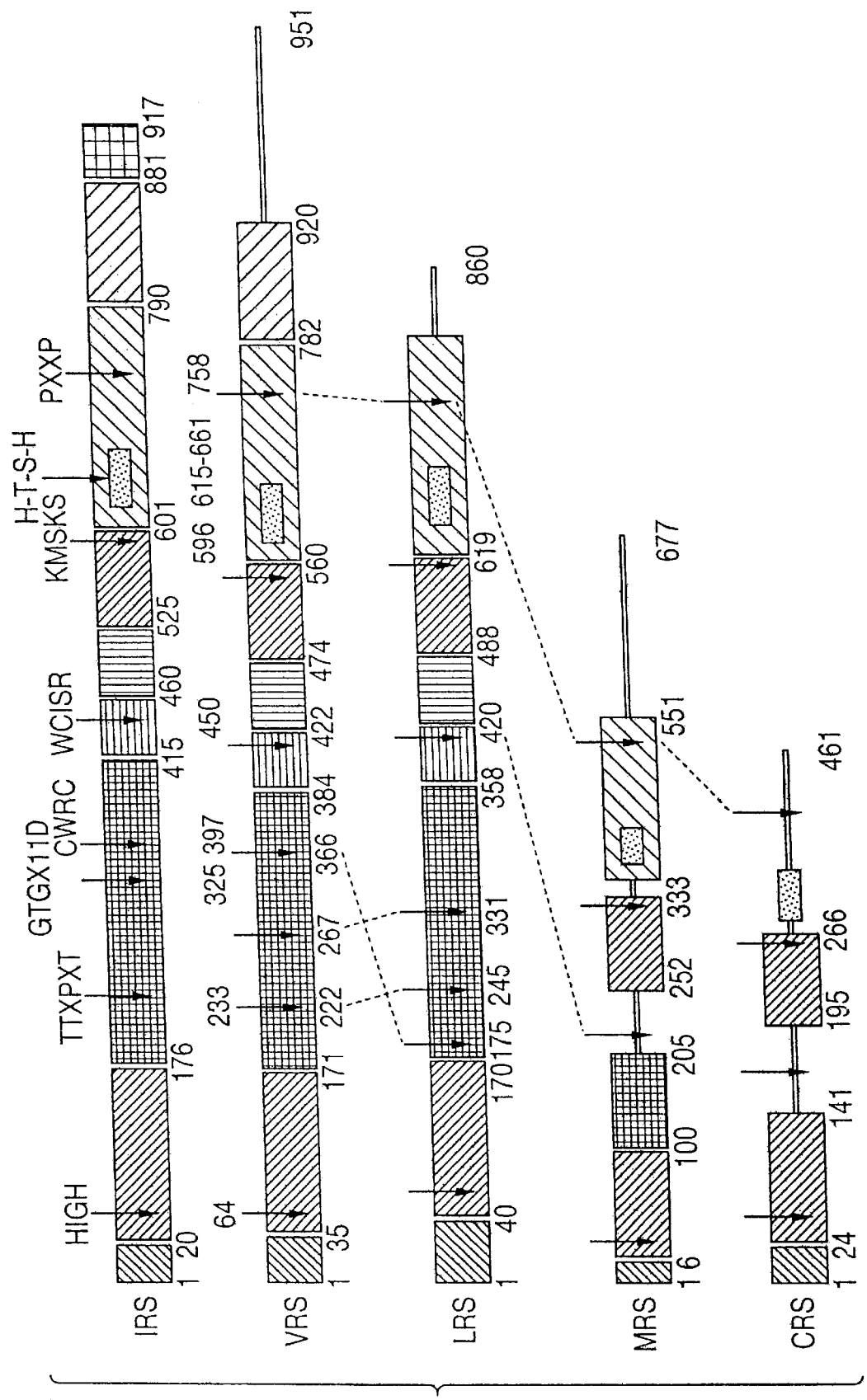

FIGS. 7A–C. An Overview of Editing tRNA Synthetases.

The seven synthetase domains are: amino terminal, dinucleotide Rossmann fold, editing, CP2, helical, C-terminal junction, and Zn-binding.

(A) A ribbons representation of isoleucyl-tRNA synthetase complexed with the tRNA. FIG. 7A shows the tRNA, two modeled nucleotides only for addressing the shuttling mechanism, mupirocin, and cysteines in the $Zn(Cys)_4$ cluster.

(B) A schematic drawing of IRS. Rossmann fold domain is showing its relationship with CP1 and CP2. The motifs of RNA binding, synthetic, and hydrolytic active sites are indicated.

(C) Linear structures of three editing tRNA synthetases (IRS, VRS, and LRS), and two other class I synthetases (MRS and CRS). Solid arrows are key motifs as shown in (B). Dashed arrows are equivalent motifs in structural environments different from previous line.

Figure 8A:
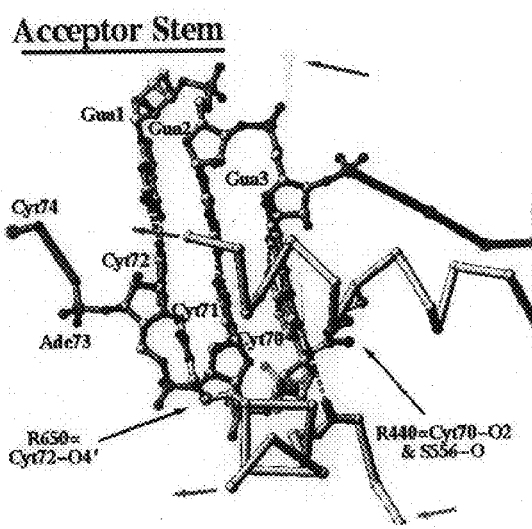
Figure 8B:
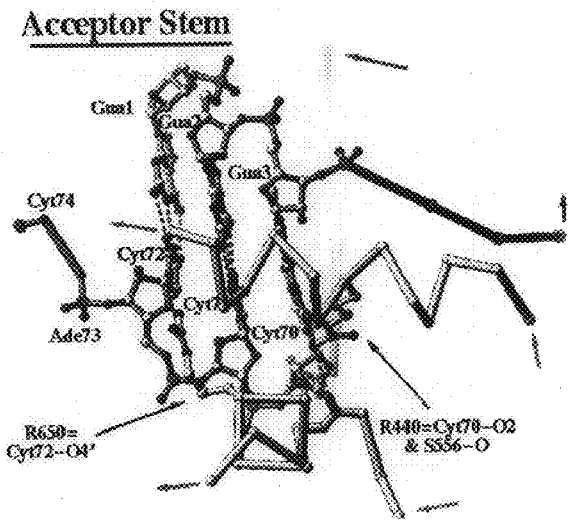
Figure 9A:
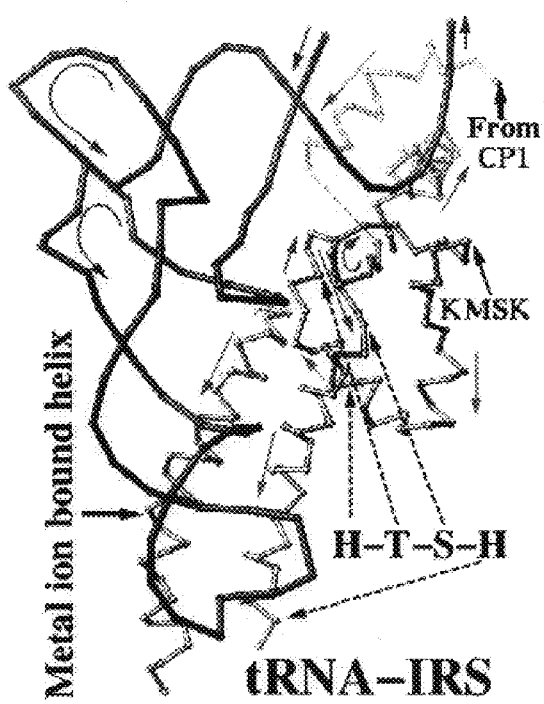
Figure 9B:
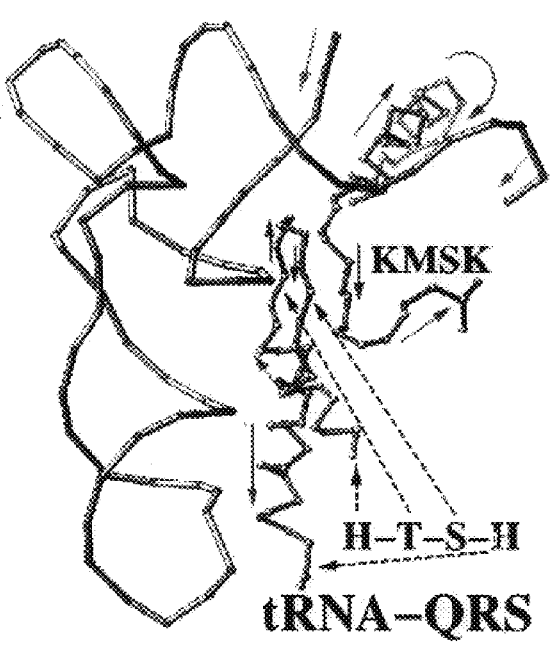
Figure 9C:
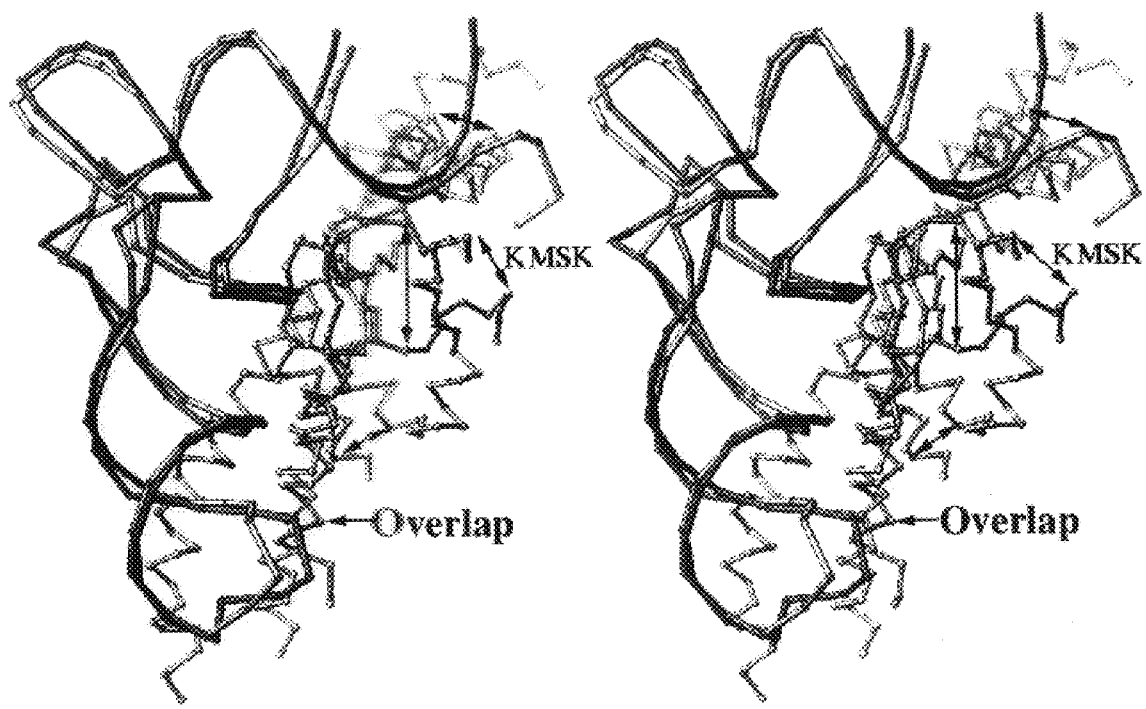
Figure 9D:
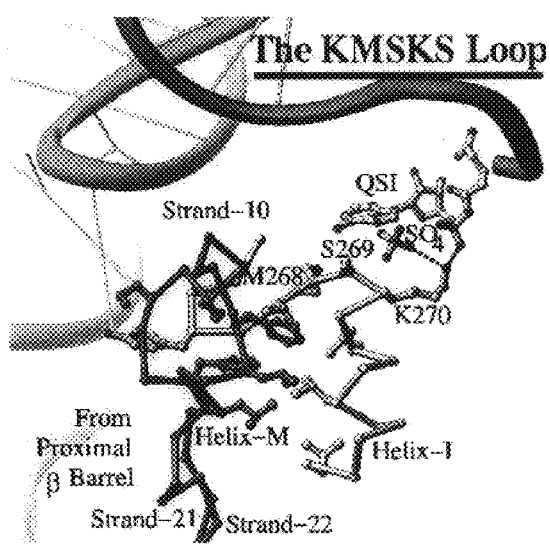
Figure 9E:
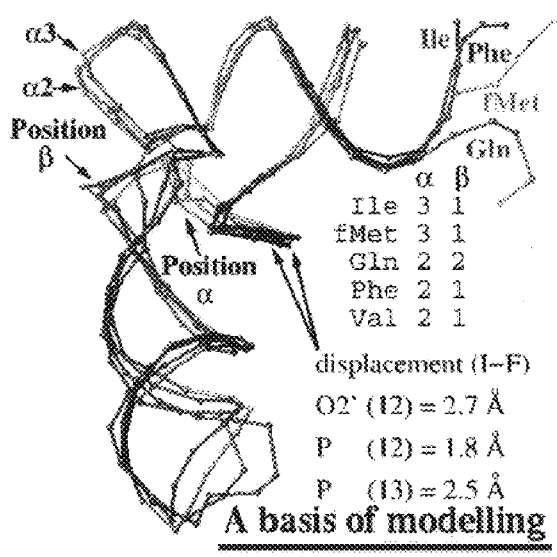

FIGS. 8A–B. A Stereodiagram of the RNA Duplex-Pairs of Synthetase α-Helices Interactions at the Acceptor Stem. Arrows indicate chain directions for tRNA and synthetase.

FIGS. 9A–E. The KMSK (SEQ ID NO: 8) Loop Switching and tRNA-RS Interactions.

(A). tRNA-IRS interactions.

(B). tRNA-QRS interactions.

(C). A stereodiagram of (A) and (B).

(D). An additional domain on the top of the KMSK (SEQ ID NO: 8) loop in non-editing tRNA synthetase, QRS.

(E). A comparison of four tRNAs of known structures provides a structural basis for modeling $tRNA^{val}$.

FIGS. 10A–F. The WCISR (SEQ ID NO: 9) and CWRC (SEQ ID NO: 10) switching.

(A). Imported $tRNA^{gln}$ and Tth IRS onto the Sau IRS-tRNA reference frame show a relationship between the CWRC (SEQ ID NO: 10) motif with the $tRNA^{gln}$ hairpin. $tRNA^{gln}$ is imported by a least squares superposition of the tRNA phosphates; Tth IRS is done by that of the Rossmann fold domains. See (F) for arrows at right.

(B). The $RX_2L$ (SEQ ID NO: 18) motif in QRS.

(C). Two R in the WCISR (SEQ ID NO: 9) motif in the inter-domain interface in Tth IRS in a resting state.

(D). A similarity of the WCISR (SEQ ID NO: 9) motifs between E. coli QRS and Sau IRS using the superposition of the two Rossmann fold domains.

(E). Two R in the WCISR (SEQ ID NO: 9) motif in Sau IRS in hydrolytic state.

(F). CWRC (SEQ ID NO: 10) motifs in three states.

FIGS. 11A–C. A $tRNA^{ile}$ releasing pathway suggests that it must first go through the error-proof checking step in the hydrolytic mode.

(A). A chimerical Sau IRS model in a "synthetic" mode with the $tRNA^{ile}$ (or/and $tRNA^{gln}$), whose CP1 domain orientation is modeled according to that in Tth IRS. C-terminal junction domain blocks the horizontal left exit; the CP1 domain blocks the up exit and an exit towards the viewer. The CP1 domain must rotate before the tRNA can be released.

(B). $tRNA^{ile}$ can be released from IRS in the hydrolytic mode in two indicated exits.

(C). $tRNA^{gln}$ can be released from QRS in the synthetic mode in three of six directions as indicated.

FIGS. 12A–G. tRNA-induced IRS switching from the resting to hydrolytic states.

(A). A rotation of 47° in the editing domain to avoid overlapping with $tRNA^{ile}$ in the phosphate-continuously, base-stacked conformation.

(B). tRNA-induced structural formation in the C-terminal junction, N-terminal, and Zn-binding domain, which are un-structured in Tth IRS. This induced-fit allows IRS to check the anticodon identity before the $tRNA^{ile}$ enters the binding site and also prevents the $tRNA^{ile}$ from leaving it once it is bound as shown in FIG. 11.

(C). An overview of the induced-fit motions.

(D). Induced-fit of the editing domain is largely a rigid-body motion, while that of the helical domain is largely a local deformation (not shown). Deformation of the editing domain at areas remote to the hydrolytic active site is due to the crystal packing.

(E–F). Two views of Tth IRS. Two active sites are located on two different sides of the enzyme.

(G). An interconnection between the two active sites in the tRNA-bound Sau IRS. Two active sites are located on a contiguous surface.

Figure 13A:
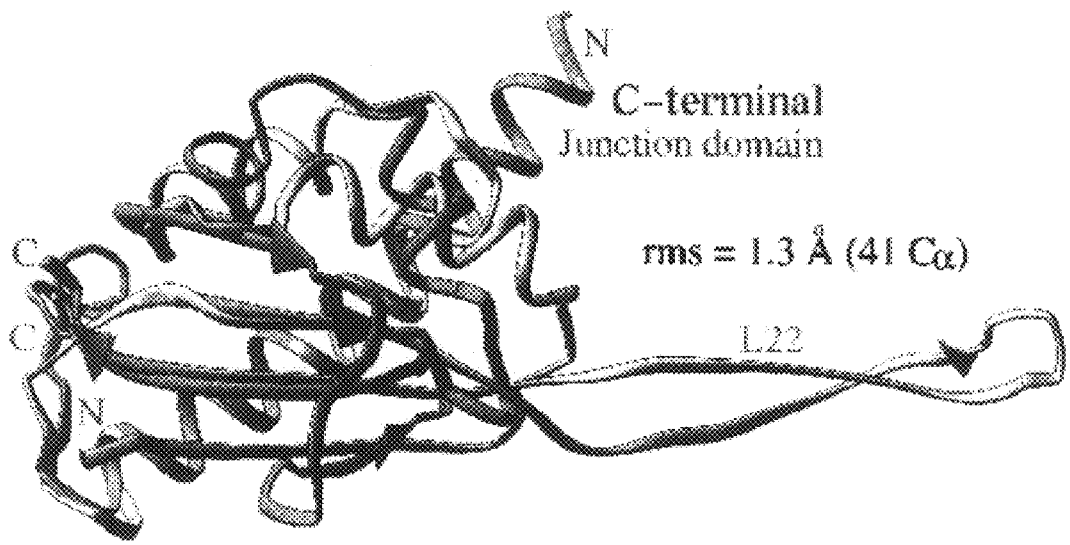
Figure 13B:
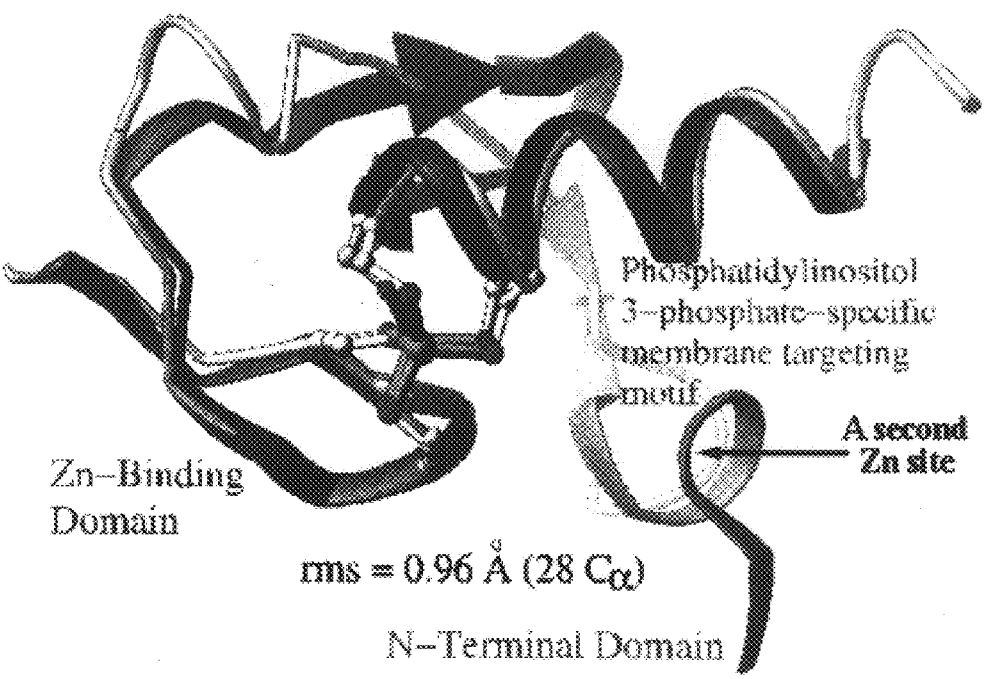

FIGS. 13A–B. An extension to the domain-swapping theory.

(A). C-terminal junction domain in IRS and ribosomal L22 share a structural similarity.

(B). The Zn binding domain in IRS and a membrane-targeting Zn-binding motif share a structural similarity. The location of a second Zn binding motif in that structure is indicated, but not shown.

DETAILED DESCRIPTION OF THE INVENTION

Abbreviations.

CP-1=Connective peptide 1 inserted into the Rossmann fold domain

CP-2=Connective peptides 2 inserted into the Rossmann fold domain

HOH=solvent molecules

IRS Isoleucyl-tRNA synthetase

LRS Leucinyl-tRNA synthetase

MM1, MM2, MM3, MM4, MM5, MM6, MM7 =metal ion complexes (Metal ions are indicated by "#" as in MM1.)

MPC=MUP=Mupirocin

MRS=Methionyl tRNA synthetase

MRSA =Methiciline resistant *Staphylococcus aureus*

MURSA =Mupirocin resistant *Staphylococcus aureus*

Psefl=Pseudomonic fluoscenes

QRS=Glutaminyl tRNA-synthetase

QSI=Glutaminyl sulfomyl adenylate analogous inhibitor

SA or Sau=*Staphylococcus aureus*

Tth=*Thermus Thermophilus.*

VRS=Valinyl tRNA-synthetase

WSS-1=WSS=The first attempt of the designed antibiotic

Amino acids:

A=Ala=Alanine

C=Cys=Cysteine

D=Asp=Aspartic acid

E=Glu=Glutamic acid

F=Phe=Phenylalanine

G=Gly=Glycine

H=His=Histidine

I=Ile=Isoleucine
K=Lys=Lysine
L=Leu=Leucine
M=Met=Methionine
N=Asn=Asparagine
P=Pro=Proline
R=Arg=Arginine
S=Ser=Serine
T=Thr=Threonine
V=Val=Valine
W=Trp=Tryptophan
X=Any of amino acids
Y=Tyr=Tyrosine
Nucleic acids:
Ade=Adenosine
Cyt=Cytidine
Gua=Guanosine
Uri=Uridine tRNA residues are in three-letters as in Gua68.
Synthetase residues are in one-letters as in G593.
Solvent molecules are labeled "W-" as in W-218.
Hydrogen bonds are in "=". For example, G593-O=Gua68-O2' reads synthetase glycine
593 backbone carbonyl making a hydrogen bond with tRNA gaunosine 68 ribose O2'.

Definitions.

As used herein, the term "atomic coordinates" or "structure coordinates" refers to mathematical coordinates derived from mathematical equations related to the patterns obtained on diffraction of a monochromatic beam of x-rays by the atoms (scattering centers) of an isoleucyl-tRNA synthetase and tRNA$^{ile}$ and mupirocin in crystal form. The diffraction data are used to calculate an electron density map of the repeating unit of the crystal. The electron density maps are used to establish the positions of the individual atoms within the unit cell of the crystal. Those of skill in the art understand that a set of structure coordinates determined by x-ray crystallography is not without standard error. For the purpose of this invention, any set of structure coordinates for isoleucyl-tRNA synthetase from any sources that have a root mean square deviation of protein backbone atoms (N, Cα, C and O) of less than 0.75 Å when superimposed using backbone atoms —(N, Cα, C and O)— on the said atomic coordinates deposited at the Research Collaboratory for Structural Bioinformatics (RCSB) Protein Data Bank (PDB) (Berman et al., 2000, Nucleic Acids Research, 28, 235–242; http://www.rcsb.org/pdb/) with the accession number PDB ID: 1FFY.

In the list of atomic coordinates deposited at the RCSB Protein Data Bank, the term "atomic coordinate" refers to the measured position of an atom in the structure in Protein Data Bank (PDB) format, including X, Y, Z and B, for each of the atoms in the amino acids and nucleotides, and in mupirocin. The assembly of "atomic coordinate" also refers to "atomic coordinates" or "structure coordinates". The term "atom type" refers to the element whose coordinates are measured. The first letter in the column defines the element. The term "X,Y,Z" refers to the crystallographically defined atomic position of the element measured with respect to the chosen crystallographic origin. The term "B" refers to a thermal factor that measures the mean displacement of the atom around its atomic center. Amino acids of the enzyme, nucleotides of the tRNA, and the antibiotic, mupirocin, solvent molecules, and metal ion complexes are defined elsewhere herein.

As used herein, the term "crystal" refers to any three-dimensional ordered array of molecules that diffracts X-rays to give spots.

As used herein, the term "complex" refers to the assembly of two or more molecules to yield a higher order structure as with IRS bound to tRNA$^{ile}$ and mupirocin.

As used herein, the term "carrier" in a composition refers to a diluent, adjuvant, excipient, or vehicle with which the product is mixed.

As used herein, the term "composition" refers to the combining of distinct elements or ingredients to form a whole. A composition comprises more than one element or ingredient. For the purposes of this invention, a composition will often, but not always, comprise a carrier.

As used herein, the term "crystallographic origin" refers to a reference point in the unit cell with respect to the crystallographic symmetry operation.

As used herein, the term "unit cell" refers to a basic parallelepiped shaped block. The entire volume of crystal may be constructed by regular assembly of such blocks. Each unit cell comprises a complete representation of the unit of pattern, the repetition of which builds up the crystal.

As used herein, the term "isoleucyl-tRNA synthetase (IRS)" refers to an enzyme that very specifically attaches the amino acid isoleucine to the 3' end of the t-RNA molecules that code for tRNA, tRNA$^{ile}$.

As used herein, the term "space group" refers to the arrangement of symmetry elements of a crystal.

As used herein, the term "symmetry operation" refers to an operation in the given space group to place the same atom in one asymmetric unit cell to another.

As used herein, the term "asymmetric unit" refers to a minimal set of atomic coordinates that can be used to generate the entire repetition in a crystal.

As used herein, the term "heavy atom derivatization" refers to the method of producing a chemically modified form, also know as "heavy atom derivatives", of crystal of the said enzyme complex. In practice, a crystal is soaked in a solution containing heavy atom metal atom salts or organometallic compounds, e.g., mercury chlorides, ethylmercury phosphate, which can diffuse through the crystal and bind to the either tRNA or the synthetase. The location (s) of the bound heavy metal atom(s) can be determined by x-ray diffraction analysis of the soaked crystal. This information, in turn, is used to generate the phase information used to construct three-dimensional structure of the complex (Blundel, T. L., and Johnson, N. L., Protein crystallography, Academic Press, 1976).

As used herein, the term "molecular modeling" refers to the use of computers to draw realistic models of what molecules look like. The methods used in molecular modeling range from molecular graphics to computational chemistry.

As used herein, the term "molecular model" refers to the three dimensional arrangement of the atoms of a molecule connected by covalent bonds.

As used herein, the term "molecular graphics" refers to 3D representations of the molecules.

As used herein, the term "computational chemistry" refers to calculations of the physical and chemical properties of the molecules.

As used herein, the term "MIR" refers to multiple isomorphous replacement, which heavy atom derivatives are prepared.

As used herein, the term "MAD" refers to multiple-wavelength anomalous dispersion method, which x-ray diffraction experiments are carried out using the tunable x-ray sources at several wavelengths. This can be used for data collection for heavy atom derivatized crystals or selenomethionine incorporated IRS crystals. This method can be used to generate the phase information.

Selenomethionine may be incorporated into wide-type or mutant IRS by expression of IRS-encoding cDNAs in autrophic *E. coli* strains. Hendrickson, W. A. et al., EMBO J., 9, pp1665–1672, (1990). Selenomethionine may also be incorporated into IRS by shutting down biosynthesis of methionine using externally supplied leucine, isoleucine and selenomethionine to the growth medium at the time of the overexpressing the IRS enzyme.

As used herein, the term "molecular replacement" refers to a method that involves generating a preliminary model of an IRS crystal whose coordinates are unknown, by orienting and positioning the said atomic coordinates described in the present invention so as best to account for the observed diffraction pattern of the unknown crystal. Phases can then be calculated from this model and combined with the observed amplitudes to give an approximate Fourier synthesis of the structure whose coordinates are unknown. (Rossmann, M. G., ed., "The Molecular Replacement Method", Gordon & Breach, New York, 1972).

As used herein, the term "homologue" refers to the said enzyme, IRS, from one source having at least 25% amino acid identity with the said enzyme or any functional domain of the said enzyme from another source. For example, *Staphylococcus aureus* IRS and human IRS are homologues because they share 26% identity; *Staphylococcus aureus* IRS and mupirocin-resistant *Staphylococcus aureus* IRS are homologues because they share 30% identity.

As used herein, the term "active site" refers to either the hydrolytic or the synthetic active sites in the said enzyme.

As used herein, the term "antibiotic binding site" refers to either active site or the mupirocin binding site.

As used herein, the term "mupirocin binding site" or "mupirocin binding cleft" refers to a binding site on IRS comprising amino acid residues adjacent to the bound mupirocin in the structure. The mupirocin binding site comprises of residues P56, P57, H64, G66, N70, E554, G555, D557, Q558, W562, H585, G586, F587, V588, M596, and S597.

As used herein, the term "naturally occurring amino acids" refers to the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamtic acid, glutamine, γ-carboxylglutamic acid, arginine, omithine, and lysine. Unless specifically indicated, all amino acids are referred to in this application are in the L-form.

As used herein, the term "unnatural amino acids" refers to amino acids that are not naturally found in proteins. For example, selenomethionine.

As used herein, the term "positively charged amino acid" includes any amino acids having a positively charged side chain under normal physiological conditions. Examples of positively charged naturally occurring amino acids are arginine, lysine, and histidine.

As used herein, the term "negatively charged amino acid" includes any amino acids having a negatively charged side chains under normal physiological conditions. Examples of negatively charged naturally occurring amino acids are aspartic acid and glutamic acid.

As used herein, the term "hydrophobic amino acid" includes any amino acids having an uncharged, nonpolar side chain that is relatively insoluble in water. Examples of naturally occurring hydrophobic amino acids are alanine, leucine, isoleucine, valine, proline, phenylalanine, tryptophan, and methionine.

As used herein, the term "hydrophilic amino acid" refers to any amino acids having an uncharged, polar side chain that is relatively soluble in water. Examples of naturally occurring hydrophilic amino acids are serine, threonine, tyrosine, asparagine, glutamine and cysteine.

As used herein, the term "hydrogen bond" refers to two hydrophilic atoms (either O or N), which share a hydrogen that is covalently bonded to only one atom, while interacting with the other.

As used herein, the term "hydrophobic interaction" refers to interactions made by two hydrophobic residues or atoms (such as C).

As used herein, the term "conjugated system" refers to more than two double bonds are adjacent to each other, in which electrons are completely delocalized with the entire system. This also includes the C2═C3 fragment of mupirocin, and aromatic residues.

As used herein, the term "aromatic residue" refers to amino acids whose side chains have a delocalized conjugated system. Examples of aromatic residues are phenylalanine, tryptophan, and tyrosine.

As used herein, the term "mutant" refers to an IRS polypeptide having at least one amino acid from the wild-type. Such a mutant may be prepared, for example, by expression of IRS cDNA previously altered in its coding sequence by oligonucleotide-directed mutagenesis. Such a mutant may also be generated by site-directed incorporation of unnatural amino acids using the general biosynthetic method of Noren, C. J., et al., Science, 244, pp 182–188 (1989). In this method, the codon encoding the amino acid of interest in wild-type IRS is replaced by "blank" nonsense codon, TAG, using oligonucleotide-directed mutagenesis. A suppressor tRNA directed against this codon is then added to an in vitro translation system to yield a mutant IRS enzyme with site-specific incorporated unnatural amino acid.

As used herein, the term "kinetic form" of IRS refers to the condition of the enzyme in its free or unbound form or bound to a chemical entity at either hydrolytic or synthetic active sites.

As used herein, the term "competitive inhibitor" refers to inhibitors by binding to the same kinetic form of IRS as its substrate(s) bind, thus directly competing with the substrate (s) for active site(s) of IRS. Competitive inhibition can be reversed completely by increasing the substrate concentration.

As used herein, the term "uncompetitve inhibitor" refers to one that inhibits IRS by binding to a different kinetic form of the enzyme than does the substrate. Such inhibitors bind to IRS with substrate and not to the free enzyme. Uncompetitive inhibition cannot be reversed completely by increasing the substrate concentration.

As used herein, the term "non-competitive inhibitor" refers to one that that can bind to either the free or substrate bound form of IRS.

Those of skill in the art may identify inhibitors as competitive, uncompetitive, or non-competitive by computer fitting enzyme kinetic data using standard equation according to Segel, I. H., Enzyme Kinetics, J. Willey & Sons, (1975). It should also be understood that uncompetitive or non-competitive inhibitors according to the present invention might bind the same or different binding site of mupirocin.

As used herein, the term "R or S-isomer" refers to two possible stereoisomers of a chiral carbon according to the Cahn-Ingold-Prelog system adopted by International Union of Pure and Applied Chemistry (IUPAC). Each group attached to the chiral carbon is first assigned to a preference or priority a, b, c, or d on the basis of the atomic number of the atom that is directly attached to the chiral carbon. The group with the highest atomic number is given the highest preference a, the group with next highest atomic number is given the next highest preference b; and so on. The group with the lowest preference (d) is then directed aways from the viewer. If the trace of a path from a to b to c is counter clockwise, the isomer is designated (S); in the opposite direction, clockwise, the isomer is designated (R).

Specific Embodiments: Binding of Mupirocin to IRS.

The present invention is based in part on the successful preparation of a crystal for the ternary complex comprising IRS/tRNA$^{ile}$/mupirocin, wherein the crystal diffracts X-ray for the determination of atomic coordinates to a resolution of 2.2 Å. The present invention provides crystals of the ternary complex and compositions comprising the crystals of the ternary complex. The present invention is also based in part on the finding that the crystal of the complex belongs to the space group $P2_12_12$ and has a large and small unit cell, wherein the large unit cell has the dimensions a=71 Å, b=100 Å, and c=186 Å and the small unit cell has the dimensions a=71 Å, b=00 Å, and c=180 Å. Moreover, the present invention is based in part on the finding that the crystal comprises an atomic structure characterized by the coordinates deposited on Jul. 26, 2000, at the Research Collaboratory for Structural Bioinformatics (RCSB) Protein Data Bank (PDB) (Berman et al., 2000, Nucleic Acids Research, 28, 235–242; http://www.rcsb.org/pdb/) with the accession number PDB ID: 1FFY.

The present invention is also based in part on the use of the atomic coordinates of the crystal of the IRS/tRNA$^{ile}$/mupirocin complex to obtain a novel compound WSS-1. The present invention provides the structure of the compound (FIG. 4) and provides compositions comprising the compound.

1. The Structure and Stereochemistry of Mupirocin in the Cocrystal Structure

Figure 1:
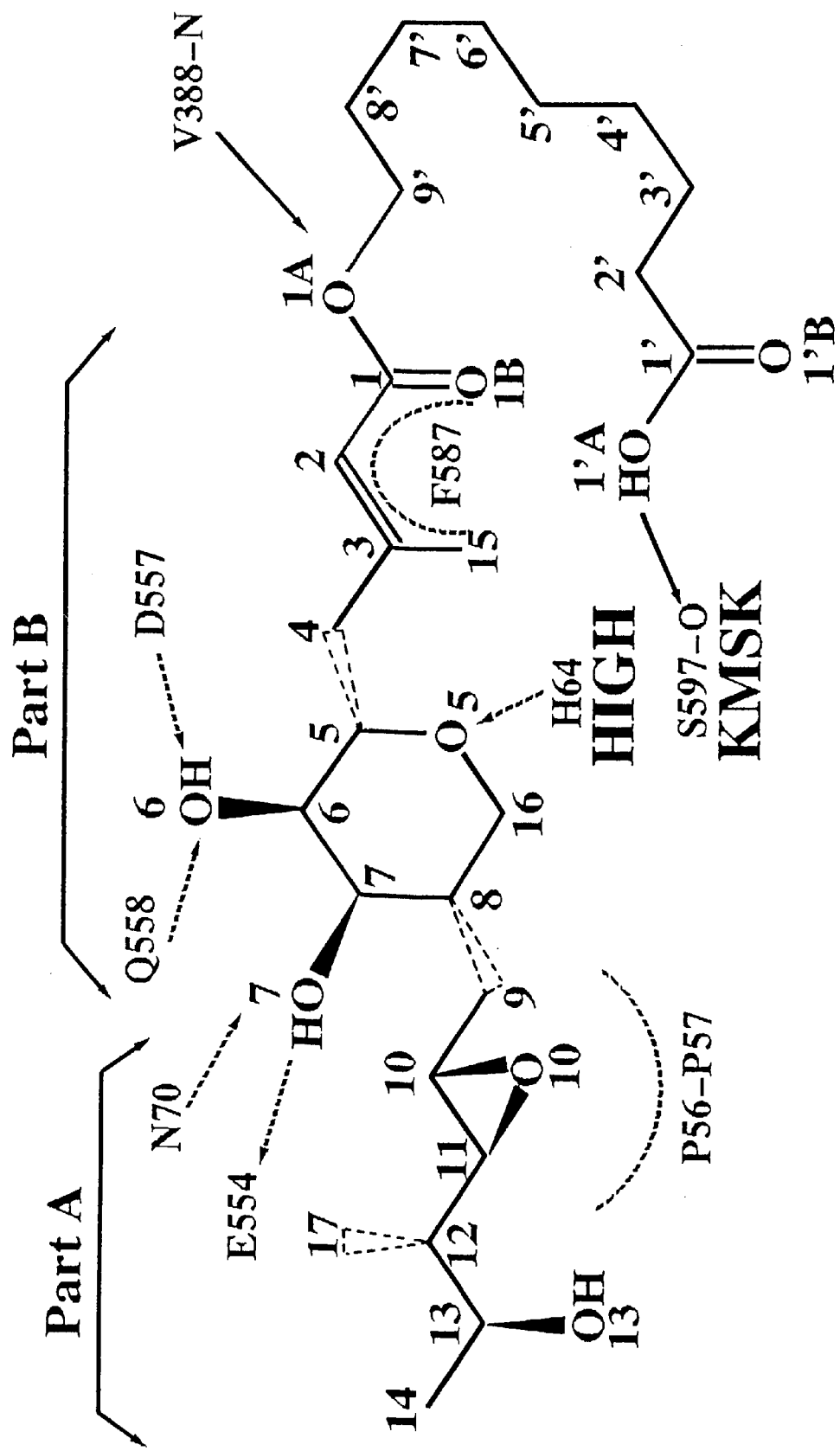
FIG. 1. The Structure and Stereochemistry of Mupirocin Bound to IRS in the Cocrystal Structure.

The structure and stereochemistry of mupirocin bound in the cocrystal is shown in FIG. 1. Mupirocin has a simple chemical composition, $C_{26}H_{45}O_9$. Its functional groups bound to its target enzyme, IRS, are oxygen atoms and unsaturated C=C bonds in three parts of the antibiotic. Mupirocin is an acetylated form of monic acid by a 9-carbon fatty acid, and monic acid has two parts A and B (FIG. 1). Its head group (or Part A) resembles isoleucine and the central portion (or Part B) resembles an adenylate, as described below. In the early stage of structure determination, mupirocin was built according to experimental electron density maps in an incorrect stereochemistry (Silvian et al., 1999). In the late stage of refinement, a simulated-annealing (SA) omitted electron density map clearly shows that mupirocin in the cocrystal has the same stereochemistry (or stereoisomer) as mupirocin by itself (Chain et al., 1977, Alexander et al., 1978). The misinterpretation of the mupirocin structure in the early stage was due to the poor quality of electron density maps. The SA-omitted map also clearly shows that (1) the definition of the C2–C3 fragment separated from a stacking phenylalanine side chain and (2) the location of O1'A and O1'B (FIG. 1). Both of these features are not present in the original experimental maps.

The present invention provides the correct atomic structure for the crystal of the IRS/tRNA$^{ile}$/mupirocin complex. The atomic coordinates of the crystal structure are deposited on Jul. 26, 2000 at the RCSB Protein Data Bank with the accession number PDB ID: 1FFY.

2. Hydrogen Bonds Between Mupirocin and IRS

Six of the nine oxygen atoms in mupirocin form hydrogen bonds with isoleucyl-tRNA synthetase in the cocrystal structure (FIG. 2). There are three oxygens present in the central portion of the antibiotic in the 6-membered ring, O6, O7, and O5. Both O6 and O7 in mupirocin in the correct stereochemistry (FIG. 2) are recognized by two side chains of one acid group and one amine group, O6 by D557 and Q558, and O7 by E554 and N70, in addition to sharing a backbone amine, G555. The third oxygen, O5 is recognized by H64 (FIG. 2). As described below, this portion of the antibiotic resembles the ribose of ATP or ATP analogue. At its head, O10 interacts with a backbone amine (P57) and a backbone carbonyl (P56) (FIG. 2); and O13, however, is fully exposed. We will show below that indeed the head group resembles the side chain of isoleucine as it has been long suspected (Yanagisawa et al., 1994, Hughes and Mellows, 1978). Therefore, it is not surprising that O13, inserted at a position equivalent to the isoleucine side chain Cγ1, does not contribute to the binding of the antibiotic through any hydrogen bonds. Removal of this oxygen from mupirocin should not affect its affinity to IRS. On the other hand, this group may serve as a linker for more complex antibiotic design as described below. At its tail, one of two completely equivalent hydroxyls is hydrogen bonded to the backbone of the KMSKS (SEQ ID NO: 6) loop. At the central portion of mupirocin, O1B of the carbonyl of the monic acid part in mupirocin receives a hydrogen from the V388 backbone amide for a hydrogen bond. As shown below, the functional group of O1B in this antibiotic occupies precisely where N1 of the ATP's adenosine ring. This strictly requires a hydrogen acceptor at this position, which is also known as low-energy unoccupied molecular orbital defined by synthetic and theoretical chemists (Brown et al., 1997). O1A in ester bond in mupirocin is not involved in any recognition by the synthetase, but it is partially buried and in a situation different from O13 at its head.

3. Hydrophobic Interactions Between Mupirocin and IRS

Both the head and tail of the monic acid portion of mupirocin are directly in contact with isoleucyl-tRNA synthetase. The binding site in IRS for mupirocin is located in a deep cleft, made of three nearly invariant regions of the DGPPYANGX$_2$"HIGH" (SEQ ID NO: 13), GFX$_2$DX$_2$GX"KMSKS" (SEQ ID NO: 14), and EGDQXRGWF (SEQ ID NO: 15) motifs (FIG. 2). Despite of at least four unoccupied pockets near the antibiotic binding site, the following groups and atoms are well packed inside the binding cleft: the conjugate system (of O1A, O1B, C1 to C4 and C15), C14 and C17 (of isoleucine side chain equivalent), and the part of C5' through C8', as judged by ray lengths of the occluded surface. The conjugate system is packed between F587 and H64 of the helix of the HIGH (SEQ ID NO: 15) motif. This interaction explains why any expansion of the C1–C3 system such as reduction of the C2=C3 double bound reduced the binding activity to IRS (Walker et al., 1993, Crimmin et al., 1989ab), while cyclization at the position remains active as long as the conjugated system can accept a hydrogen at position O1B. An ability of accepting a hydrogen at this position is the determinant of the antibiotic function. This is different from the previously proposed theory of electrostatic potential of the system (Brown et al., 1997).

The packing cleft of the branching methyl group C17 is made of the side chain carbon atoms of E554 and Q558 (FIG. 2), and the packing cleft of C14 is made of the P56 ring (FIG. 2) and a portion of the W562 side chain. The configuration of C11 (equivalent to Cα of isoleucine, see below), C12 (Cβ), C13 (Cγ1), C14 (Cδ1), and C17 (Cγ2) is equivalent to the third most populated rotamer conformation in the database (Ponder and Richards, 1987). It is possible that the presence of O13 in the antibiotic may stabilize this rotamer conformation over others.

The motion of the KMSK (SEQ ID NO: 8) loop in class I tRNA synthetase directly controls the accessibility of amino adenylates as described elsewhere. Different from non-editing class I synthetases, three editing enzymes allow the tRNA to directly bind the KMSK (SEQ ID NO: 8) loop and displace the loop over 10–15 Å, due to a missing domain on the top of the KMSKS (SEQ ID NO: 6) loop. This motion carries the synthetic products of both amino adenylates and post-transfer amino acids out of the synthetic active site while the KMSK (SEQ ID NO: 8) loop remains to be likely bound to the α-phosphate equivalent atom. This is how tRNA facilitates the shuttling mechanism from the synthetic to hydrolytic active sites (Silvian et al., 1999).

Due to the large amplitude of motion, simple nonhydrolyzable amino adenylate analogue inhibitors are not often very effective in inhibiting aminoacylation in editing tRNA synthetases, while they are in non-editing tRNA synthetases. Large conformational changes in IRS have previously been suggested on the highly positive entropy activation and effects of Hofmeister anions on Km and Kcat (Loftfield et al., 1980). The shuttling mechanism may operate independently with rate-limiting steps of the amino acylation reactions, since there are no apparent consensus as to which step is the rate-limiting step among the three IRS enzymes from three different strains of E. coli (Fersht and Kaethner, 1976, Yarus and Berg, 1969, Eldred and Schimmel, 1972, Lovgren et al., 1976).

The long hydrophobic tail of the antibiotic mupirocin is essential for its function. The tail is locked into the position in a hydrogen bond with the KMSK (SEQ ID NO: 8) backbone (FIG. 2), and its C5' through C8' become tightly fitted into the cleft. The cleft comprises the side chains of H64 (FIG. 2), M65, and M596 (not shown). There could also be a synergetic binding between the C5'–C8' and the conjugated system C1–C3; the binding of the tail enhances the interactions at the C1–C3 fragment. The monic acid portion of the antibiotic extends over 14 Å, and the hydrophobic tail extends over 10 Å with the entire antibiotic over 20 Å.

In the absence of the long tail, monic acid behaves like valine-adenylate and will be constantly shuttled out by the KMSKS (SEQ ID NO: 6) loop in an attempt to be hydrolyzed by IRS. This is how the metabolic degradation of mupirocin leads the inactivation of the antibiotic when it is converted to monic acid (Mellows, 1989). The long tail of the fatty acid may also be an advantage for the antibiotic in membrane permeability. The cocrystal structure shows that near the antibiotic binding cleft, there are at least four more unoccupied pockets that can be used for re-designing the antibiotic. If each contribution is additive, a tighter inhibitor can be found through the structure based drug re-design approach. An approach in drug re-design near one pocket is discussed below. In this re-design, the focus is on the selectivity of the MURSA over human enzymes.

4. Mupirocin is an Isoleucine Adenylate Analogue

The monic acid portion of mupirocin is a nonhydrolyzable isoleucine adenylate analogue inhibitor (FIG. 3). The central portion has four functional oxygen groups, O6, O7, O5 and O1B. They are all recognized by IRS. Similar functional groups are also recognized in nonhydrolyzable glutamine adenylate analogous inhibitor (QSI) by glutaminyl-tRNA synthetase, QRS (Rath et al., 1998). They are O2' of QSI by T230 of QRS, O4' by H43 (if the H43 ring is allowed to flip over), N1 by the L261 backbone carbonyl, in addition to N6 by R260. O3' in QSI is bound to its own glutamine side chain.

When we superimpose their Rossmann fold domains, it is evident that (1) N1 of QSI receiving a hydrogen from the L261 backbone amide in QRS is equivalent to O1B of mupirocin receiving a hydrogen from the V388 backbone amide in IRS; (2) a hydrogen between H43 in QRS and O4 of QSI is equivalent to one between H64 in IRS and O5 of mupirocin; (3) a hydrogen bond between T230 in QRS and O2 of QSI is equivalent to one between N70 in IRS and O6 of mupirocin; and (4) a hydrogen bond between its own glutamine and O3' of QSI is equivalent to one between D557 in IRS and O7 of mupirocin in IRS. Indeed, these functional group atoms can be completely superimposed in the two inhibitors (FIG. 3). Such a superposition clearly leads to the following two conclusions: the conjugated systems in two inhibitors also overlay on the top of each other, and the amino acid side chains are located next to each other, even though in both cases they do not resemble each other at all.

5. Uses of the Atomic Coordinates of the IRS/tRNA$^{ile}$/Mupirocin Complex

Molecular modeling involves the use of computers to draw realistic models of what molecules look like. The methods utilized in molecular modeling range from molecular graphics (i.e., 3 D representations) to computational chemistry (i.e., calculations of the physical and chemical properties).

Using molecular modeling, rational drug design programs can look at a range of different molecular structures of drugs that may fit into the active site of an enzyme, and by moving them on the computer screen it can be decided which structures actually fit the site well (William Bains, Biotechnology from A to Z, second edition, 1998, Oxford University Press, page 259).

For basic information on molecular modeling, see, for example, M. Schlecht, Molecular Modeling on the PC, 1998, John Wiley & Sons; Gans et al., Fundamental Principals of Molecular Modeling, 1996, Plenum Pub. Corp.; N. C. Cohen (editor), Guidebook on Molecular Modeling in Drug Design, 1996, Academic Press; and W. B. Smith, Introduction to Theoretical Organic Chemistry and Molecular Modeling, 1996. U.S. Patents which provide detailed information on molecular modeling include U.S. Pat. Nos. 6,093,573; 6,080,576; 5,612,894; 5,583,973; 5,030,103; 4,906,122; and 4,812,12, each of which are incorporated by reference in their entirety.

The present invention permits the use of molecular and computer modeling techniques to design, and select compounds, such as antibiotics or other therapeutic agents, that interact with IRS and inhibit protein synthesis. The invention enables the use of atomic coordinates deposited at the RCSB Protein Data Bank with the accession number PDB ID: 1FFY for the IRS/tRNA$^{ile}$/mupirocin complex to design compounds that interact with IRS. For example, this invention enables the design of compounds that act as competitive inhibitors of IRS by binding to, all or a portion of, the active site involved in protein synthesis.

This invention also enables the design of compounds that act as uncompetitive inhibitors of IRS. These inhibitors may bind to, all or a portion of, the active site of IRS already bound to its tRNA$^{ile}$ and may be more potent and less non-specific than known competitive inhibitors that compete for IRS active site. Similarly, non-competitive inhibitors that bind to and inhibit IRS whether or not it is bound to another chemical entity may be designed using the atomic coordinates of IRS of this invention. Alternatively, the atomic coordinates provided by the present invention is useful to design improved analogues of known IRS protein synthesis inhibitors or to design novel classes of inhibitors based on the IRS/tRNA$^{ile}$/muciprocin co-complex. This provides a novel route for designing IRS inhibitors with both high specificity and stability.

The atomic coordinates of the present invention also enables probing an IRS crystal with molecules composed of a variety of different chemical entities to determine optimal sites for interaction between candidate IRS inhibitors and IRS. For example, high resolution X-ray diffraction data collected from crystals saturated with solvent allows the determination of where each type of solvent molecule sticks. Small molecules that bind tightly to those sites can then be designed and synthesized and tested for their IRS inhibitor activity (Travis, J., Science, 262, p. 1374 (1993)).

Moreover, the present invention enables screening computationally small molecule databases for chemical entities, agents, or compounds that can bind in whole, or in part, to IRS. In this screening, the quality of fit of such entities or compounds to the binding site may be judged either by shape complementarity or by estimated interaction energy (Meng, E. C. et al., J. Coma. Chem., 13, pp. 505–524 (1992)).

The design of compounds that bind to or inhibit IRS according to this invention generally involves consideration of two factors. First, the compound must be capable of physically and structurally associating with IRS. Non-covalent molecular interactions important in the association of IRS with the compound, include hydrogen bonding, van der Waals and hydrophobic interactions. Second, the compound must be able to assume a conformation that allows it to associate with IRS. Although certain portions of the compound will not directly participate in this association with IRS, those portions may still influence the overall conformation of the molecule. This, in turn, may have a significant impact on potency. Such conformational requirements include the overall three-dimensional structure and orientation of the chemical entity or compound in relation to all or a portion of the active site of IRS, or the spacing between functional groups of a compound comprising several chemical entities that directly interact with IRS.

The potential inhibitory or binding effect of a chemical compound on IRS may be analyzed prior to its actual synthesis and testing by the use of computer modeling techniques. If the theoretical structure of the given compound suggests insufficient interaction and association between it and IRS, synthesis and testing of the compound is obviated. However, if computer modeling indicates a strong interaction, the molecule may then be synthesized and tested for its ability to interact with IRS and inhibit protein synthesis. In this manner, synthesis of inoperative compounds may be avoided.

One skilled in the art may use one of several methods to screen chemical entities fragments, compounds, or agents for their ability to associate with IRS and more particularly with the individual binding pockets of the IRS active site or accessory binding site. This process may begin by visual inspection of, for example, the active site on the computer screen based on the IRS coordinates deposited in the RCSB Protein Data Bank with the accession number PDB ID: 1FFY. Selected chemical entities, compounds, or agents may then be positioned in a variety of orientations, or docked, within an individual binding pocket of IRS as defined supra. Docking may be accomplished using software such as Quanta and Sybyl, followed by energy minimization and molecular dynamics with standard molecular mechanics forcefields, such as CHARMM and AMBER.

Specialized computer programs may also assist in the process of selecting chemical entities. These include but are not limited to:

1. GRID (Goodford, P. J., "A Computational Procedure for Determining Energetically Favorable Binding Sites on Biologically Important Macromolecules" J. Med. Chem., 28, pp. 849–857 (1985)). GRID is available from Oxford University, Oxford, UK.
2. MCSS (Miranker, A. and M. Karplus, "Functionality Maps of Binding Sites: A Multiple Copy Simultaneous Search Method." Proteins: Structure, Function and Genetics, 11, pp. 29–34 (1991)). MCSS is available from Molecular Simulations, Burlington, Mass.
3. AUTODOCK (Goodsell, D. S. and A. J. Olsen, "Automated Docking of Substrates to Proteins by Simulated Annealing" Proteins: Structure. Function, and Genetics, 8, pp. 195–202 (1990)). AUTODOCK is available from Scripps Research Institute, La Jolla, Calif.
4. DOCK (Kuntz, I. D. et al., "A Geometric Approach to Macromolecule-Ligand Interactions" J. Mol. Biol., 161, pp. 269–288 (1982)). DOCK is available from University of California, San Francisco, Calif.

Once suitable chemical entities, compounds, or agents have been selected, they can be assembled into a single compound or inhibitor. Assembly may proceed by visual inspection of the relationship of the fragments to each other on the three-dimensional image displayed on a computer screen in relation to the atomic coordinates of IRS. This would be followed by manual model building using software such as Quanta or Sybyl.

Useful programs to aid one of skill in the art in connecting the individual chemical entities, compounds, or agents include but are not limited to:

1. CAVEAT (Bartlett, P. A. et al, "CAVEAT: A Program to Facilitate the Structure-Derived Design of Biologically Active Molecules". In Molecular Recognition in Chemical and Biological Problems", Special Pub., Royal Chem. Soc., 78, pp. 82–196 (1989)). CAVEAT is available from the University of California, Berkeley, Calif.
2. 3D Database systems such as MACCS-3D (MDL Information Systems, San Leandro, Calif.). This area is reviewed in Martin, Y. C., "3D Database Searching in Drug Design", J. Med. Chem., 35, pp. 2145–2154 (1992).
3. HOOK (available from Molecular Simulations, Burlington, Mass.).

Instead of proceeding to build an IRS inhibitor in a step-wise fashion one chemical entity at a time as described above, inhibitory or other IRS binding compounds may be designed as a whole or "de novo" using either an empty active site or optionally including some portion(s) of known inhibitor(s). These methods include:

1. LUDI (Bohm, H.-J., "The Computer Program LUDI: A New Method for the De Novo Design of Enzyme Inhibitors", J. ComR. Aid. Molec. Design, 6, pp. 61–78 (1992)). LUDI is available from Biosym Technologies, San Diego, Calif.
2. LEGEND (Nishibata, Y. and A. Itai, Tetrahedron, 47, p. 8985 (1991)). LEGEND is available from Molecular Simulations, Burlington, Mass.
3. LeapFrog (available from Tripos Associates, St. Louis, Mo.).

Other molecular modeling techniques may also be employed in accordance with this invention. See, e.g., Cohen, N. C. et al., "Molecular Modeling Software and Methods for Medicinal Chemistry, J. Med. Chem., 33, pp. 883–894 (1990). See also, Navia, M. A. and M. A. Murcko, "The Use of Structural Information in Drug Design", Current Opinions in Structural Biology, 2, pp. 202–210(1992).

Once a compound has been designed or selected by the above methods, the efficiency with which that compound may bind to IRS may be tested and optimized by computational evaluation. An effective IRS protein synthesis inhibitor must preferably demonstrate a relatively small difference in energy between its bound and free states (i.e., a small deformation energy of binding). Thus, the most efficient IRS inhibitors should preferably be designed with a deformation energy of binding of not greater than about 10 kcal/mole, preferably, not greater than 7 kcal/mole. IRS inhibitors may interact with the enzyme in more than one conformation that is similar in overall binding energy. In those cases, the deformation energy of binding is taken to be the difference between the energy of the free compound and the average energy of the conformations observed when the inhibitor binds to the IRS.

A compound designed or selected as binding to IRS may be further computationally optimized so that in its bound state it would preferably lack repulsive electrostatic interaction with the target enzyme. Such non-complementary (e.g., electrostatic) interactions include repulsive charge-charge, dipole-dipole and chargedipole interactions. Specifically, the sum of all electrostatic interactions between the inhibitor and the enzyme when the inhibitor is bound to IRS, preferably make a neutral or favorable contribution to the enthalpy of binding.

Specific computer software is available in the art to evaluate compound deformation energy and electrostatic interaction. Examples of programs designed for such uses include: Gaussian 92, revision C [M. J. Frisch, Gaussian, Inc., Pittsburgh, Pa., COPYRGT.1992]; AMBER, version 4.0 [P. A. Kollman, University of California at San Francisco, .COPYRGT.1994]; QUANTA/CHARMM [Molecular Simulations, Inc., Burlington, Mass. .COPYRGT. 1994]; and Insight II/Discover (Biosysm Technologies Inc., San Diego, Calif. .COPYRGT.1994). These programs may be implemented, for instance, using a Silicon Graphics workstation, IRIS 4D/35 or IBM RISC/6000 workstation model 550. Other hardware systems and software packages will be known to those skilled in the art.

Once an IRS protein synthesis inhibitor or any compound that associates with IRS has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to IRS by the same computer methods described in detail, above.

The present invention further provides a method of obtaining new compounds and agents that interact with IRS from procaryotes and eucaryotes. IRS from procaryotes and eucaryotes are structurally conserved. The amino acid sequences of the IRS enzymes from procaryotes and eucaryotes can be aligned due to the evolutionary conservation of the identity of amino acid residues that are important for 3-D structure, the nature and shape of the binding sites for substrates (tRNA$^{ile}$, ATP and Ile) and the catalytic site. This similarity in amino acid sequence of the homologous enzymes allows the construction of approximate models for the homologues whose crystal structures have not been solved, so-called homology modeling.

The present invention also provides new compounds and agents that interact with IRS and compositions comprising the new compounds or agents and carriers.

The compounds designed by the above methods are useful for inhibiting protein synthesis and therefore are useful as therapeutic agents to treat and prevent diseases or conditions associated with protein synthesis.

6. Structure Conservation of IRS from Different Species

Aminoacyl-tRNA synthetases have been classified as either group I or group II synthetases based on their sequence similarity and crystallographic structure. Group I aminoacyl-tRNA synthetase all share two consensus amino acid motifs "HIGH" (His-Ile-Gly-His, SEQ ID NO: 5) and "KMSKS" (Lys-Met-Ser-Lys-Ser, SEQ ID NO: 6), while group II synthetases lack these motifs but have a third consensus region "GLER" (Gly-Leu-Glu-Arg, SEQ ID NO: 7). The HIGH (SEQ ID NO: 5) tetrapeptide and the KMSKS (SEQ ID NO: 6) pentapeptide contribute to the structure of the ATP binding site in all class I synthetase. Based on its structure, IRS has been classified as a group I synthetase.

Nagel et al. (1991, Proc. Natl. Acad. Sci. USA, 88, 8121–8125) report that all aminoacyl-tRNA synthetases within a specific group (I or II) are structurally related. After examining the region between the HIGH (SEQ ID NO: 5) and KMSKS (SEQ ID NO: 6) motifs (~1600 bp in length) of IRS genes of several lower eucaryotes, bacteria, and archaea, Brown et al. (1995, Proc. Natl. Acad. Sci. USA, 92, 2441–2445) report that the region between the HIGH (SEQ ID NO: 5) and KMSKS (SEQ ID NO: 6) motifs is the most conserved region both within and between different types of group I aminoacyl-tRNA synthetases. Hong et al. (1995, Microbiology, 141, 2561–2567) disclose isolation of the IRS gene from *C. jejuni* and report alignment of the *C. jejuni* IRS sequence with six other bacterial IRS sequence and two other lower eucaryotic IRS sequences identified seven conserved motifs including the signature sequences, HIGH (SEQ ID NO: 5) and KMSKS (SEQ ID NO: 6)of class I aminoacyl-tRNA synthetases.

As discussed earlier, Nureki et al. (1998) provide the crystal structure of *Thermus thermophilus* IRS complexed with L-isoleucine or L-valine. Nureki et al. (1998) teach that the ATP binding domain of group I synthetases is constructed with a Rossmann fold. Nureki et al. (1998) show that the Rossmann-fold domain of the IRS of *Thermus thermophilus* has a central deep catalytic cleft with two characteristic ATP-binding motifs, His$^{54}$-Val$^{55}$-Gly$^{56}$-His$^{57}$- (SEQ ID NO: 20) and Lys$^{591}$-Met$^{592}$-Ser$^{593}$-Lys$^{594}$ (SEQ ID NO: 8) on its lower level. In the L-isoleucine/IRS complex, one L-isoleucine molecule is bound at the bottom of the catalytic cleft. The hydrophobic side chain of Lisoleucine is recognized by a pocket consisting of Pro$^{46}$, Trp$^{518}$, and Trp$^{558}$ through van der Waals interactions. Residues Asp$^{85}$ and Gln$^{554}$ form hydrogen bonds with $NH_3^+$ and $COO^-$ groups respectively. According to Nureki et al. (1998), these residues are completely conserved among the 17 IRS cloned thus far.

Clearly, IRS is structurally conserved among the different species. Accordingly, it is within the skill of the artisan to use the atomic coordinates of the *S. aureus* IRS/tRNA$^{ile}$/ muciprocin to obtain new agents that interact with IRS from other species.

7. Use of Homology Structure Modeling to Design Molecules (Ligands) that will Bind More Tightly to the Target Enzyme than to the Non-Target Enzyme The present invention contemplates the use of the structure of isoleucyl-tRNA synthetase complexed with tRNA and mupirocin to designing modifications to starting compounds, such as mupirocin, that will bind more tightly to the target enzyme (e.g., the IRS of *S. aureus*) and less tightly to the non-targeted enzyme (e.g., human IRS).

The structure of a complex between the enzyme and the starting compound (e.g., mupirocin) can also be used to guide the modification of that compound to produce new compounds that have other desirable pharmaceutical properties, such as chemical stability, solubility or membrane permeability.

Starting with the structure of the enzyme from the organism we targeted (*S. aureus*, for example), the structure of the enzymes from the non-targeted organism (for example, the human enzyme) can be constructed by changing the structure of protein residues at the binding site for a ligand to the residues of the non-target enzyme. We propose converting the *S. aureus* enzyme structure at the active site to the structure of the human enzyme which has been described. A process whereby this modeling is achieved is called homology structure modeling. This is done computationally by removing the side chains from the enzyme of known structure and replacing them by the side chains of the unknown structure put in sterically plausible positions. In this way it can be understood how the shapes of the active site cavities of the targeted and non-targeted enzymes differ. This process, therefore, provides information concerning how a bound ligand can be chemically altered in order to produce compounds that will occupy additional cavities in the targeted enzyme but will simultaneously be sterically prevented from binding to the non-targeted enzymes. Likewise, knowledge of portions of the bound ligands that are facing the solvent would allow introduction of other functional groups for additional pharmaceutical purposes. This same process of homology structure modeling can be used to understand the mechanisms whereby mutant enzymes become resistant to the effects of pharmaceuticals.

The use of homology structure modeling to design molecules (ligands) that bind more tightly to the target enzyme than to the non-target enzyme has wide spread applicability. The method outlined herein can be used to control any targeted organisms by designing ligands which inhibit the isoleucyl-tRNA synthetase of the target organisms while failing to inhibit the isoleucyl-tRNA synthetase of the non-targeted organisms to the same extent or not at all. The ligands identified or prepared by the methods of the present invention can be used to control the targeted organisms while causing the non-targeted organism little or no adverse effects. Thus, the ligands identified or developed using the methods of the present invention can be designed so that their administration kills the target organisms or inhibits some aspect of the target organisms while failing to have a similar effect on the non-targeted organism. The adverse effects of the agent on the targeted organisms may include, but are not limited to, slowing growth rates, slowing or eliminating reproduction rates, decreasing or preventing mating, decreasing or eliminating offspring production, decreasing organism weights, decreasing or eliminating feeding, and disrupting cellular, tissue and/or organ functions.

Examples of targeted and non-targeted organisms include, but are not limited to, those provided in Table 1.

TABLE 1

Examples of the types of ligands which may be identified and/or developed by the methods of the present invention and the applicable target/non-target organisms.

| Type of Ligand | Target Organisms | Non-Target Organisms |
|---|---|---|
| Herbicides | Dicotyledonous plants | Monocotyledonous plants |
| Herbicides | Grasses | Soybeans, potatoes, coffee |
| Insecticides | Flies | Honey bees |
| Pesticides | Ticks | Deer |
| Pesticides | Lice | Birds |
| Miticides | Parasitic mites (mange) | Dogs |
| Antimicrobial Agents (Antibacterials) | *Streptococcus pneumoniae* | Humans |
| Antimicrobial Agents (Antibacterials) | *Clostridium difficile* | *Escherichia coli* |
| Antimicrobial Agents (Antifungals) | *Erysiphe graminis* | Barley |
| Antimicrobial Agents (Antiprotozoals) | *Toxoplasma gondii* | Animals |
| Poisons | Rats | Dogs, cats, humans |

8. Discrimination Against Mupirocin and Re-Designing the Antibiotic

The structural similarity of mupirocin to amino adenylate analogous inhibitors immediately opens two new avenues of antibiotic design. The first is to re-design this antibiotic, mupirocin, against IRS by replacing its C1 through C4 with an adenosine ring while directly joining a C-10 fatty acid tail at its C6 position. This new antibiotic would likely evade the metabolic inactivation, which design could be the one that the pharmaceutical industry has been searching for in the past decade (Mellows, 1989). The second is to design new antibiotic against other tRNA synthetases, whose structures from both human and pathogenic sources are known, by re-engineering the monic acid portion with proper amino acid analogues.

Mupirocin inhibits many Gram-negative bacterial IRS at nM concentrations, while it binds the human enzyme at a concentration of 3 to 4 orders of magnitude higher (Hughes et al., 1980). This has been an advantage of this antibiotic because of its low toxicity. The crystal structure presented here shows how mupirocin binds to a bacterial IRS and provides a detailed understanding of the binding mode and mechanism. In the absence of the crystal structure of the human enzyme, we cannot provide a definite structural basis for the discrimination against the antibiotic between the two enzymes because of their low similarity (38%) in sequence. Despite of this, we observed that there is a very high degree of conservation (nearly invariant) surrounding the antibiotic binding cleft. This leads to a possible computer modeling exercise to examine discrimination mechanism in the two enzymes.

Sequence differences at N70/K71 of *SA* IRS are the only differences that are directly involved in the recognition of the antibiotic functional groups between the human and *SA* enzymes. This leads to re-designing of a new antibiotic, WSS-1, as described below. We also observed, not merely by coincidence, that sequence differences at the same location are present between the enzymes of *S. aureus* (SA) and mupirocin-resistant *S. aureus* (MUR*SA*). The *SA* and MUR*SA* IRS share a higher similar sequence homology (40% similarity) than the human and *SA* enzymes (38%) do.

On the other hand, we could not identify any sequence differences between *SA* IRS and *Pseudomonic fluoscenes* (*Psefl*) enzyme that could be attributable to a $10^6$ difference in inhibition (Hughes et al., 1980). *Psefl* and *SA* IRS share an even higher similarity (53%) than human (or MUR*SA*) and *SA* do. It is possible that there exist sequence differences between *SA* IRS and the *Psefl* enzyme elsewhere that are not directly involved in, but have strong effects on, the formation of the antibiotic binding cleft.

Both human and MUR*SA* isoleucyl-tRNA synthetases are resistant to the antibiotic, and both have missed an essential asparagine in the recognition of O7. This is not merely a coincidence. If this indeed is the discrimination basis for the discrimination of the antibiotic in these enzymes, this is testable as a working hypothesis by two well established approaches: (1) site-directed mutagenesis in *SA* enzyme to residues that are present in MUR*SA* and/or in human; and, (2) re-synthesis of a new antibiotic that can capitalize the differences at the location.

It is evident that an additional asparagine side chain, as it is present in the wild-type *SA* enzyme, can be placed between the G55 in MUR*SA* and the antibiotic, but not between A65 in human and the antibiotic, as based on a computer modeling of the enzymes for human and MUR*SA*. By slightly reorienting this moiety in the pocket, we observed that the asparagine side chain moiety can directly be fused to the antibiotic at O7 through a methylene group (Cα in FIG. 5) and directly to C16 (FIG. 5). When O7 is replaced with N7, a better interaction is formed with G555 backbone and $H_{585}$ (FIG. 5). Moreover, when the asparagine moiety is replaced by saturated bonds and an additional hydroxyl, we can further capitalize differences in R71 that is only present in MUR*SA*, but not present in the human enzyme. This results in a newly designed antibiotic, named after the authors' (Wang, Silvian, and Steitz) initials, WSS-1, in a first attempt. The present invention provides the structure of the compound in FIG. 4. The present invention provides WSS-1 and compositions comprising WSS-1 and a carrier.

The atomic coordinates for the IRS/tRNA$^{ile}$/WSS-1 complex are deposited on Jul. 26, 2000 at the RCSB Protein Data Bank with the accession number PDB ID: 1FFY.

The present invention provides a method of obtaining novel compounds that interact with IRS and inhibit protein synthesis. The present invention also provides compositions comprising the novel compounds.

9. WSS-1 and its Analogs

The present invention contemplates a compound of formula (I):

wherein $R^1$ is selected from the group consisting of hydrogen, and wherein n is an integer from 1 to 10;

$R^2$ is selected from the group consisting of hydrogen, $-CHCH_3-CH_2-CH_3$, and and $R^3$, $R^4$ and $R^5$ are independently selected from hydrogen, $C_1$–$C_{14}$ alkyl, $C_2$–$C_{14}$ alkenyl, $C_2$–$C_{14}$ alkynyl, $C_3$–$C_{14}$ cycloalkyl, and $C_6$–$C_{14}$ aryl.

In a preferred embodiment, the present invention contemplates a compound having formula (I), wherein $R^1$ is n is an integer from 1 to 8;

$R^2$ is

; and $R^3$, $R^4$ and $R^5$ are independently selected from hydrogen and $C_1$–$C_6$ alkyl.

In another preferred embodiment, the present invention contemplates a compound having formula (I), wherein $R^1$ is n is 8;

$R^1$ is and $R^3$, $R^4$ and $R^5$ are each hydrogen.

The present invention provides WSS-1 shown in FIG. 4. Moreover, the present invention contemplates analogs of WSS-1. In formula (I), the various alkyl, alkenyl, and alkynyl groups may be straight or branched. The alkyl, alkenyl, and alkynyl groups may be optionally substituted with halogen, alkoxy groups, or water-solubilizing groups. A "water-solubilizing group" is a substituent that increases the solubility of a compound in aqueous solution. Exemplary water-solubilizing groups include, but are not limited to, quaternary amine, sulfate, sulfonate, carboxylate, phosphate, phosphonate, polyether, polyhydroxyl, boronate, and amide groups such as —$CONH_2$ and $CONHCH_3$. The water solubilizing groups may also include sulfo, sulfonamido, carbonamido, sulfamoyl, carbamoyl, hydroxyl, and salts thereof.

The $C_2$–$C_{22}$ alkenyl and $C_3$–$C_{22}$ alkynyl groups represent straight or branched chain hydrocarbon radicals containing 2 to 22 carbons in the chain and which contains at least one of a carbon-carbon double bond and/or at least one of a carbon-carbon triple bond.

The $C_3$–$C_{22}$ cycloalkyl heterocycles and rings may contain more than one degree of unsaturation and may be unsubstituted or substituted. The heterocycles and cycloalkyl rings may be optionally substituted with halogen, alkoxy groups, or water-solubilizing groups. These rings may be monocyclic, bicyclic, or polycyclic. In addition, these cycloalkyl rings may or may not contain one or more heteroatoms in the ring. Acceptable heteroatoms are selected from: oxygen, nitrogen, sulfur and phosphorus.

The $C_6$–$C_{14}$ aryl ring may be monocyclic, bicyclic, or polycyclic. In addition, the aryl ring may contain one or more heteroatoms. Appropriate heteroatoms include oxygen, nitrogen, sulfur, and phosphorus. Both the $C_3$–$C_{22}$ cycloalkyl rings and $C_6$–$C_{14}$ aryl rings may be substituted with appropriate $C_1$–$C_4$ alkylaryl, hydroxy, $C_1$–$C_4$ alkanyloxy, halogen or water-solubilizing groups. The aryl group may be substituted or unsubstituted. The term "aryl" includes carbocyclic aryl groups containing up to fourteen carbons, e.g., phenyl and naphthyl. The term "aryl" also includes heterocyclic aryl groups such as a 5 or 6-membered heterocyclic aromatic ring. These heterocyclic aromatic rings may also contain other heteroatoms selected from: oxygen, nitrogen, sulphur, and phosphorous. These heterocyclic aryl rings may be optionally fused to one or two phenyl rings or another 5 or 6-membered heteroaryl ring. Examples of such ring systems include thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl, tetrazolo-[1,5-b]pyridazinyl and purinyl, benzoxazolyl, benzothiazolyl, benzimidazolyl, indolyl, and the like. The aryl groups may be substituted or unsubstituted as discussed above for the alkyl, alkenyl, and alkynyl groups.

In addition, the term "aryl" includes arylene groups. The term "arylene" defines a divalent carbocyclic aryl hydrocarbon moiety containing up to fourteen carbons, e.g., o-, m- and p-phenylene, and those substituted with one or two groups selected from $C_1$–$C_4$-alkyl, C1–$C_4$-alkoxy or halogen.

Further, the present invention contemplates compositions comprising WSS-1 or its analogs and at least one carrier.

Specific Embodiments: Switching from Resting to Synthetic and to hydrolytic Modes in Editing tRNA Synthetases.

The present invention is based in part on the finding that the synthetic active site of three editing tRNA synthetases comprises the HIGH (SEQ ID NO: 5), KMSK (SEQ ID NO: 8), and WCISR (SEQ ID NO: 9) motifs of the dinucleotide Rossmann fold domain and the CWRC (SEQ ID NO: 10) motif of the editing domain. The present invention is also based on the discovery that the hydrolytic active site comprises the TTXPXT (SEQ ID NO: 16) and $GTGX_{11}D$ (SEQ ID NO: 17) motifs of the editing domain. Additionally, the present invention is based on the comparison of the tRNA-free T. Thermophilus isoleucyl-tRNA synthetase in a resting state, tRNA-bound E. coli glutaminyl-tRNA synthetase in a synthetic state, and tRNA-bound S. aureus isoleucyl-tRNA synthetase in a hydrolytic state, which reveals a mechanism for switching from the resting to synthetic and to hydrolytic modes in editing tRNA synthetases. Moreover, the present invention is based on the finding that an RNA binding domain at the anticodon recognition site ensures the tRNA releasing via the hydrolytic mode.

1. Overview of the tRNA-IRS Complex Structure

IRS comprises 7 domains (FIG. 7): amino terminal, dinucleotide Rossmann fold, connective peptide-1 (CP1 or editing domain), connective peptide-2 (CP2), helical, carboxyl terminal junction, and Zn binding domains. Rossmann fold domain in this structure is broken into three parts (FIG. 7) with two insertions of CP1 and CP2 and has a different topology than the one in the glutaminyl tRNA synthetase (QRS) structure (Rould et al., 1989). In IRS, there is an extra parallel strand connecting a pair of α-helices that bind the tRNA acceptor stem (FIG. 7b) at the one side of the β-sheet, and on the other side of the β-sheet, a strand runs in an opposite direction as in QRS. The anticodon recognition site is made of four domains: amino terminal, helical, carboxyl terminal junction, and Zn binding domains (FIG. 7), three of which share novel motifs with two functionally related and an unrelated proteins. The folding motif of the editing domain is unique to this synthetase (Nureki et al., 1997) and does not share similarity with any known structure in the DALI data base (Holm and sander, 1998).

IRS binds tRNA using four synthetase parts (FIG. 7, 9): the putative helix-turn-strand-turn (H-T-S-H) motif that directs the orientation of the tRNA at the inner corner of the L-shaped tRNA (Perona et al., 1991), two pairs of helices, and surprisingly the KMSK (SEQ ID NO: 8) loop. One pair of parallel helices binds the anticodon stem using 14 side chains and two bound metal ions, and the other pair of antiparallel bind the acceptor stem (FIG. 8). The binding of the tRNA to the KMSKS (SEQ ID NO: 6) loop directly controls the switching of IRS from a resting to synthetic and to hydrolytic modes, as described below.

2. Synthetic Active Site of Class-I tRNA Synthetases

Glutaminyl-tRNA synthetase (QRS) in the complex with tRNA and adenylate analogous inhibitor, QSI, provides a direct view of the synthetic complex of all class I tRNA synthetases (Rould et al., 1989), including three editing tRNA synthetases. The synthetic active site is made of the HIGH (SEQ ID NO: 5), WCISR (SEQ ID NO: 9), and KMSK (SEQ ID NO: 8) motifs of the dinucleotide Rossmann fold domain and the $RX_2L$ (SEQ ID NO: 18) motif from the "CP1" domain. While the HIGH (SEQ ID NO: 5) and KMSK (SEQ ID NO: 8) motifs are directly involved in the catalysis (Lowe et al, 1985, Borgfod et al., 1987b, Fersht et al., 1988, Mechulam et al., 1991, First and Fersht, 1995), the WCISR (SEQ ID NO: 9) and $RX_2L$ (SEQ ID NO: 18) motifs provide binding sites for the tRNA 3' CCA end hairpin in the correct conformation inside the synthetic active site (Rould et al. 1989).

3. Synthetic and Hydrolytic Active Sites of Editing tRNA Synthetases

The synthetic active site (FIG. 7) of the three editing tRNA synthetases, isoleucyl-, valinyl-, and leucyl-tRNA synthetases or IRS, VRS, and LRS (Heck and Hatfield, 1988, Borgfod et al., 1987a) is made of the HIGH (SEQ ID NO: 5), WCISR (SEQ ID NO: 9), and KMSK (SEQ ID NO: 8) motifs of the dinucleotide Rossmann fold domain as previously observed (Rould et al., 1989) and the CWRC (SEQ ID NO: 10) motif of the editing domain as described below. The hydrolytic active site (FIG. 7) is made of the TTXPXT (SEQ ID NO: 16) and GTGX$_{11}$D (SEQ ID NO: 17 motifs of the editing domain (Nureki et al., 1998). The editing domain is absent in the other two members of class Ia non-editing tRNA synthetases, methionyl- and cysteinyl-tRNA synthetases or MRS and CRS (FIG. 7C). A switching from a synthetic to hydrolytic modes in IRS involves three of the four motifs: KMSK (SEQ ID NO: 8), WCISR (SEQ ID NO: 9), and CWRC (SEQ ID NO: 10), as described below. We examine these three switching in three distinct states of IRS, a resting, synthetic, and hydrolytic, using QRS as a reference point.

4. Three States of the KMSK (SEQ ID NO: 8) Motif

The KMSK (SEQ ID NO: 8) motif in a loop in IRS binds to the tRNA acceptor stem and is directly coupled with the H-T-S-H motif by 5 hydrogen bonds. A highly conserved carboxylate (D630) at the turn of the H-T-S-H motif makes two hydrogen bonds with two Gua69 ribose hydroxyls and one hydrogen bond to the KMSK (SEQ ID NO: 8) backbone at position 587, which is at the very beginning of the K(595)MSK (SEQ ID NO: 8) loop. This allows the KMSK (SEQ ID NO: 8) loop backbone atoms at positions 593 and 595 to bind both the tRNA Gua68 ribose hydroxyl and Gua69 phosphate.

The KMSK (SEQ ID NO: 8) loop conformation in the tRNA-bound *Sau* IRS structure, different from that in the apo *Tth* IRS structure in a resting mode, is induced by the binding of the tRNA. In the tRNA-free (and adenylate-free) *Tth* IRS structure in a hydrolytic mode, the loop has very large temperature B-factors (Nureki et al., 1997), and the loop cannot make the same interactions as in the complex structure with the imported tRNA after overlaying the two Rossmann fold domains, due to a difference of over 3.6 Å (at K594 in *Tth* IRS) between the two structures. This is a difference in the KMSK (SEQ ID NO: 8) loop between the two states of IRS, the hydrolytic and the resting. The difference extends to the entire tRNA binding surface of the synthetase: the H-T-S-H motif, the two pairs of helices (one pair at the acceptor and the other pair at the anticodon binding sites), and of course the KMSK (SEQ ID NO: 8) loop itself. Away from the binding site, for example, three remaining helices in the helical domain superimpose well in the two states of IRS, indicating a deformation motion in the domain. The binding of tRNA induces a relative motion of the dinucleotide Rossmann fold domain with the rest of the structure.

There exists a third distinct state of the KMSK (SEQ ID NO: 8) loop: a "synthetic" state. We have previously compared the structures of *Sau* IRS in the hydrolytic mode with *E. coli* QRS in a synthetic mode using the superposition of the two tRNAs (Silvian et al., 1999). We found that there was a very large difference in the KMSK (SEQ ID NO: 8) loop of 16.9 Å (at K598) (FIG. 9). The difference is reduced by 5.5 Å (to 11.4 Å), when the two Rossmann fold domains are superimposed. The large reduction in the difference using the two reference frames, tRNA or Rossmann fold domain, between IRS and QRS is likely due to two different states, the hydrolytic and the synthetic. The difference in the KMSK (SEQ ID NO: 8) loop becomes even smaller (8.3 Å) between the two structures of *E. coli* QRS in the synthetic mode and *Tth* apo IRS in the resting mode using the superposition of the two Rossmann fold domains. The difference is 14.6 Å between these two structures of *Tth* IRS and *E. coli* QRS, when *Tth* apo IRS is imported to the *Sau* IRS reference frame by the superposition of the two Rossmann fold domains, and QRS is imported to the same reference frame by the superposition of the two tRNAs. A large change, 6.3 Å between 8.3 Å and 14.6 Å, in two comparisons using the two methods, indirectly through a common reference frame of *Sau* IRS in the hydrolytic mode or directly between *Tth* IRS in the resting mode and *E. coli* QRS in the synthetic mode, is likely also due to two different states, the resting and the synthetic. Therefore, comparisons between a hydrolytic and a synthetic and between a resting and a synthetic suggest the existence of a third distinct "synthetic" state of the KMSK (SEQ ID NO: 8) loop in IRS. Consistent with this, we argue for the existence of the "synthetic" state below from the two other locations involved in switching.

5. The KMSK (SEQ ID NO: 8) Loop Controls the Release of the Synthetic Products

The KMSK (SEQ ID NO: 8) loop controls the accessibility of amino adenylates in class I tRNA synthetases. When an amino adenylate is absent, the loop is often disordered or has large temperature B-factors (Monteilhet et al., 1984, Brick et al., 1988, Nureki et al., 1998). In the presence of amino adenylate, or its analogous inhibitor, or ATP, the second lysine (K598 in *Sau* IRS and K270 in *E. coli* QRS) ) in the loop binds both α and γ-phosphate of ATP or its analogous position of QSI in the QRS complex structure (Rould et al., 1989, Rath et al., 1998). The reason that QSI (an amino adenylate with a nonhydrolyzable glutamine-ATP linkage) or similarly designed inhibitors bind tightly to non-editing class I tRNA synthetases is that there is an additional domain on top of the KMSKS (SEQ ID NO: 6) loop (FIG. 9E) to limit the loop motion and to prevent the activated amino acids from unnecessarily diffusing out. In the observed open conformation of the KMSK (SEQ ID NO: 8) loop in IRS at the synthetic active site, noncognate amino adenylates and mischarged valine-tRNA$^{ile}$ can easily be shuttled out (Silvian et al., 1999). Amino adenylate analogous inhibitors with a design similar to QSI would fail to bind to IRS because of the large-scale opening motion of the KMSKS (SEQ ID NO: 6) loop. New IRS inhibitors have to take the loop motion into account in the design. Mupirocin, a naturally occurring antibiotic, present in the co-crystal structure, in part has such a feature with negatively charged groups at the end of a very long hydrophobic tail. The negatively charged groups bind to lysines in the loop while the long tail fixes the loop motion.

6. The KMSK (SEQ ID NO: 8) Switching

The KMSK switching involves metal ion mediated tRNA-synthetase recognitions at the inside corner of the L-shaped tRNA near the D-loop (FIGS. 7, 9). This includes a conserved carboxylate (D626) that binds the tRNA using both its backbone amine and its side chain through metal ion #3 at the turn of the H-T-S-H motif. At the middle of the strand in the motif, a partially conserved, positively charged residue (R632) makes two hydrogen bonds with phosphate backbone of both Uri13 and Cyt13. The second helix in the motif provides an additional 5 side chains for formation of 6 hydrogen bonds with the tRNA. In a combination with this helix, an additional long α-helix provides 8 side chains for binding to the tRNA$^{ile}$ (LAU) isoacceptor and 7 for the tRNA$^{ile}$ (GAU) isoacceptor, directly mediated by two bound metal ions.

To address the question as to why a chimerical tRNA$^{ile}$ with a transplanted D-loop from tRNA$^{val}$ failed to activate the IRS hydrolysis (Hale et al., 1997), we have to consider the possibility of an indirect cause, since IRS does not bind to the D-loop. In other words, we want to know what are the structural features of the tRNA next to the D-loop that are recognized by IRS and that are also sensitive to an alternation within the D-loop. A least squares superposition of the tRNA structures (FIG. 10) shows that tRNA$^{ile}$ and tRNA$^{ile}$ superimpose well with each other at both the T-loop and D-loops and that both tRNAs belong to a subfamily of α3β1, according to number of nucleotides in positions α and β (Kim, et al., 1974). Likewise, tRNA$^{gln}$ and tRNA$^{phe}$ superimpose well, and both belong to a subfamily of α2. Since both tRNA$^{val}$ and tRNA$^{phe}$ belong to the α2β1 subfamily, we decided to use tRNA$^{phe}$ as a model for tRNA$^{val}$ to examine the consequence of the D-loop transplantation. At a minimum, the tRNA would lose three hydrogen bonds (FIG. 9D), two with R632 (Uri12-O2P and cyt13-O1P) and one with the backbone amine of N235 (Uri12O2'). Since only two of the three consecutive guanosines present in the D-loop are tertiary bases, Hale et al., (1997) implied an alternative, novel classification of tRNA$^{val}$ as α3/β0 rather than α2/β1, a classification never anticipated by the original authors (Kim et al., 1974). If true, tRNA$^{val}$ would have a very different structure at the D-loop from what we currently know about the tRNA structure in general.

7. The WCISR (SEQ ID NO: 9) and CWRC (SEQ ID NO: 10) Switching

The WCISR (SEQ ID NO: 9) and CWRC (SEQ ID NO: 10) motifs in editing tRNA synthetases provide three positively charged residues and two hydrophobic residues to stabilize the 3' tRNA end hairpin structure when it is present in the hypothetical IRS synthetic mode on the basis of modeling (Silvian et al., 1999). Differences (3–5 Å, see below) in these motifs between the hypothetical synthetic structure and the resting Tth apo IRS is much smaller than those (16.3 Å) between the structures of resting apo Tth IRS and hydrolytic Sau IRS.

Figure 10A:
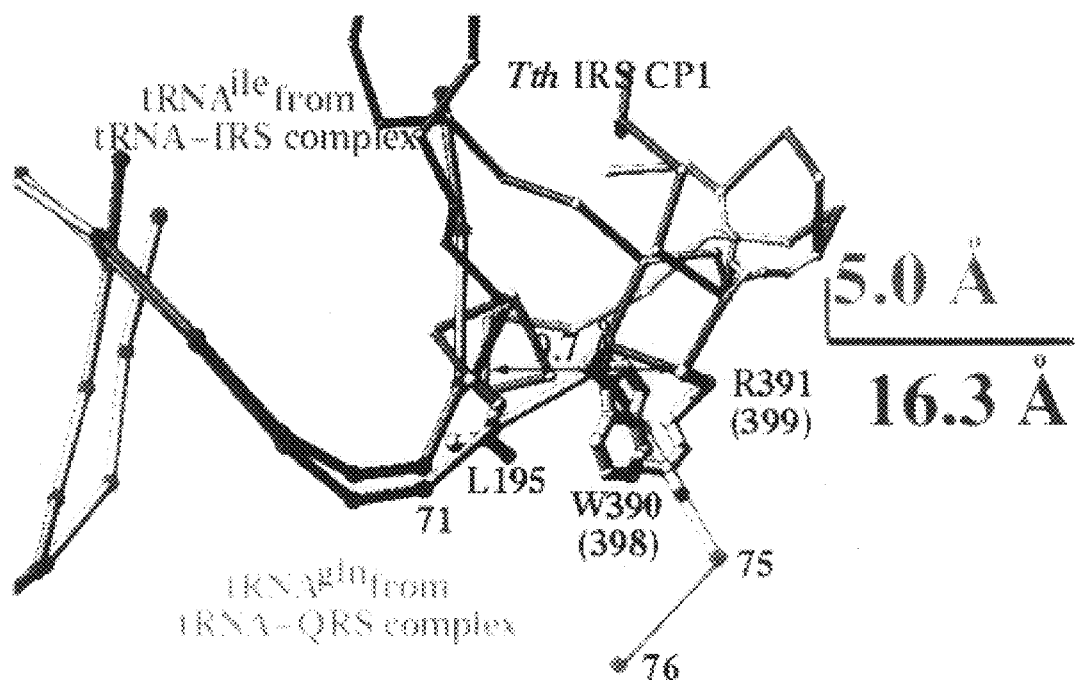
Figure 10B:
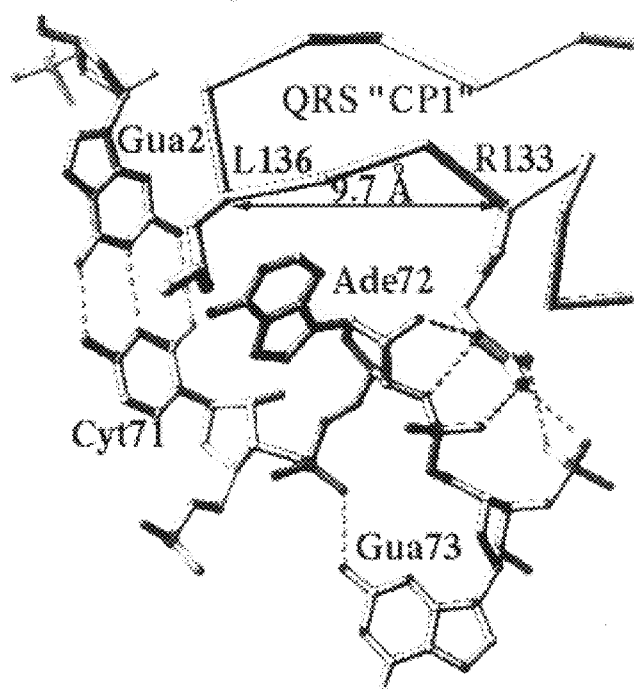
Figure 10C:
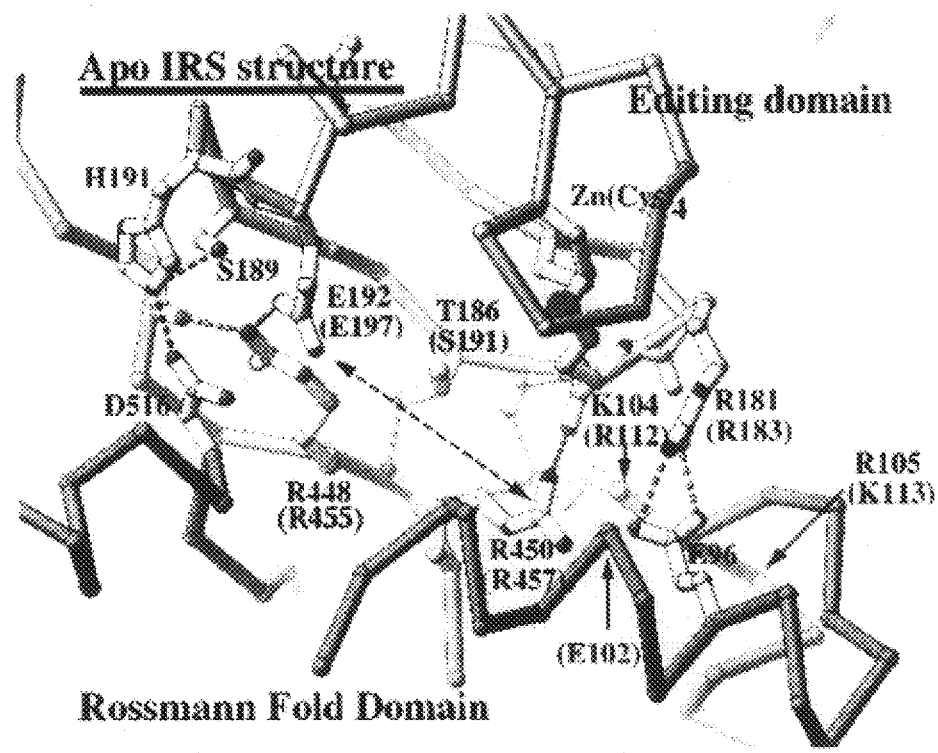
Figure 10D:
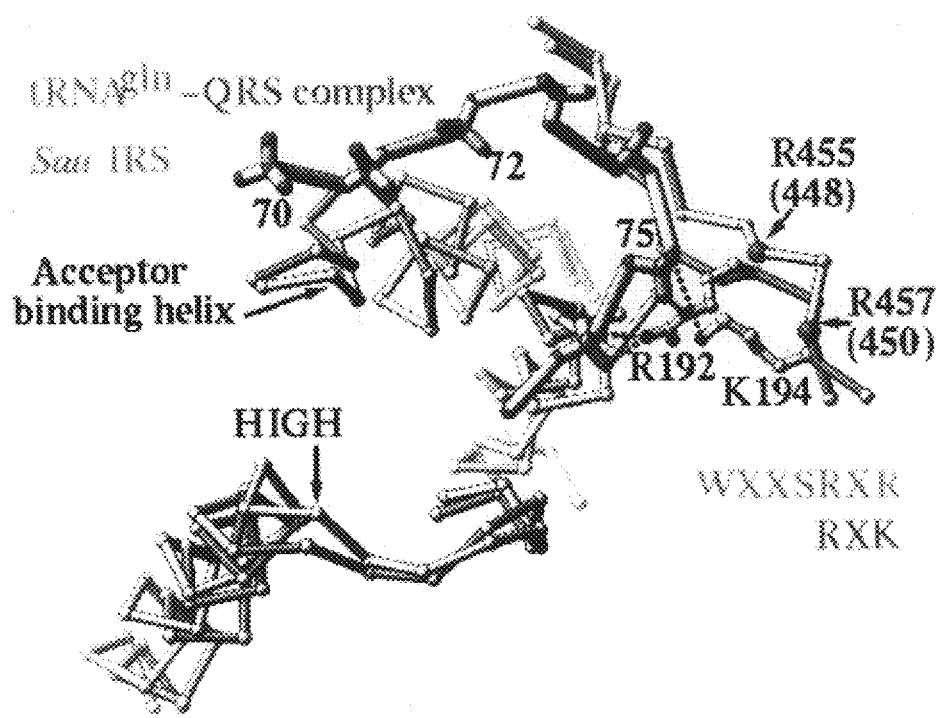
Figures 10E, 10F:
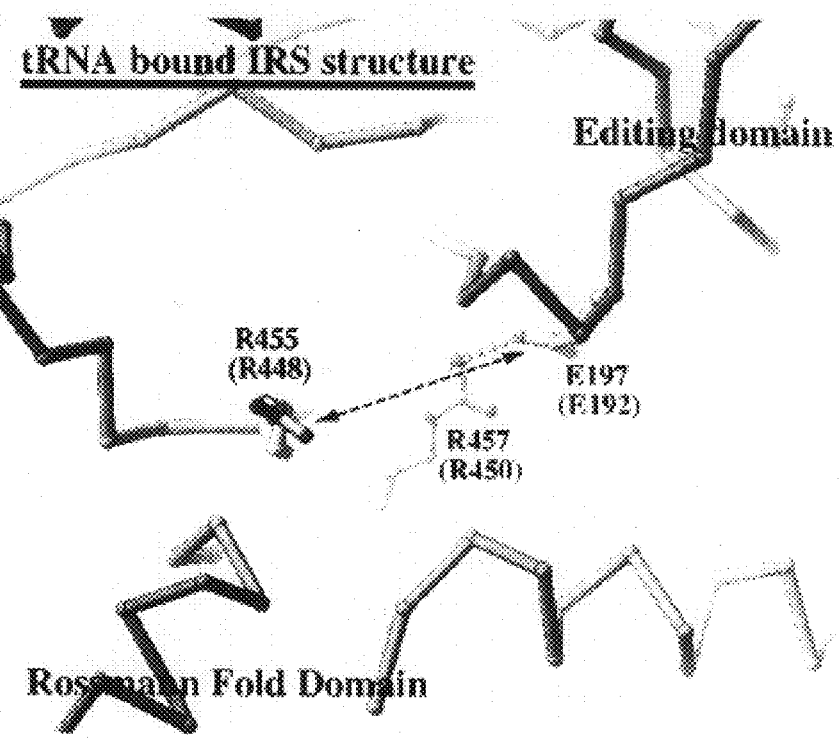

Two conserved, positively charged residues in the WCISR (SEQ ID NO: 9) motif stabilize the hairpin structure in the synthetic modes in the class I tRNA synthetases. We have previously observed the structural conservation of the WCISR (SEQ ID NO: 9) motif between IRS and QRS when we imported tRNA$^{gln}$ onto IRS by a least squares superposition of the two RNAs (Silvian et al., 1999): R455 in IRS could make the same interaction with the tRNA 3' hairpin in the synthetic active site as R192 in QRS. There is another highly conserved positively charged residue in all class I tRNA synthetases including the three editing synthetases immediately following the S of the WCISR (SEQ ID NO: 9) motif, namely K194 in QRS and R457 in IRS. In the synthetic complex of QRS, both R192 and K194 make four hydrogen bonds with the tRNA 3' hairpin phosphates (FIG. 10D). In the modeled synthetic complex of IRS, derived from the Sau IRS hydrolytic complex, R457 is oriented differently and is hydrogen bonded with another conserved residue in the CP1 domain to stabilize the interactions between the CP1 and Rossmann fold domains (FIG. 10E). Once the 3' CCA hairpin is in the synthetic active site, we expect that R457 would have the exactly same orientation and binding function as K194 in QRS (Rath et al., 1998). This requires a reorientation of the CP1 domain and breaking inter-domain hydrogen bonds involving this residue.

The CWRC (SEQ ID NO: 10) motif of the IRS editing domain, conserved among all three editing tRNA synthetases, is equivalent to the RX$_2$L (SEQ ID NO: 18) motif in QRS. R133 is in QRS in this motif and makes 5 hydrogen bonds with the tRNA 3' CCA hairpin phosphates, and L136 stacks with Ade72 on one side and the Waston-Crick base-pairing of Gua2=Cyt71 on the other side (FIG. 10B). The equivalence is apparent when apo Tth IRS in a resting mode is imported to the Sau IRS reference frame by the superposition of the two Rossmann fold domains (FIG. 10A): the CP1 domain contribute three residues, R391, W390, and L195 for the same function as R133 and L136 in QRS. A distance between R390 and L195 Cα in Tth IRS is the same as R133 and L136 in QRS, 9.7 Å; and the orientation of two side chains is also similar. If the CP1 in the hypothetic synthetic mode is displaced upwards as indicated in the figure (FIG. 10A) by 5.0 Å, R391 and L195 would have an identical geometry as R133 and L136 in QRS. Moreover, W390 in Tth IRS can additionally stack on the other side of the nucleotide in position-72. Since tRNA$^{ile}$ has a C at position-72 of the 3' CC(-72)ACCA end, smaller than an A of the tRNA$^{gln}$ 3' CA(-72)GCCA end, the displacement should actually be less than 5.0 Å. R391 and L195 in Tth IRS resemble R133 and L136 in QRS only in the three-dimensional structure but not in the primary sequence. This is an example of structural element swapping (see below).

The residues WR of the CWRC (SEQ ID NO: 10) motif are strictly conserved among all known editing tRNA synthetases in the public data base, but not among non-editing tRNA synthetases (FIG. 7C). In LRS, the CWRC (SEQ ID NO: 10) motif is transposed from the ending of the editing domain to its beginning (FIG. 7C). In Sau IRS, even though two flanking C are replaced by S, the structure is maintained identically without involving the two cysteine residues and a bound Zn ion at the location. L195 is highly conserved among IRS but missing in Sau IRS. Lastly in FIG. 10A, the CP1 domain in the Tth apo conformation in the resting mode overlaps with the observed, bound tRNA in the phosphate-continuously base-stacked conformation in the hydrolytic mode and acts as an origin for induced-fit motion, as described below.

8. Three States of the WCISR (SEQ ID NO: 9) and CWRC (SEQ ID NO: 10) Motifs

There exist three distinct conformational states of the WCISR (SEQ ID NO: 9) and CWRC (SEQ ID NO: 10) motifs: resting, synthetic, and hydrolytic. The CWRC motif in the resting Tth apo IRS state is about 3–5 Å closer to the synthetic active site than it should be in the hypothetical synthetic state, derived from the QRS structure. This resting conformation state is maintained by, and directly results from, 7 conserved interdomain hydrogen bonds immediately underneath it (FIG. 10C). Inter-domain hydrogen bonds include the two conserved, positively charged residues of WCISR (SEQ ID NO: 9) motif (R448 and R450 in Tth IRS, and R455 and R457 in Sau IRS). The CWRC (SEQ ID NO: 10) motif in the hydrolytic Sau IRS state is displaced about 16.3 Å (at R391 Cα) away from it in the resting state (FIG. 10E). This is the only hydrogen bond that can maintain the relative geometry between the CP1 and Rossmann fold domains (FIG. 10E) and is derived from the conserved arginine (R457 in Sau IRS). In the hypothetical "synthetic" state of IRS, both arginine residues in the WCISR (SEQ ID NO: 9) motifs would bind the tRNA 3' hairpin phosphates, and the CP1 should move back slightly to allow the WR of the CWRC (SEQ ID NO: 10) motif to bind both the tRNA 3' hairpin bases and phosphates.

9. Which Way Out? Which Way In?

Figure 12A:
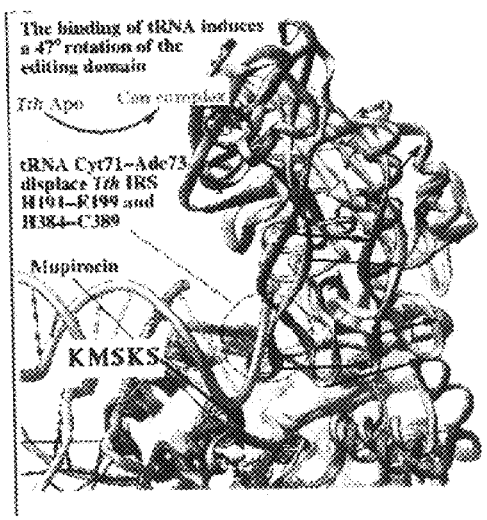
Figure 12B:
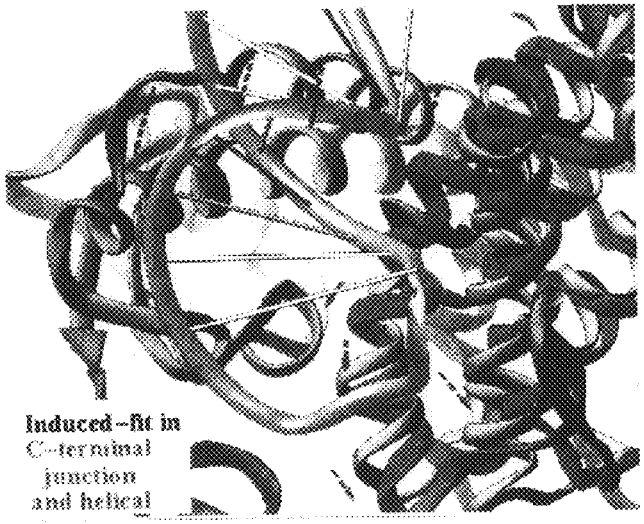
Figure 12C:
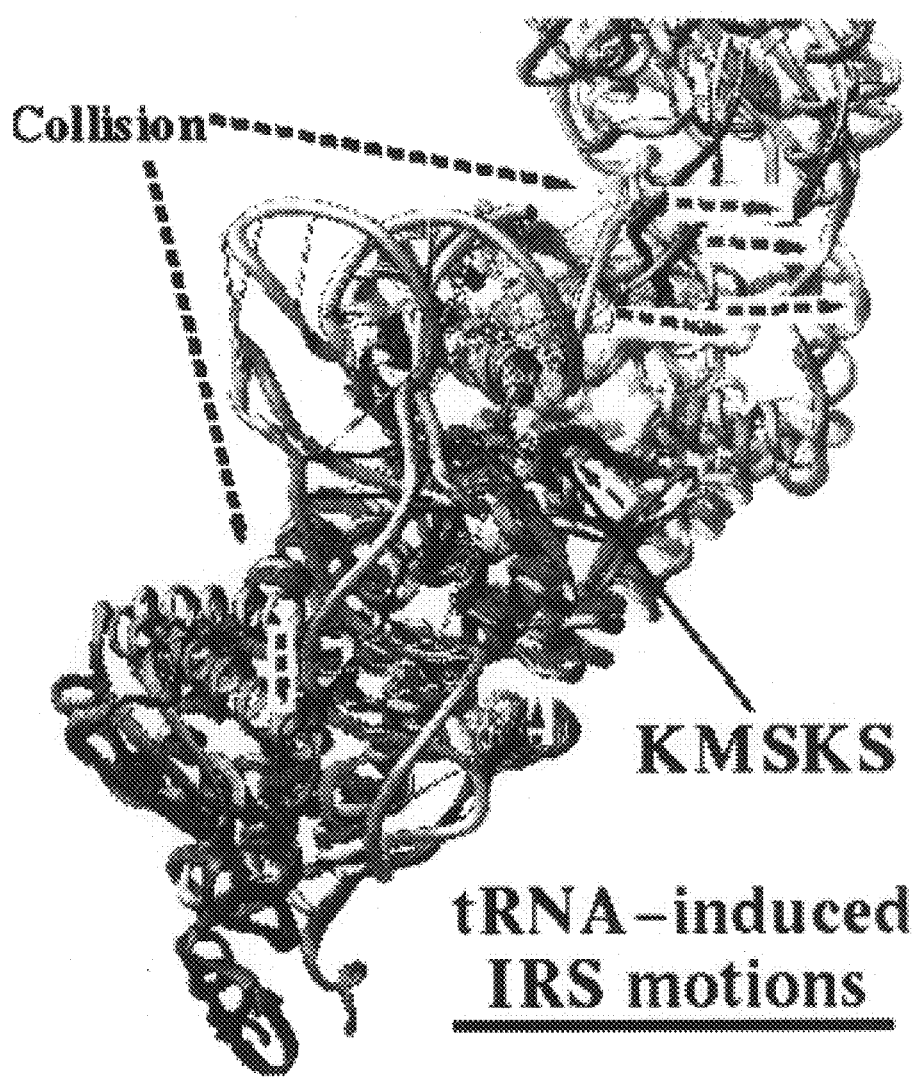
Figure 12D:
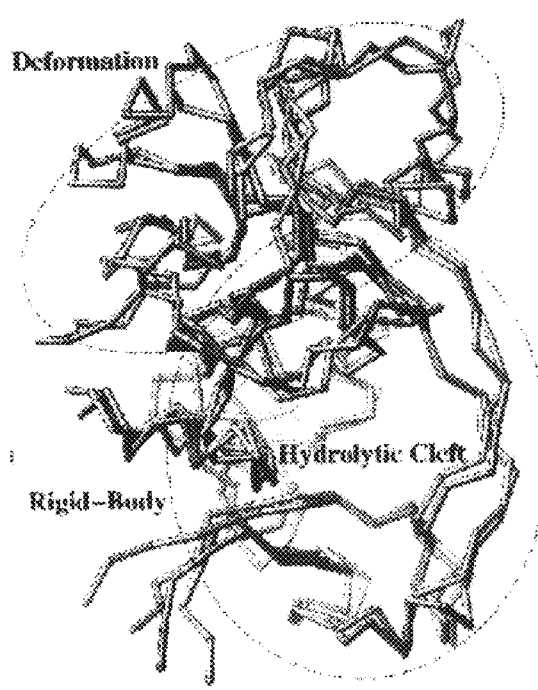
Figure 12E:
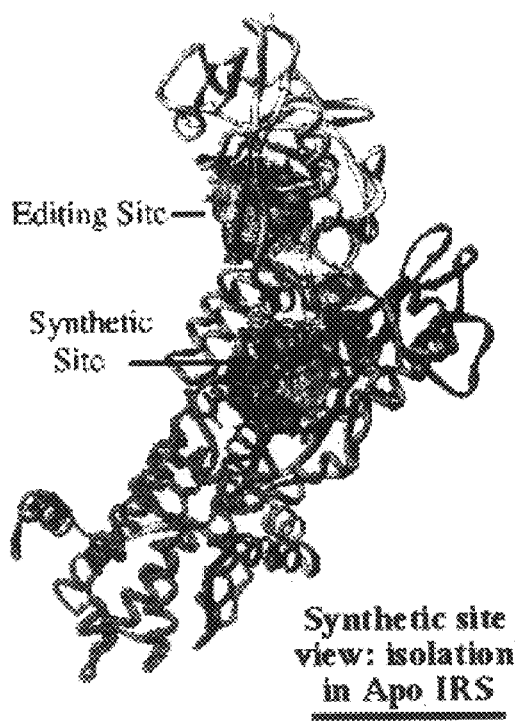
Figure 12F:
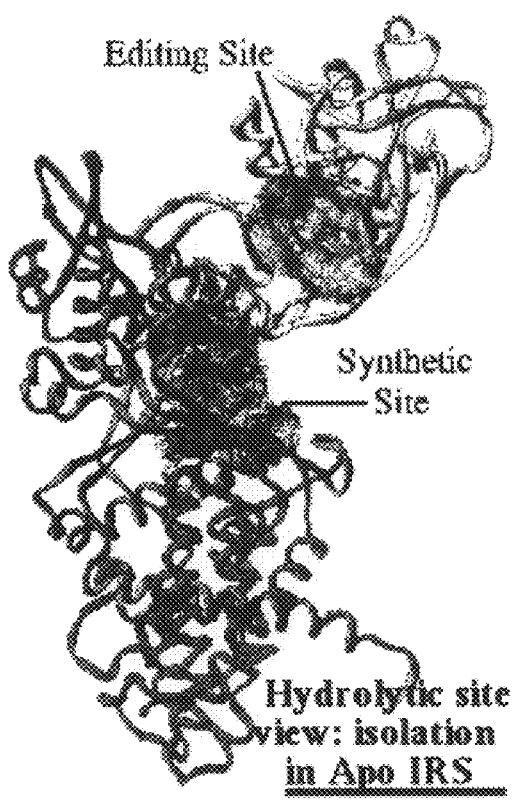
Figure 12G:
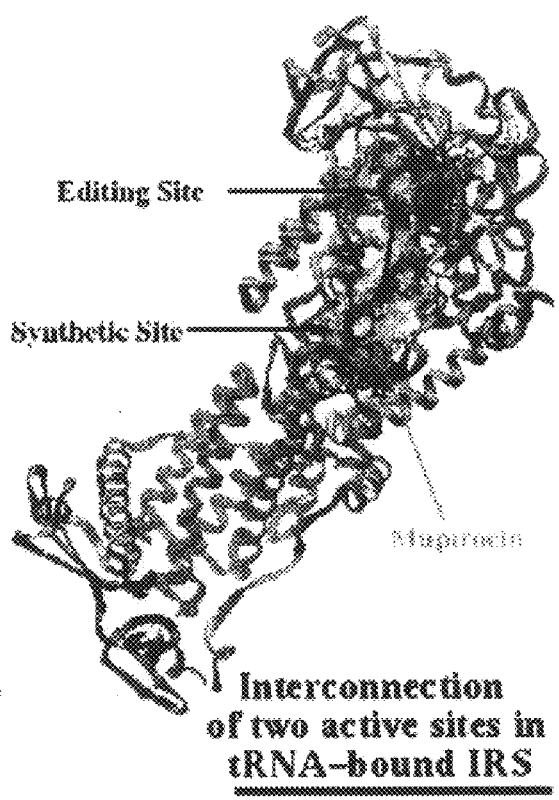

The tRNA binds IRS in a deep cleft made of domains not present in QRS. This includes four anticodon binding domains: helical, C-terminal junction, Zn-binding domain, and amino terminal domains. In the QRS complex, the tRNA can bind to, and be released from, the synthetase in the three indicated directions (FIG. 11C): left horizontal, up vertical, and out towards the viewer. A hypothetical synthetic complex is constructed on Sau IRS with its CP1 domain oriented according to Tth apo IRS, and tRNA from QRS complex (FIG. 11A). In this model, there is no unique way to remove the tRNA from the complex without steric clash with the synthetase: the left horizontal exit is blocked by the C-terminal junction domain, both paths of the up vertical and out towards the viewer are blocked by the CP1 domain. Moreover, the tRNA-IRS interactions are stronger than in the QRS complex; they include two additional helices, three bound metal ions in IRS, but not present in the QRS complex. Just how the tRNA is released from this synthetase is a challenging issue, as is the mode of tRNA binding. Which way out? Which way out? We believe the answer lies at the tRNA-induced swiveling motion of the editing domain, and the tRNA-induced structural formation of the anticodon recognition site 10. The Editing Domain Switching, and the C-Terminal and Zn Binding Domain Switching The first step that allows the tRNA to be released from IRS is that the editing domain has to be pushed out of the way to force the tRNA to go through the "hydrolytic state" of the enzyme. In the synthetic complex, all exits for the tRNA are blocked (FIG. 11A). In the editing complex, tRNA can be released by exiting either in the up vertical or in the out towards the viewer directions (FIG. 11B). When tRNA is ready to be released, its 3' CCA end first assume a more stable phosphate-continuously base stacked conformation. This forces the editing domain to yield; otherwise the tRNA and the editing domain would overlap (FIG. 13, and FIG. 10A). This causes a 47° rigid-body swiveling motion of the editing domain (FIG. 12D). After releasing the tRNA, IRS returns to a resting state as in Tth IRS with 7 inter-domain hydrogen bonds. In this exiting path, all charged tRNA$^{ile}$ molecules are checked for errors.

The tRNA-induced editing function of IRS is highly analogous to that in DNA polymerases (Silvian et al., 1999), with the exception of a large motion of the editing domain (FIG. 12). In all three states of IRS, the two active sites located in two isolated clefts in two domains, are separated by 34 Å (FIG. 12E–G). Upon the completion of the transfer or mis-activation reactions, a large swiveling motion of the editing domain which takes place before the releasing of the tRNA, allows the two active sites to be internally aligned on a contiguous surface (FIG. 12G). This facilitates the shuttling of either noncognate valine-adenylate or mischarged valine-tRNA$^{ile}$ to the hydrolytic active site for subsequent hydrolysis.

In the first step of the tRNA binding to IRS, there is also a checking mechanism. This is in the anticodon recognition site. In the resting Tth IRS state, the entire Zn-binding, C-terminal junction, and N-terminal domains with the exception of one helix are un-structured. The importance of a folded Zn binding domain in IRS function has been shown by many biochemical studies (Nureki et al., 1993, Glasfeld and Schimmel, 1997, Zhou and Rosever, 1995). This is where the cognate tRNA is first recognized. The binding of the only cognate tRNA with isoleucyl-tRNA isoacceptors will reduce the flexibility of the three domains and convert the un-structured to structured anticodon recognition site which is what is seen in the Sau IRS complex structure. A noncognate tRNA is not able to introduce the structural formation of the anticodon binding site, and is not bound by the synthetase. tRNA mini-helices may bind to IRS at much lower affinity and occasionally be charged (Nordin and Schimmel, 1999), but they are neither checked by the anticodon recognition mechanism nor by hydrolytic releasing pathway.

11. A Relationship of IRS Anticodon Binding Domains with Other Proteins

All IRS large domains are unique and in a class by themselves with the exception of the dinucleotide Rossmann fold domain, which is shared by all class I tRNA synthetases and many other proteins (FIG. 7). The editing domain does not share any structural homology with known structures in the DALI data base (Nureki et al., 1998). This is a novel β-barrel like structure. The helical domain is found only in a non-editing tRNA synthetase of known structure, namely tRNA$^{met}$ synthetase, MRS (Brunie et al., 1990); however, this is the first time that we have observed a domain employs novel metal ion-mediated protein-nucleic acid interaction to bind tRNA. The C-terminal junction and Zn binding domains share the folding motif with one functionally related and one unrelated proteins, as described below.

The C-terminal junction domain shares a folding similarity with a subunit of protein synthesis apparatus, ribosomal L22 (Unge et al., 1998), in an α-helix and two middle strands of the four-stranded β-sheet (FIG. 13A). The two outer strands of the four strands were not identified as homologous structures by the DALI alignment procedure (Holm and Sander, 1998), because they are unrelated in the primary sequence. In these two structures, all four strands appear to align, or at least the two outer strands occupy the same locations (FIG. 13A). The top strand (FIG. 13A) in the two structures is topologically unrelated in linear arrangement of two sequences; the bottom strand runs in an opposite direction of the N→C peptidyl bonds. This is the second example of secondary structure swapping in evolution, and is an extension to the widely known domain-swapping theory (Bennett et al., 1995). The first example is the CWRC motif as described above. These two domains may also share similar protein-nucleic acid interaction patterns, one in the synthetase, the other in the ribosome. The IRS C-terminal domain does not directly bind the tRNA; all interactions are mediated by solvent molecules. Structural similarities between synthetases and ribosomal proteins are not uncommon, for example, between a QRS RNA binding domain and L25 in protein synthesis (Stoldt et al., 1998).

The Zn binding domain shares a folding similarity with a membrane-targeting, Zn-binding motif, FYVE (SEQ ID NO: 19, Misra and Hurley, 1999), which is dependent on phosphatidylinositol 3-phosphate (PI3 P), a functionally unrelated motif (FIG. 13B). Two surprising findings arose during the comparison. In the first, the backbone of the loop forming a second Zn binding site in FYVE (SEQ ID NO: 19) motif domain is inserted between the two stranded, antiparallel β-sheet occupying precisely the site where the amino terminal helix lies in IRS. This is the third example in IRS of secondary structure swapping or domain-swapping in evolution, since we have narrowly defined the amino terminal helix by itself as the amino terminal domain. The second, the two functionally unrelated proteins share an architecture in the binding sites for two unrelated substrates. In IRS, W890 of the Zn binding domain and L7 of the amino terminal domain form the pocket for the binding of Gua34; in the membrane-target motif, a similar location between the two Zn binding sites is predicted to bind PI3 P (Misra and Hurley, 1999).

In order that the present invention described herein may be more fully understood, the following examples are set forth. It should be understood that these examples are for illustrative purposes only and are not to be construed as limiting this invention in any manner.

EXAMPLES

Example 1
The preparation of tRNA$^{ile}$ and IRS

The gene for the major isoacceptor of tRNA$^{ile}$ (GAU) from *E. coli* was cloned behind a T7 RNA polymerase promoter with a BstN1 site at its 3' terminus to produce run-off transcripts (Rice, L, Smerdon, S., and Steitz, T. A, unpublished results). T7 RNA polymerase was overexpressed and purified according to D. Jeruzalmi (PhD thesis, 1995, Yale University). Production of plasmid encoding the *E. coli* sequence tRNA$^{ile}$ (GAU) was scaled up according to the Biofeedback's protocol and was digested, transcribed, purified, and folded as the tRNA$^{gln}$ protocol (Silvian, L. F., PhD thesis, 1997, Yale University).

IRS from *S. aureus* was overexpressed and purified according to Chalker et al., (1994) and dialyzed into storage buffer containing 20 mM Tris HCl pH 8.0, 1 mM DTT, 5 mM MgCl$_2$, 50% glycerol, and kept at a −70° C. freezer. The overexpression clone, and purified IRS protein sample used in the initial stage of the present invention were kindly provided Dr. S. Abdel-Mequid at SmithKline Beecham.

Cloning of IRS from S. Aureus (Chalker et al., 1994):

Sequences of tryptic peptides of IRS from *S. aureus* protein and deduced oligos used as hybridization probes.

```
        aa  V  I  V  P  D  Q  V  V  K        SEQ ID NO: 1
probe   nt  GTtATTGTtCCaGAtCAAGTtGTTAAA       SEQ ID NO: 2
X               A  T        a aa  G  N  I  N  D  F  N  P  D        SEQ ID NO: 3
probe   nt  GGTAATATTAATGATTTtAATCCaGAT       SEQ ID NO: 4
Z               a  c           T
```

The first line of the nucleotide (nt) sequence shows the condons most frequently used in *S. aureus* (Wada et al., 1991, Nucleic Acids Res. 19 Suppl., 1981–1986). Capital letters indicate the nt used in the ileS gene. The aa sequence is the amino acid sequence corresponding to the nt sequence.

Methods: Oligos X and Z were synthesized on a Gene Assembler Plus (Pharmacia LKB) using 0.2-μm supports; deprotected in ammonia; and desalted using NAP10 columns. Gels of *S. aureus* chromosomal DNA digested with a variety of restriction enzymes were prepared for hybridization analysis as described by Southern (1975, J. Mol. Biol. 98, 503–517) and the DNA was transferred onto Hybond-C Extra nitrocellulose membranes (Amersham International) using a Hybaid vacuum blotting apparatus. Oligos X and Z were radioactively labeled in kinase reactions using [γ-$^{32}$P] ATP (Amersham International), purified on Stratagene Nuc-Trap columns, and used to probe the membranes in 1 M NaCl/0.1 M Na$_3$.citrate/5×Denhardts/100 μg per ml of denatured salmon sperm DNA at an experimentally-determined optimum temperature (Z: 60° C., X: 45° C.). The membranes were washed in 1 M MaCl/0.1 M Na$_3$.citrate/0.1% SDS. Both probes hybridized to bands of identical size in corresponding digests. To construct the recombinant library, chromosomal DNA from *S. aureus* Oxford (isolated using the method of Marmur (1961, J. Mol. Biol. 3, 208–218) was partially digested using TaqI. Fragments of 5–10 kb were purified on a 10–40% sucrose density gradient, and ligated into pAT153 (Twigg and Sherratt, 1980, Nature, 283, 216–218) which had been cut with ClaJ and treated with calf intestinal alkaline phosphatase to prevent recircularization. 6700 library clones created by electroporation (Bio-Rad Gene Pulser) of library DNA into *E. coli* DH1 competent cells (Hanahan, 1983, J. Mol. Biol. 166, 557–580) were screened by colony hybridization using oligo probe Z under the conditions determined earlier. DNA from a positively-hybridizing library clone containing a plasmid with an insert of 8.5 kb (pBROC461) was purified (Magic Miniprep kits, Promega, Madison, Wis., USA) and tested by restriction analysis and Southern blotting. A single band in each restriction digest hybridized to both probes Z and X. A 2.1-kb hybridizing EcoRI fragment of pBROC461 was electrocuted from an agarose gel using an IBI Unidirectional Electroeluter and subcloned into the EcoRI site of pUC19 in *E. coli* JM109 (Yanisch-Perron et al., 1985, Gene 33, 103–119) for DNA sequencing (pBROC462). All bacterial strains were grown in L-broth which was supplemented with 100 μg Ap/ml (Beecham Research Laboratories) for selection of plasmid transformants, and with 70 μg/ml each of XGal and IPTG when the plasmid carried an inducible lacZ marker.

Cloning Strategy Used to Overproduce S. Aureus IRS in *E. coli*:

1. The N terminus of the ileS gene (which encodes IRS) up to the NdeI site was amplified by PCR from PBROC461, using primers C and D (see below) with an extension period of 1 min. at 42° C. in a Hybaid thermal cycle under standard conditions.

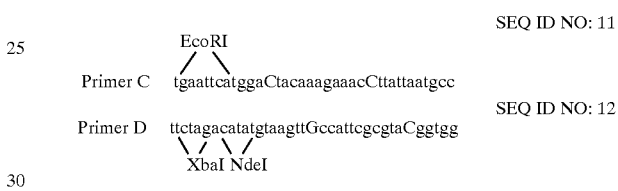

The arrowhead below primer C indicates the start codon of the ileS gene (bp 1). The first C following the Xba1 site of primer D (with the NdeI site) corresponds to bp 196 of the ileS gene. Capital letters indicate conservative changes introduced in order to enhance ileS expression from pBROC465. The 208-bp PCR fragment was gel purified and cloned into pCRII (TA Cloning System Invitrogen), generating pBROC463.

2. EcoRI and XbaI sites introduced during PCR were used to remove a 200-bp fragment, which was ligated into the expression vector pDB575 cut with EcoRI+XbaI, generating pBROC464 in which the start codon is 9 bp from the RBS and near to P$_{tac}$.

3. The 3.5-kb NdeI-BglII fragment of pBROC461 which carries the rest of the ileS gene was ligated into pBROC464 cut with NdeI+Bg/II, generating pBROC465 which carries the reconstituted ileS gene in front of P$_{tac}$ pDB575 was constructed by replacing the ScaI$^{3486}$-SphI$^{562}$ pBR322 fragment of pKK223–3 (Pharmacia LKB) with the equivalent fragment of pATI 53: cloning a 1.7-kb EcoRi lacI$^q$ fragment from ptacI$^q$ into the EagI site; and inserting an MCS between EcoRI and HindIII to give a non-mobilizable lacI$^q$ P$_{tac}$ expression vector.

Methods: *E. coli* DH1[pBROC465] cultures were grown in Ap-containing L broth at 37° C. to an A$_{600}$ of 0.5 and induced with 1 mM IPTG. For the IRS assay, log-phase *E. coli* cultures were sonicated and the extracts treated with DNase, centrifuged and dialysed against Tris pH 7.8. Following the addition of 2 mM DTT and 50% glycerol the extracts were assayed for incorporation [$^3$H]Ile using the method of Durekovic et al. (1973, Eur. J. Biochem. 36, 528–533). Protein extracts for SDS-PAGE were prepared as described in Sambook et al. (A Laboratory Manual. Cold Spring Harbor Laboratory Press, Cold Spring Harbor, N.Y. 1989) on pp. 18.40–18.41, and run on FlowGen Gss-312 gels in Gradipore TSS buffer.

Example 2
Crystallization of Mupirocin with Isoleucyl-tRNA Synthetase and the Cognate tRNA$^{ile}$ In preparation for crystallization, IRS was dialyzed into 20 mM Bicine pH 8.0, 50 mM KCl, 5 mM MgCl$_2$, 2 mM β-mercaptoethanol, 1 mM ZnCl$_2$ and concentrated to 20 mg/ml in a centricon-15 (Amicon). The tRNA transcript was folded by dissolving a lyophilized pellet in 10 mM Na Cacodylaie pH 6.0, 5 mM MgCl$_2$ at a concentration of 5 mg/ml, heating at 60° C. for 5 minutes and then slow-cooling to 25° C. for an hour. The tRNA was then lyophilized and dissolved to a concentration of 20 mg/ml with 40 mM Na Cacodylate pH 6.0 and 20 mM MgCl$_2$. The complex of 50 uM IRS, 50 uM tRNA and 1 mM mupirocin was mixed with the well solution at a volume ratio of 3 ul well: 1 ul complex. The well solution contained 12% PEG 6K, 0.3M KCl, 100 mM Na Cacodylate pH 6.3, 100 mM MgSO$_4$, 2 mM ZnCl$_2$, and 0.1% β-octyl glutopyranoside. The drops were streak-seeded without prior equilibration and then equilibrated at 20° C. by the hanging-drop method. Crystals were frozen by replacing the mother-liquor with a cryoprotectant containing the well solution with the addition of PEG 6K to a final concentration of 20% (w/v) and ethylene glycol to a final concentration of 15% (v/v) and then flashed-freezing in liquid propane. The mother liquor is the equilibrated crystal drop solution containing the well solution (the same chemicals and concentration) plus mupirocin and very low concentrations of IRS and tRNA.

Example 3
Structure Determination

Crystals of the ternary complex of mupirocin with its target enzyme, IRS, and tRNA were in space group P2$_1$2$_1$2$_1$, diffracted to 2.2 Å resolution and exhibited two unit cell sizes: a large cell (a=71 Å, b=100 Å, c=186 Å) and a small cell (a=71 Å, b=100 Å, c=180 Å). The 18 selenium sites of selenomethionine-incorporated IRS per asymmetric unit were located using the program SOLVE (Terwilliger, 1994) on MAD data that had been locally scaled using MADPRB (Friedman, et al., 1994). Refinement in CNS (Brunger et al., 1998) with a maximum likelihood Henderickson Lattman (MLHL) target yielded an overall R$_{free}$ values of 28.1% for reflections between 10 and 2.2 Å from the large cell crystal form and an overall Rfree value of 34.3% for reflections between 10 and 2.9 Å from the same cell crystal form.

Derivatives were phased in MLphare using CCP4 (CCP4, 1994) bya novel method called permuting the Native/Derivative. In this procedure, data collected at each of the MAD wavelength were considered the "native" in four parallel MIR refinements and then phases from all four refinements were combined by their Hendrickson-Lattmann coefficients in SigmaA (CCP4, 1994). Phase improvement was measured by the objective criterion of monitoring the height of a difference Fourier peak of an independent derivative for which there was a clear different Patterson peak. Using the selenium derived phases, additional sites in other derivatives were identified. The MAD and MIR phase sets from all derivatives were combined using SigmaA (CCP4, 1994) weighting and the resultant map modified in SOLOMON (Abrahams and Leslie, 1996). In a second round, the heavy atom parameters were independently refined using density modified external phases (Rould et al, 1992) and all phase sets were combined again. In the large-cell, the course of the backbone of the entire protein was traced using experimental maps with the exception of a region between residues 205–390 in the editing (CP1) domain and the last nucleotides of the tRNA. In the small cell, the entire protein is ordered with the exception of the C-terminal, Zn-binding domain, a region between residues 205–390 in the editing domain and the last 2 nucleotides of the tRNA. Improvement in the phases was monitored by an increase in the real space correlation coefficient in O (Jones et al., 1994). When the coordinates of $T.$ $thermophilus$ IRS (Nureki et al., 1998) became available, we were able to re-interpret the region of residues between 205–390 in the editing domain in the small cell.

Example 4
Computer Modeling of Isoleucyl-tRNA Synthetases from Human and MUR$SA$ Human isoleucyl-tRNA synthetase has A65 and G66, corresponding to N70 and K71 of IRS in $SA$. The modeling of the human enzyme was done by the removal of the respective side chains at the equivalent residues. MUR$SA$ has G55 and R56 at the same location. The mutation of N to G was done by the removal of the asparagine side chain, and the mutation of K to R by maintaining all side chain torsional angle values. A slightly $\chi 3$ rotation of the residue equivalent to E554 side chain would have resulted in better interactions with the modeled WSS-1 compound (see below for modeling procedure) at N7 and Nβ1 as well as with the enzyme itself. This was not done in the current modeling.

Example 5
Design of a New Antibiotic, WSS-1

The re-designed antibiotic, WSS-1, was a fusion product of an asparagine side chain to the existing antibiotic, mupirocin, through a methylene linker at O7 while replacing O7 with N7. The location of the side chain moiety would allow a cyclization of Cβ2 to both Cα and C16, to the latter of which it is attached in a chair conformation of the 6-membered ring. This ensures the side chain equivalent component will sit above G55 in MUR$SA$ and will be rejected by A65 in human. An introduction of a hydroxyl at Cγ1 and a reduction of the unsaturated bonds will allow its interaction with R56 in MUR$SA$, which is not present in the human enzyme. The stereochemistry of four carbon atoms in the new part of the antibiotic are all S-isomers (FIG. 4), and both hydroxyls at Cγ1 and Cγ2 point down, and both hydrogen at Cα and CP2 point up in FIG. 4. The replacement of O7 with N7 allows better interactions with the residue equivalent to E554 due to the missing asparagine (equivalent to N70) in the enzyme. No optimization of the enzyme structures was done after the antibiotic was placed in the binding cleft.

Example 6
Three tRNA Synthetase Structures

The structures of in vitro transcribed, unmodified $E.$ $coli$ isoleucyl-tRNA with $S.$ $aureus$ isoleucyl-tRNA synthetase in the presence of a synthetase inhibitor were determined by multiple isomorphous replacement, multiple anomalous dispersion methods, and two-fold averaging (Silvian et al., 1999). The structure was refined to a final crystallographic R value of 23.9% and a free R-factor of 28.1% between 10 and 2.2 Å resolution. Both structures of $E.$ $coli$ QRS complex and $Tth$ apo IRS were previously determined (Rould et al., 1989, Rath et al., 1998, Nureki et al., 1998).

It should be understood that the foregoing discussion and examples merely present a detailed description of certain preferred embodiments. It therefore should be apparent to those of ordinary skill in the art that various modifications and equivalents can be made without departing from the spirit and scope of the invention.

All journal articles, other references, patents, and patent applications that are identified in this patent application are incorporated by reference in their entirety. Aspects of the work set forth in this application are also provided in Silvian et al. (1999), which is also incorporated by reference in its entirety.

REFERENCES FOR WHICH A COMPLETE CITATION IS NOT PROVIDED IN THE TEXT OF THE SPECIFICATION

Abrahams, J. P., and Leslie, A. G. W. (1996). Acta Cryst. D52, 30.

Alexander, R. G., Clayton, J. P., Luk, K., Rogers, N. H., and King, T. J. Title here. J. Chem. Soc., Perkin Trans. 1,561.

Anthony, R. M., Connor, A. M., Power, E. G., and French, G. L. (1999). Use of the polymerase chain reaction for rapid detection of high-level mupirocin resistance in staphylococci. Eur. J. Clin. Microbiol. Infect. Dis. 18, 30–34.

Archer, G. L. (1988). *Staphylococcus aureus*: a well-armed pathogen. Clin. Infect. Dis. 26, 1179–1181

Baldwin, A. N., Berg, P. (1966). Transfer ribonucleic acid-induced hydrolysis of valyladenylate bound to isoleucyl ribonucleic acid synthetase. J. Biol. Chem. 241, 839–845.

Banks, R. M., Donald, A. C., Hannan, P. C. T., O'Hanlon, P. J., and Rogers, N. H. (1989). Antimycoplasmal activities of the pseudomoinc acids and structure-activity relationships of monic acid A derivatives. J. Antibiotics, XLI, 609–613.

Bertino, J. S. Jr. (1997). Intranasal mupirocin for outbreaks of methicillin-resistant *Staphylococcus aureus*. Am. J. Health Syst. Pharm. 54, 2185–2191.

Borgfod, T. J., Brand, N. J., Gray, T. W., and Fersht, A. (1987a). The valyl-tRNA synthetase from *Bacillus stearothermophlius* has considerable sequence homology with the isoleucyl-tRNA synthetase from *Escherichia coli*. Biochemsitry 26, 2480–2486.

Borgford, T. J., Gray, T. E., Brand, N. J., and Fersht, A. R. (1987b). Site-directed mutagenesis reveals transition-state stabilization as a general catalytic mechanism for aminocyl-tRNA synthetases. *Biochemistry* 26, 7246–7250

Brick, P., Bhat, T. N., and Blow, D. M. (1988). Structure of tyrosyl-tRNA synthetase refined at 2.3 Å resolution. Interaction of the enzyme with the tyrosyl adenylate intermediate. *J. Mol. Biol.*, 208, 83–98.

Brown, P., Best, D. J., Broom, N. J., Cassels, R., O'Hanlon, P. J., Mitchell, J., Osborne, N. F., Wilson, J. M. (1997). The chemistry of pseudomonic acid. 18. Heterocyclic replacement of the α,β-unsaturated ester: synthesis, molecular modeling, and antibacterial activity. J. Med. Chem. 40, 2563–2570.

Brown, M. J. B., Mensah, L. M., Doyle, M. L., N. J. P. Broom, N. Osbourne, A. K. Forrest, C. M. Richardson, P. J. O. Hanlon and A. J. Pope (2000) Rational design of femtomolar inhibitors of isoleucyl tRNA Synthetase from a binding model for pseudomonic acid-A. *Biochemistry.* 39,6003–6011.

Brunie, S., Zelwer, C., and Risler, J. L. (1990). Crystallographic study at 2.5 A resolution of the interaction of methionyl-tRNA synthetase from *Escherichia coli* with ATP. *J. Mol. Biol.* 216, 411–424.

Brutlag, D., and Kornberg. A. (1972). Enzymatic synthesis of deoxyribonucleic acid. 36. A proofreading function for the 3' leads to 5' exonuclease activity in deoxyribonucleic acid polymerases. *J. Biol. Chem.* 247, 241–248.

Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T., and Warren, G. L. (1998). Crystallography & NMR system: A new software suite for macromolecular structure determination. Acta Crystallogr. D. Biol. Crystallogr. 54, 905–921.

Capobianco, J. O., Doran, C. C., and Goldman, R. C. (1989). Mechanism of mupirocin transport into sensitive and resistant bacteria. Antimicrob. Agents Chemother. 33, 156–163.

Carson, M. (1991). Ribbons 2.0. J. Appl. Crystallogr. 24, 958–961.

Casewell, M. W., and Hill, R. L. (1989). Mupirocin for eradication of nasal carriage of staphylococci. Lancet. 1, 154.

CCP4: Collaborative computational project No. 4. (1994). Acta Cryst. D50, 760.

Cedema, J. E., Terpenning, M. S., Ensberg, M., Bradley, S. F., and Kauffmnan, C. A. (1990). *Staphylococcus aureus* nasal colonization in a nursing home: eradication with mupirocin. Infect. Control Hosp. Epidemiol. 11, 13–16.

Chain, E. B., and Mellows, G. (1977). Pseudomonic acid. Part 1. The structure of pseudomonic acid A, a novel antibiotic produced by *Pseudomonas fluorescens*. J. Chem. Soc. Perkin 1, 294–309.

Chalker, A. F., Ward, J. M., Fosberry, A. P. and Hodgson, J. E. (1994). Analysis and toxic overexpression in *Escherichia coli* of a staphylococcal gene encoding isoleucyl-tRNA synthetase. Gene 141, 103–108.

Chambers, H. F., and Sachdeva, M. (1990). Binding of beta-lactam antibiotics to penicillin-binding proteins in methicillin-resistant *Staphylococcus aureus*. J. Infect. Dis. 161, 1170–1176.

Cool-Foley, A. A., Nathan, C., O'Donovan, C. III, and Simon, D. (1991). Eradication of methicillin-resistant Staphylococcus aureus vaginitis with mupirocin. DICP 25, 1331–1333.

Crimmin, M. J., O'Hanlon, P. J., Rogers, N. H., Sime, F. M., and Walker, G. (1989). The chemistry of pseudomonic acid. Part 11. Dehydrative cyclization of acylamino ketones to oxazoles. J. Chem. Soc., Perkin Trans. 1, 2059–2063.

Criminin, M. J., O'Hanlon, P. J., Rogers, N. H., Walker, G., (1989). The chemistry of pseudomonic acid. Part 10. Preparation of heterocyclic derivatives. J. Chem. Soc., Perkin Trans. 1, 2047–2057.

Dacre, J., Emmerson, A. M., and Jenner, E. A. (1986). Gentamicin-methicillin-resistant *Staphylococcus aureus*: epidemiology and containment of an outbreak. J. Hosp. Infect. 7, 130–136.

Denning, D. W., and Haiduven-Griffiths, D. (1988). Eradication of low-level methicillinresistant *Staphylococcus aureus* skin colonization with topical mupirocin. Infect. Control Hosp. Epidemiol. 9, 261–263.

Eldred, E. W., and Schimmel, P. R. (1972). Investigation of the transfer of amino acid from a transfer ribonucleic acid synthetase-aminoacyl adenylate complex to transfer ribonucleic acid. Biochemistry 11, 17–23.

Eltringham, I. (1997). Mupirocin resistance and methicillin-resistant *Staphylococcus aureus* (MRSA). J. Hosp. Infect. 35, 1–8.

Eom, S., Wang, J., and Steitz, T. A. (1996). Structure of Taq DNA polymerase with DNA at the polymerase active site. Nature 382, 278–281.

Farmer, T. H., Gilbart, J., and Elson, S. W. (1992). Biochemical basis of mupirocin resistance in strains of *Staphylococcus aureus*. J. Antimicrob. Chemother. 30, 587–596.

Fersht, A. R. (1977). Editing mechanism in protein synthesis. Rejection of valine by the isoleucyl-tRNA synthetase. *Biochemistry* 16, 1025–1030.

Fersht, A. R., and Dingwall, C. (1979 a). Evidence for the double-sieve editing mechanism in protein synthesis. Steric exclusion of isoleucine by valyl-tRNA synthetases. *Biochemistry* 18, 2627–2631

Fersht, A. R., and Dingwall, C. (1979b). An editing mechanism for the methionyl-tRNA synthetase in the selection of amino acids in protein synthesis. *Biochemistry* 8, 1250–1256.

Fersht, A. R., and Kaethner, M. M. (1976). Mechanism of aminoacylation of tRNA. Proof of the aminoacyl adenylate pathway for the isoleucyl- and tyrosyl-tRNA synthetases from *Escherichia coli* K12. Biochemistry 15, 818–823.

First, E. A., and Fersht, A. R. (1995). Analysis of the role of the KMSKS loop in the catalytic mechanism of the tyrosyl-tRNA synthetase using multimutant cycles. Biochemistry 34, 5030–5043.

Flores, P. A., and Gordon, S. M. (1997). Vancomycin-resistant *Staphylococcus aureus*: an emerging public health threat. Cleve. Clin. J. Med. 64, 527–532.

Freemont, P. S., Ollis, D. L., Steitz, T. A., and Joyce, C. M. (1986). A domain of the Klenow fragment of *Escherichia coli* DNA polymerase I has polymerase but no exonuclease activity. Proteins 1, 66–73

Freist, W. (1989). Mechanism of aminoacyl-tRNA synthetases: a critical consideration of recent results. Biochemistry 28, 6787–6795.

Friedman, A. M., Fischmann, T. O., Shamoo, Y., (1994). Abstract TRNO7. American Crystallographic Association Annual Meeting, Atlanta, Ga. USA Fuller, A. T., Mellows, G., Woolford, M., Banks, G. T., Barrow, K. D., and Chain, E. B. (1971). Pseudomonic acid: an antibiotic produced by *Pseudomonas fluorescens*. Nature 234, 416–417.

Fersht, A. R., Knill-Jones, J. W., Bedouelle, H., and Winter, G. (1988). Reconstruction by site-directed mutagenesis of the transition state for the activation of tyrosine by the tyrosyl-tRNA synthetase: a mobile loop envelopes the transition state in an induced-fit mechanism. *Biochemistry* 27, 1581–1587.

First, E. A., and Fersht, A. R. (1995). Analysis of the role of the KMSKS loop in the catalytic mechanism of the tyrosyl-tRNA synthetase using multimutant cycles. *Biochemistry* 34, 5030–5043.

Freemont, P. S., Ollis, D. L., Steitz, T. A., and Joyce, C. M. (1986). A domain of the Klenow fragment of *Escherichia coli* DNA polymerase I has polymerase but no exonuclease activity. *Proteins* 1, 66–73

Freist, W. (1989). Mechanism of aminoacyl-tRNA synthetases: a critical consideration of recent results. *Biochemistry* 28, 6787–6795.

Gilbart, J., Perry, C. R., and Slocombe, B. (1993). High-level mupirocin resistance in *Staphylococcus aureus*: evidence for two distinct isoleucyl-tRNA synthetases. Antimicrob. Agents Chemother. 37, 32–38.

Glasfeld, E., and Schimmel, P. (1997). Zinc-dependent tRNA binding by a peptide element within a tRNA synthetase. *Biochemistry* 36, 6739–6744.

Gould, D., and Chamberlaine, A. (1995). *Staphylococcus aureus*: a review of the literature. J. Clin. Nurs. 4 5–12

Hale, S. P., Auld, D. S., Schmidt, E., and Schimmel, P. (1997). Discrete determinants in transfer RNA for editing and aminoacylation. Science 276, 1250–1252.

Harbarth, S., Dharan, S., Liassine, N., Herrault, P., Auckenthaler, R., and Pittet, D. (1999). Randomized, placebo-controlled, double-blind trial to evaluate the efficacy of mupirocin for eradicating carriage of methicillin-resistant *Staphylococcus aureus*. Antimicrob. Agents Chemother. 43, 1412–1416.

Heck, J. D. and Hatfield, G. W. (1988). Valyl-tRNA synthetase gene of *Escherichia coli* K12. Primary structure and homology within a family of aminoacyl-tRNA synthetases. J. Biol. Chem. 263, 868–877.

Hodgson, J. E., Cumock, S. P., Dyke, K. G., Morris, R., Sylvester, D. R. and Gross, M. S. (1994). Molecular characterization of the gene encoding high-level mupirocin resistance in *Staphylococcus aureus* J2870. Antimicrob. Agents Chemother. 38 1205–1208.

Holm, L., and Sander, C. (1998). Disctionary of recurrent domains in protein structures. Proteins 33, 88–96.

Huberman, J. A., and Komberg, A. (1970). Enzymatic synthesis of deoxyribonucleic acid. XXXV. A 3'-hydroxylribonucleotide binding site of *Escherichia coli* deoxyribonucleic acid polymerase. J. Biol. Chem. 245, 5326–5334

Hughes, J., and Mellows, G. (1978a). Inhibition of isoleucyl-transfer ribonucleic acid synthetase in *Escherichia coli* by pseudomonic acid. Biochem J. 176, 305–318.

Hughes, J., and Mellows, G. (1978 b). On the mode of action of pseudomonic acid: inhibition of protein synthesis in *Staphylococcus aureus*. J. Antibiot. (Tokyo) 31, 330–335.

Hughes, J., and Mellows, G. (1980). Interaction of pseudomonic acid A with *Escherichia coli* B isoleucyl-tRNA synthetase. Biochem J. 191, 209–219.

Johnson, K. A. (1993). Conformational coupling in DNA polymerase fidelity. Annu Rev Biochem 62, 685–713

Jones, T. A., Zou, J.-Y., Cowan, S. W., and Kjeldgaard, M. (1991). Improved methods for building models in electron density maps and the location of errors in these models. Acta Crystallogr. A47, 110–119.

Kim, S. H., Sussman, J. L., Suddath, F. L., Quigley, G. J., McPherson, A., Wang, A. H., Seeman, N. C., and Rich, A., (1974). The general structure of transfer RNA molecules. Proc. Natl. Acad. Sci. USA, 71, 4970–4974.

Klein, L. L., Yeung, C. M., Kurath, P., Mao, J. C., Fernandes, P. B., Lartey, P. A., and Pernet, A. G. (1989). Synthesis and activity of nonhydrolyzable pseudomonic acid analogues. J. Med. Chem. 32, 151–160.

Loftfiled, R. B. (1963). The frequency of errors in protein biosynthesis. Biochem. J. 89, 82–92.

Loftfield, R. B., Eigner, E. A., Pastuszyn, A., Lovgren, T. N., and Jakubowski, H. (1980). Conforrnational changes during enzyme catalysis: role of water in the transition state. Proc. Natl. Acad. Sci. U.S.A. 77, 3374–3378.

Loftfield, R. B., and Vanderjagt, D. (1972). The frequency of errors in protein biosynthesis. Biochem J. 128, 1353–1356.

Lovgren, T. N., Pastuszyn, A., and Loftfield, R. B. (1976). The mechanism of the aminoacylation of transfer ribonucleic acid: enzyme-product dissociation is not rate limiting. Biochemistry 15, 2533–2540.

Lowe, D. M., Fersht, A. R., Wilkinson, A. J., Carter, P., and Winter, G. (1985). Probing histidine-substrate interactions in tyrosyl-tRNA synthetase using asparagine and glutamine replacements. Biochemistry 24, 5106–5109.

Lyon, B. R., and Skurray, R. (1987). Antimicrobial resistance of *Staphylococcus aureus*: genetic basis. Microbiol. Rev. 51, 88–134.

Mechulam, Y., Dardel, F., Le Corre, D., Blanquet, S., Gayat, G. (1991). Lysine 335, part of the KMSKS signature sequence, plays a crucial role in the amino acid activation catalysed by the methionyl-tRNA synthetase from *Echerichia Coli*. J. Mol. Biol. 217, 465–475.

Mellows, G. (1985). pp 7–8. In Bactroban: Proceedings of an International Symposium. Dobson, R. L., Leyden, J. J., Noble, W. C., and Price, J. D. Eds. Excerpta Medica. Amsterdam, The Netherlands.

Misra, S., and Hurley, J. H. (1999). Crystal structure of a phosphatidylinositol 3-phosphate-specific membrane-targeting motif, the FYVE domain of Vps27p. *Cell* 97, 657–666.

Monteilhet, C., Blow, D. M., and Brick, P. (1984). Interactions of crystalline tyrosyl-tRNA synthetase with adenosine, adenosine monophosphate, adenosine triphosphate and pyrophosphate in the presence of tyrosinol. *J. Mol. Biol.* 173, 477–485.

Mulligan, M. E., Murray-Leisure, K. A., Ribner, B. S., Standiford, H. C., John, J. F., Korvick, J. A., Kauffman, C. A., and Yu, V. L. (1993). Methicillin-resistant *Staphylococcus aureus*: a consensus review of the microbiology, pathogenesis, and epidemiology with implications for prevention and management. Am. J. Med. 94, 313–328

Murakami, K., and Tomasz, A. (1989). Involvement of multiple genetic determinants in high-level methicillin resistance in *Staphylococcus aureus*. J. Bacteriol. 171, 874–879.

Neu, H. C., (1991) in Human Pharmacology, Wingard, L. E. Jr., Brody, T. M., Lerner, J., and Schwartz, Eds., Mosby-Year Book, New York, pp 613–698.

Neu, H. C. (1992) The crisis in antibiotic resistance. Science 257, 1064–1073.

Nordin, B. E. and Schimmel, P. (1999). RNA determinants for translation editing. Mischarging a minihelix substrate by a tRNA synthetase. *J. Biol. Chem.* 274, 6835–6838.

Nureki, O., Vassylyev, D. G., Tateno, M., Shimada, A., Nakama, T., Fukai, S., Konno, M., Hendrickson, T. L., Schimmel, P., Yokoyama, S. (1998). Enzyme structure with two catalytic sites for double-sieve selection of substrate. Science 280, 578–582.

Nureki, O., Kohno, T., Kensaku, S., Miyazawa, T., and Yokoyama, S. (1993). Chemical modification and mutagenesis studies on zinc binding of arninoacyl-tRNA synthetase. *J. Biol. Chem.* 268, 15368–15373.

Ollis, D. L., Brick, P., Hamlin, R., Xuong, N. G., and Steitz, T. A. (1985). Structure of large fragment of *Escherichia coli* DNA polymerase I complexed with dTMP. Nature 313, 762–766.

Paterson, D. L. (1999). Reduced susceptibility of *Staphylococcus aureus* to vancomycin—a review of current knowledge. Commun. Dis. Intell. 23, 69–73.

Pauling, L., (1958). In Festschrift fur Prof. Dr. Arthur Stoll, Birhauser Verlag, Basel, pp. 597–602.

Perl, T. M. (1999). The threat of vancomycin resistance. Am. J. Med. 106(5 A), 26S–37S; and discussion 48S–52S.

Perona, J. J., Rould, M. A., Steitz, T. A., Risler, J. L., Zelwer, C., & Brunie, S. (1991). Structural similarities in glutaminyl- and methionyl-tRNA synthetase suggest a common overall orientation of tRNA binding. *Proc. Natl. Acad. Sci. USA* 88, 2903–2907.

Ponder, J. W., and Richards, F. M. (1987). Tertiary templates for proteins. Use of packing criteria in the enumeration of allowed sequences for different structural classes. J. Mol. Biol. 193, 775–791.

Pope, A. J., McVey, M., Fantom, K., and Moore, K. J. (1998). Effects of substrate and inhibitor binding on proteolysis of isoleucyl-tRNA synthetase from *Staphylococcus aureus*. J. Biol. Chem. 273, 31702–31706.

Pope, A. J., Moore, K. J., McVey, M., Mensah, L., Benson, N., Osbourne, N., Broom, N., Brown, M. J., and O'Hanlon, P. (1998). Characterization of isoleucyl-tRNA synthetase from *Staphylococcus aureus*. II. Mechanism of inhibition by reaction intermediate and pseudomonic acid analogues studied using transient and steady-state kinetics. J. Biol. Chem. 273, 31691–31701.

Rath, V. L., Silvian, L. F., Beijer, B., Sproat, B. S., and Steitz, T. A. (1998). How glutaminyl-tRNA synthetase selects glutamine. *Structure* 6, 439–449.

Redhead, R. J., Lamb, Y. J., and Rowsell, R. B. (1991). The efficacy of calcium mupirocin in the eradication of nasal *Staphylococcus aureus* carriage. Br. J. Clin. Pract. 45, 252–254.

Rogers, N. H., U.S. Pat. No. 4,200,635, April 1980 (Beecham Group, Ltd).

Rogers, N. H., Coulton, S., U.S. Pat. No. 4,312,874, January 1982 (Beecham Group, Ltd).

Rould, M. A., Perona, J. J., and Steitz, T. A. (1992). Acta Cryst. A48, 751.

Rould, M. A., Perona, J. J., Soll, D., and Steitz, T. A. (1989). Structure of *E. coli* glutaminyl-tRNA synthetase complexed with tRNA(Gln) and ATP at 2.8 Å resolution. *Science* 246, 1135–1142.

Schmitz, F. J., Lindenlauf, E., Hofmann, B., Fluit, A. C., Verhoef, J., Heinz, H. P., Jones, and M. E. (1998). The prevalence of low- and high-level mupirocin resistance in staphylococci from 19 European hospitals. J. Antimicrob. Chemother. 42, 489–495.

Setlow, P., Brutlag, D., and Kornberg, A. (1972). Deoxyribonucleic acid polymerase: two distinct enzymes in one polypeptide. I. A proteolytic fragment containing the polymerase and 3' leads to 5' exonuclease functions. J. Biol. Chem. 247, 224–231.

Shiba, K., Suzuki, N., Shigesada, K., Namba, Y., Schimmel, P. and Noda, T. (1994). Human cytoplasmic isoleucyl-tRNA synthetase: selective divergence of the anticodon-binding domain and acquisition of a new structural unit. Proc. Natl. Acad. Sci. U.S.A. 91, 7435–7439.

Silvian, L. F., Wang, J. and Steitz, T. A. (1999). Insights into editing from an Ile-tRNA synthetase structure with tRNA$^{ile}$ and mupirocin. *Science*. 285, 1074–1077.

Steitz, T. A. (1999). DNA pqlymerases: structural diversity and common mechanisms. J. Biol. Chem. 274, 17395–17398.

Stoldt, M., Wohnert, J., Gorlach, M., and Brown, L. R. (I1998). The NMR structure of *Escherichia coli* ribosomal protein L25 shows homology to general stress proteins and glutaminyl-tRNA synthetase. *EMBO. J.* 17, 6377–6384.

Terwilliger, T. C., (1994). Acta Cryst. D50, 17.

Tesch, W., Strassle, A., Berger-Bachi, B., O'Hara, D., Reynolds, P., and Kayser, F. H. (1988). Cloning and expression of methicillin resistance from *Staphylococcus epidermidis* in *Staphylococcus carnosus*. Antimicrob. Agents Chemother. 32, 1494–1499.

Ubukata, K., Yamashita, N., and Konno, M. (1985). Occurrence of a beta-lactaminducible penicillin-binding protein in methicillin-resistant staphylococci. Antimicrob. Agents Chemother. 27, 851–857.

Unge, J., Aberg, A., Al-Kharadaghi, S., Nikulin, A., Nikonov, S., Davydova, N. L., Nevskaya, N., Garber, M., and Liljas, A. (1998). The crystal structure of ribosomal protein L22 from Thermus thermophilus: insights into the mechanism of erythromycin resistance. *Structure* 6, 1577–1586.

Vandenbroucke-Grauls C. (1994). Epidemiology of staphylococcal infections—a European perspective. J. Chemother. Suppl. 2, 67–70

Walker, G., Brown, P., Forest, A. K., O'Hanlon, P. J., and Pons, J. E. (1993). New antibacterial agents: synthesis and actibacterial activity of heterocyclic derivatives of pseudomonic acid. In Recent Advances in the Chemistry of Anti-infectious Agents; Royal Society of Chemistry, London, p106

Woodford, N., Watson, A. P., Patel, S., Jevon, M., Waghorn, D. J., and Cookson, B. D. (1998). Heterogeneous location of the mupA high-level mupirocin resistance gene in *Staphylococcus aureus*. J. Med. Microbiol. 47, 829–835.

Yanagisawa, T., Lee, J. T., Wu, H. C., and Kawakami, M. (1994). Relationship of protein structure of isoleucyl-tRNA synthetase with pseudomonic acid resistance of *Escherichia coli*. A proposed mode of action of pseudomonic acid as an inhibitor of isoleucyl-tRNA synthetase. J. Biol. Chem. 269, 24304–24309.

Yarus, M., and Berg, P. (1969). Recognition of tRNA by isoleucyl-tRNA synthetase. Effect of substrates on the dynamics of tRNA-enzyme interaction. J. Mol. Biol. 42, 171–189.

Zhou, L., and Rosevear, P. R., (1995). Mutation of the carboxyl terminal zinc binding and aminoacylation activity. *Biochem. Biophys. Res. Comm.* 216, 648–654.

What is claimed is:

1. A method of preparing a crystal of a complex comprising isoleucyl-tRNA synthetase (IRS) from *S. aureus* complexed with mupirocin and tRNA$^{ile}$ comprising:

(a) mixing IRS from *S. aureus*, mupirocin, and tRNA$^{ile}$ with a well solution to form a mixture;

(b) streak-seeding drops of the mixture of step (a);

(c) vapor equilibrating the seeded drops in a closed container against the well solution to obtain a crystal of the complex and to produce an equilibrated crystal drop solution;

(d) replacing the equilibrated crystal drop solution with a cryoprotectant; and (e) flash-freezing the crystal.

2. The method of claim 1, wherein the well solution comprises about 12% PEG 6K, about 0.3 M KCl, about 100 mM Na Cacodylate pH 6.3, about 100 mM MgSO$_4$, about 2 mM ZnCl$_2$ and about 0.1% β-octyl glutopyranoside.

3. The method of claim 1, wherein in step (c), the seeded drops are equilibrated by hanging drop method.

4. The method of claim 1, wherein in step (d) the cryoprotectant comprises about 20% PEG 6K, about 0.3M KCl, about 100 mM Na Cacodylate pH 6.3, about 100 mM MgSO$_4$, about 2 mM ZnCl$_2$ about 0.1% β-octyl glutopyranoside, and about 15% ethylene glycol.

5. The method of claim 1, wherein in step (e) the crystal is flash-frozen in liquid propane.

6. A crystal comprising isoleucyl-tRNA synthetase (IRS) from *S. aureus*, mupirocin and tRNA$^{ile}$.

7. The crystal of claim 6, wherein the crystal effectively diffracts X-rays for determination of atomic coordinates of the complex to a resolution of about 2.2 Å.

8. The crystal of claim 6, wherein the crystal has two unit cell sizes, wherein the first unit cell comprises the dimensions a=71 Å, b=100 Å and c=186 Å and wherein the second unit cell has the dimensions a=71 Å, b=100 Å and c=180 Å.

9. The crystal of claim 6, wherein the crystal belongs to the space group $P2_12_12_1$.

10. The crystal of claim 6, wherein the crystal comprises an atomic structure characterized by the coordinates deposited at the Protein Data bank with accession number PDB ID: 1FFY.

11. A method of identifying an agent that interacts with isoleucyl-tRNA synthetase (IRS) from *S. aureus* and tRNA$^{ile}$ comprising:

(a) obtaining a crystal of a complex comprising IRS from *S. aureus*, tRNA$^{ile}$ and mupirocin;

(b) obtaining the atomic coordinates of the crystal; and (c) using the atomic coordinates and one or more molecular modeling techniques to identify an agent that interacts with the IRS and tRNA$^{ile}$.

12. A method of identifying an agent that interacts with isoleucyl-tRNA synthetase (IRS) from *S. aureus* comprising:

(a) obtaining a crystal of a complex comprising IRS from *S. aureus*, tRNA$^{ile}$ and mupirocin by the method of claim 1;

(b) obtaining the atomic coordinates of the crystal; and (c) using the atomic coordinates and one or more molecular modeling techniques to identify an agent that interacts with the IRS.

13. The method of claim 11 or 12, wherein the one or more molecular modeling techniques are selected from the group consisting of graphic molecular modeling and computational chemistry.

14. The method of claim 11 or 12 further comprising contacting the agent with IRS and detecting binding of the agent to IRS.

15. The method of claim 14, wherein the IRS utilized throughout the method is from the same species.

16. The method of claim 11 or 12 further comprising:

(d) altering the agent identified in step (c); and (e) contacting the altered agent of step (d) with IRS and determining the binding of the altered agent to IRS.

17. The method of claim 16 wherein the altered agent is a therapeutic agent.

18. A method of identifying an inhibitor of protein synthesis comprising:

a) obtaining a crystal of a complex comprising isoleucyl-tRNA synthetase (IRS) from *S. aureus*, tRNA$^{ile}$ and mupirocin;

b) obtaining the atomic coordinates of the crystal;

c) using the atomic coordinates and molecular modeling techniques to identify an agent that interacts with the IRS;

d) assaying the inhibitory properties of the agent by administering it to a cell, a cell extract or purified IRS; and e) detecting protein synthesis, wherein a decrease in protein synthesis indicates that the agent is an inhibitor of protein synthesis.

19. The method of claim 18, wherein assaying the inhibitory properties of the agent comprises detecting protein synthesis and wherein a decrease in protein synthesis indicates that the agent is an inhibitor of protein synthesis.

20. The method of claim 18, wherein assaying the inhibitory properties of the agent comprises determining an inhibition constant for inhibiting isoleucyl-tRNA synthesis reaction by the agent.

21. A method of identifying an inhibitor of protein synthesis comprising:

a) obtaining a crystal of a complex comprising isoleucyl-tRNA synthetase (IRS) from *S. aureus*, tRNA$^{ile}$ and mupirocin by the method of claim 1;

b) obtaining the atomic coordinates of the crystal;

c) using the atomic coordinates and molecular modeling techniques to identify an agent that interacts with the IRS; and d) assaying the inhibitory properties of the agent by administering it to a cell, a cell extract or purified IRS to determine whether it is an inhibitor of protein synthesis.

22. The method of claim 21, wherein assaying the inhibitory properties of the agent comprises determining whether the agent inhibits isoleucyl-tRNA synthesis.

23. The method of claim 22, wherein whether the agent inhibits isoleucyl-tRNA synthesis is determined by measuring the generation of pyrophosphate or the formation of isoleucyl-tRNA$^{ile}$.

* * * * *